United States Patent
Morant et al.

(10) Patent No.: US 11,584,783 B2
(45) Date of Patent: Feb. 21, 2023

(54) PROCESSES FOR PRODUCING A FERMENTATION PRODUCT

(71) Applicant: NOVOZYMES A/S, Bagsvaerd (DK)

(72) Inventors: Marc Dominique Morant, Frederiksberg (DK); Tomoko Matsui, Chiba (JP); Kirk Matthew Schnorr, Holte (DK); Shiro Fukuyama, Chiba (JP); Noriko Tsutsumi, Chiba (JP); Zhengfang Kang, Raleigh, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 241 days.

(21) Appl. No.: 16/624,164

(22) PCT Filed: Jun. 26, 2018

(86) PCT No.: PCT/US2018/039443
§ 371 (c)(1),
(2) Date: Dec. 18, 2019

(87) PCT Pub. No.: WO2019/005755
PCT Pub. Date: Jan. 3, 2019

(65) Prior Publication Data
US 2020/0140495 A1    May 7, 2020

Related U.S. Application Data

(60) Provisional application No. 62/526,133, filed on Jun. 28, 2017.

(51) Int. Cl.
| | | |
|---|---|---|
| *C12P 7/06* | (2006.01) | |
| *C12P 19/14* | (2006.01) | |
| *C07K 14/39* | (2006.01) | |
| *C12N 9/24* | (2006.01) | |

(52) U.S. Cl.
CPC ............ *C07K 14/39* (2013.01); *C12N 9/2402* (2013.01); *C12P 7/06* (2013.01); *C12P 19/14* (2013.01); *C12Y 302/01028* (2013.01); *C12Y 302/01093* (2013.01)

(58) Field of Classification Search
CPC ..................................................... C07K 14/39
See application file for complete search history.

(56) References Cited

FOREIGN PATENT DOCUMENTS

| | | |
|---|---|---|
| WO | 2009/121058 A1 | 10/2010 |
| WO | 2012/027374 A2 | 3/2012 |
| WO | 2013/148993 A1 | 10/2013 |
| WO | 2014/202622 A2 | 12/2014 |
| WO | 2015/065978 A1 | 5/2015 |
| WO | 2016/205127 A1 | 12/2016 |

OTHER PUBLICATIONS

D'Enfert et al., PIR_80 database, accession No. T18304, Oct. 1999.*
Aeschbacher et al, 1999, Plant Physiol 119, 489-496.
Amaral et al, 1996, Can J Microbiol 41, 1057-1062.
Anonymous, 2015, ASM130527v1.
Cardello et al, 1994, Microbiology 140, 1671-1677.
De Vries et al, 2017, Uniprot No. A0A1L9RM22.
D'Enfert et al., 1997, Mol Microbiol 24, 203-216.
Dewerchin et al, 1984, J Bacteriol 158, 575-579.
Fujii et al, 2013, FEMS Microbiol Lett 351(1), 32-41.
Fujii et al, 2015, EBI Accession No. A0A0B8MYG3.
Grba et al, 1975, Eur J Appl Microbiol 2, 29-37.
Hecker et al, 1973, J Bacteriol 115, 592-599.
Heneghan et al, 2004, EBI Accession No. Q6V7X7.
Kadowaki et al, 1996, Biochim Biophys Acta 1291, 199-205.
Li et al, 2017, GenBank Accession No. CP017350.1.
Li et al, 2017, Scientific reports 7(1), 1-10.
Londesborough et al, 1984, Biochem J 219, 511-518.
Sumida et al, 1989, J Ferm Bioeng 67, 83-86.
Thevelein et al, 1983, J Gen Microbiol 129, 719-726.
Waters et al, 2011, Enzyme Microb Technol 49(2), 229-236.
Yang et al, 2014, EBI Accession No. A0A093V3X4.
Yang et al, 2014, PLOS 10(10), e1004662.
Zimmermann et al, 1990, Biochim Biophys Acta 1036, 41-46.
WO 2014-202622 A2—EBI Accession No. BBS02793.
WO 2014-202622 A2—EBI Accession No. BBS02964.
WO 2016-205127 A1—EBI Accession No. BDL37300.
Grijseels 2016 Scientific reports 6(1) 1-13, 6(1), Oct. 2016.
Grijseels_2017_EBI_Accession_No._A0A1F5LP28, Feb. 2017.
WO2016205127_EBI_accession_No._BDL37316, Dec. 2016.

* cited by examiner

*Primary Examiner* — Maryam Monshipouri
(74) *Attorney, Agent, or Firm* — David Fazzolare

(57) ABSTRACT

The present invention relates to polypeptides having trehalase activity, particularly derived from *Talaromyces*. The invention also relates to nucleic acid constructs, vectors, and host cells comprising the polynucleotides as well as methods of producing and using the polypeptides for the production of ethanol.

10 Claims, No Drawings

Specification includes a Sequence Listing.

PROCESSES FOR PRODUCING A FERMENTATION PRODUCT

CROSS-REFERENCE TO RELATED APPLICATIONS

This application is a 35 U.S.C. 371 national application of international application no. PCT/US2018/039443 filed Jun. 26, 2018, which claims priority or the benefit under 35 U.S.C. 119 of U.S. provisional application No. 62/526,133 filed Jun. 28, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having treahalase activity and polynucleotides encoding the polypeptides. The invention also relates to nucleic acid constructs, vectors, and host cells comprising the polynucleotides as well as methods of producing the polypeptides. The invention also relates to processes of producing fermentation products using a trehalase of the invention.

Description of the Related Art

Trehalose is a stable disaccharide sugar consisting of two sugar monomers (glucose). Trehalose is accumulated in yeast as a response to stress in up to 10-15% of cell dry weight (GrBa et al. (1975) Eur. J. Appl. Microbiol. 2:29-37). Trehalose cannot be metabolized by the yeast. The enzyme trehalase cleaves trehalose into two glucose units.

Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on the expasy website. The two enzyme classes are both referred to as "trehalases". Examples of neutral trehalases include trehalases from *Saccharomyces cerevisiae* (Londesborouh et al. (1984) Characterization of two trehalases from baker's yeast" Biochem J 219, 511-518; *Mucor roxii* (Dewerchin et al (1984), "Trehalase activity and cyclic AMP content during early development of *Mucor rouxii* spores", J. Bacteriol. 158, 575-579); *Phycomyces blakesleeanus* (Thevelein et al (1983), "Glucose-induced trehalase activation and trehalose mobilization during early germination of *Phycomyces blakesleeanus* spores" J. Gen Microbiol. 129, 719-726); *Fusarium oxysporium* (Amaral et al (1996), "Comparative study of two trehalase activities from *Fusarium oxysporium* var *Linii*" Can. J Microbiol. 41, 1057-1062). Examples of neutral trehalases include, but are not limited to, trehalases from *Saccharomyces cerevisiae* (Parvaeh et al. (1996) Purification and biochemical characterization of the ATH1 gene product, vacuolar acid trehalase from *Saccharomyces cerevisae*" FEBS Lett. 391, 273-278); *Neorospora crassa* (Hecker et al (1973), "Location of trehalase in the ascospores of *Neurospora*: Relation to ascospore dormancy and germination". J. Bacteriol. 115, 592-599); *Chaetomium aureum* (Sumida et al. (1989), "Purification and some properties of trehalase from *Chaetomium aureum* MS-27. J. Ferment. Bioeng. 67, 83-86); *Aspergillus nidulans* (d'Enfert et al. (1997), "Molecular characterization of the *Aspergillus nidulans* treA gene encoding an acid trehalase required for growth on trehalose. Mol. Microbiol. 24, 203-216); *Humicola grisea* (Zimmermann et al. (1990)." Purification and properties of an extracellular conidial trehalase from *Humicola grisea* var. *thermoidea*", Biochim. Acta 1036, 41-46); *Humicola grisea* (Cardello et al. (1994), "A cytosolic trehalase from the thermophilhilic fungus *Humicola grisea* var. *thermoidea*', Microbiology UK 140, 1671-1677; *Scytalidium thermophilum* (Kadowaki et al. (1996), "Characterization of the trehalose system from the thermophilic fungus *Scytalidium thermophilum*" Biochim. Biophys. Acta 1291, 199-205); and *Fusarium oxysporium* (Amaral et al (1996), "Comparative study of two trehalase activities from *Fusarium oxysporium* var *Linii*" Can. J Microbiol. 41, 1057-1062).

A trehalase is also know from soybean (Aeschbachet et al (1999)" Purification of the trehalase GmTRE1 from soybean nodules and cloning of its cDNA", Plant Physiol 119, 489-496).

Trehalases are also present in small intestine and kidney of mammals.

WO 2009/121058 (Novozymes) concerns a method of fermenting sugars derived from plant material into a fermentation product, such as ethanol, using a fermenting organism by adding one or more trehalase into in the fermentation medium.

WO 2012/027374 (Dyadic) discloses a trehalase from *Myceliophthora thermophila* which can be used in an enzyme mixture for degrading lignocellulosic biomass to fermentable sugars.

WO 2013/148993 (Novozymes) discloses a process of producing a fermentation product, such as ethanol, from starch-containing material by liquefying, saccharifying and fermenting the starch-containing material wherein wherein a carbohydrate-source generating enzyme, a cellulolytic composition and a trehalase is present in fermentation. A trehalase from *Trichoderma reesei* is disclosed.

WO 2015/065978 (Danisco US Inc.) discloses a method of increasing the production of ethanol from a liquefact in a fermentation reaction including fermenting the liquefact with a glucoamylase, a fermenting organism and a trehalase and recovering the ethanol and other fermentation products at the end of the fermentation.

WO 2016/205127 (Novozymes) discloses a trehalase from *Myceliophthora sepedonium* belonging to Family 37 Glucoside Hydrolases ("GH37") as defined by CAZY (available online), having high thermostability and a broad pH range. It was also found that an increased ethanol yield can be obtained when adding a trehalase to fermentation in an ethanol process.

Fujii T., et al., 2014, Taxonomic revision of the cellulose-degrading fungus *Acremonium cellulolyticus* nomen nudum to *Talaromyces* based on phylogenetic analysis. FEMS Microbiology Letters, 351: 32-41 and Uniprot: AOAOB8MYG3 disclose trehalases from *Talaromyces cellulyticus*, and Uniprot:AOA1 L9RM22 discloses a trehalase from *Aspergillus wentii*.

A trehalase from *Talaromyces verruculosus* was published in 2015 as part of a genome sequence on the NCBI website as assembly GCA 001305275.1; (polypeptide identified as EFP5BRM8N).

There is still a need for providing enzymes or enzyme composition suitable for use in processes for producing fermentation products, such as ethanol, in increased yields.

SUMMARY OF THE INVENTION

The present invention provides polypeptides having trehalase activity and polynucleotides encoding the polypeptides. The trehalases according to the invention have good stability towards degradation by proteases and high thermo-stability. The trehalases are preferably obtained from a fungus of the genus *Talaromyces*.

Accordingly, the present invention relates to polypeptides having trehalase activity selected from the group consisting of:

(a) a polypeptide having at least 93% sequence identity to the mature polypeptide of SEQ ID NO: 21 or at least 70% sequence identity to the mature polypeptide of SEQ ID NO: 23;

(b) a polypeptide encoded by a polynucleotide having at least 95% sequence identity to the mature polypeptide coding sequence of SEQ ID NO: 20 or the cDNA sequence thereof; or at least 80% sequence identity to the mature polypeptide coding sequence of SEQ ID NO: 22 or the cDNA sequence thereof;

(c) a variant of the mature polypeptide of SEQ ID NO: 21 or SEQ ID NO: 23 comprising a substitution, deletion, and/or insertion at one or more (e.g., several) positions; and (d) a fragment of the polypeptide of (a), (b), or (c), that has trehalase activity.

In further aspect the present invention relates to polynucleotides encoding the variants; nucleic acid constructs, vectors, and host cells comprising the polynucleotides; and methods of producing the variants. In a further aspect the present invention relates to compositions comprising the variants of the invention.

The present invention also relates to a process of producing a fermentation product, comprising (a) liquefying a starch-containing material with an alpha-amylase;

optionally pre-saccharifying the liquefied material before step (b);

(b) saccharifying the liquefied material;
(c) fermenting using a fermentation organism;
wherein
i) a glucoamylase;
ii) a trehalase of the invention;
iii) optionally a cellulolytic enzyme composition and/or a protease; are present and/or added during
saccharification step (b);
fermentation step (c);
simultaneous saccharification and fermentation;
optionally presaccharification step before step (b).

In still further aspects the present invention relates to process of producing fermentation products from starch-containing material comprising:

(i) saccharifying a starch-containing material at a temperature below the initial gelatinization temperature; and (ii) fermenting using a fermentation organism;

wherein saccharification and/or fermentation is done in the presence of the following enzymes: glucoamylase, alpha-amylase, trehalase of any of claims 1-7, and optionally a protease and/or a cellulolytic enzyme composition.

Definitions

Trehalase: The term "trehalase" means an enzyme which degrades trehalose into its unit monosaccharides (i.e., glucose). Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on the expasy website. Trehalases are enzymes that catalyze the following reactions:

EC 3.2.1.28:

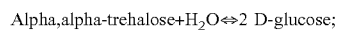

Alpha,alpha-trehalose+$H_2O$⇌2 D-glucose;

EC 3.2.1.93:

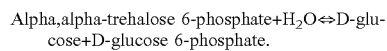

Alpha,alpha-trehalose 6-phosphate+$H_2O$⇌D-glucose+D-glucose 6-phosphate.

For purposes of the present invention, trehalase activity may be determined according to "Trehalase Assay" procedure described in the "Materials & Methods"-section. In one aspect, the polypeptides of the present invention have at least 20%, e.g., at least 40%, at least 50%, at least 60%, at least 70%, at least 80%, at least 90%, at least 95%, or at least 100% of the trehalase activity of the mature polypeptide of SEQ ID NO: 21. In another aspect, the polypeptides of the present invention have at least 20%, e.g., at least 40%, at least 50%, at least 60%, at least 70%, at least 80%, at least 90%, at least 95%, or at least 100% of the trehalase activity of the mature polypeptide of SEQ ID NO: 23. In a preferred embodiment a trehalase of the invention is a Family 65 Glycoside Hydrolase ("GH65 trehalase").

In one embodiment the trehalases according to the invention, SEQ ID NO: 21 and/or SEQ ID NO: 23 have a denaturing temperature Td (measured by the TSA assay) of at least 60° C., at least 61° C., at least 62° C., at least 63° C., at least 64° C., at least 65° C., at least 66° C., at least 67° C., such as at least 68° C.

In another embodiment the trehalases according to the invention, SEQ ID NO: 21 and/or SEQ ID NO: 23 have a residual activity after 3 days incubation at 40° C. with an *A. niger* protease mixture of 100%.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme. In one embodiment the catalytic domain is amino acids 387 to 769 of SEQ ID NO: 21. In another embodiment the catalytic domain is amino acids 384 to 799 of SEQ ID NO: 23.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has trehalase activity. In one aspect, a fragment contains amino acids 387 to 769 of SEQ ID NO: 21. In one aspect, a fragment contains at least amino acids 384 to 799 of SEQ ID NO: 23.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to thermostability, wherein the denaturing temperature (Td) measure by Thermal Shift Assay (TSA) is at least 60° C., at least 61° C., at least 62° C., at least 63° C., at least 64° C., at least 65° C., at least 66° C., at least 67° C., such as at least 68° C. and stability against protease degradation, in particular degradation by *Aspergillus niger* protease mixture.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 1038 of SEQ ID NO: 21. In another aspect, the mature polypeptide is amino acids 21 to 1089 of SEQ ID NO: 23. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having trehalase activity. In one aspect, the mature polypeptide coding sequence is nucleotides 55 to 2037, and 2085 to 3161 of SEQ ID NO: 20. Nucleotides 1 to 54 of SEQ ID NO: 20 encode a signal peptide. In another aspect, the mature polypeptide coding sequence is nucleotides 61 to 1740, and 2026 to 2313, and 2367 to 3605 of SEQ ID NO: 22. Nucleotides 1 to 60 of SEQ ID NO: 22 encode a signal peptide.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences. In one embodiment the one or more control sequences are heterologous (of different origin/species) to the coding sequence encoding the polypeptide of the invention.

Operably linked: The term "operably linked" means a configuration in which a control sequence is placed at an appropriate position relative to the coding sequence of a polynucleotide such that the control sequence directs expression of the coding sequence.

Parent or parent trehalase: The term "parent" or "parent trehalase" means any polypeptide with trehalase activity to which an alteration is made to produce an enzyme variants of the present invention.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having trehalase activity. In one aspect, a subsequence contains at least nucleotides 1159 to 2037, and 2085 to 2354 of SEQ ID NO: 20. In one aspect, a subsequence contains at least nucleotides 1150 to 1740, and 2026 to 2313, and 2367 to 2735 of SEQ ID NO: 22.

Variant: The term "variant" means a polypeptide having trehalase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 50%, at least 60%, at least 70%, at least 80%, at least 90%, at least 95%, or at least 100% of the trehalase activity of the polypeptide of SEQ ID NO: 21. The variants of the present invention have at least 20%, e.g., at least 40%, at least 50%, at least 60%, at least 70%, at least 80%, at least 90%, at least 95%, or at least 100% of the trehalase activity of the polypeptide of SEQ ID NO: 23.

Wild-type trehalase: The term "wild-type" trehalase means a trehalase expressed by a naturally occurring microorganism, such as a bacterium, yeast, or filamentous fungus found in nature.

DETAILED DESCRIPTION OF THE INVENTION

Polypeptides Having Trehalse Activity

In an embodiment, the present invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 21.

In a particular embodiment the invention relates to polypeptides having a sequence identity to the mature polypeptide of SEQ ID NO: 21 of at least 80%, at least 85%, at least 90%, at least 91%, at least 92%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the trehalase activity of the mature polypeptide of SEQ ID NO: 21, and wherein the denaturing temperature measured by TSA is at least 60° C.

In an embodiment, the present invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 23.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, least 91%, at least 92%, at least 93%, at least 94%, at least 95%, at least 96%, at least 97%, at least 98%, at least 99%, or 100%, and wherein the polypeptide has at least at least 75% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, 90%, 91%, at least 92%, at least 93%, at least 94%, at least 95%, at least 96%, at least 97%, at least 98%, at least 99%, or 100%, and wherein the polypeptide has at least at least 95% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the trehalase activity of the mature polypeptide of SEQ ID NO: 23, and wherein the denaturing temperature measured by TSA is at least 60° C.

In an embodiment, the polypeptide has been isolated. A polypeptide of the present invention preferably comprises or consists of the amino acid sequence of SEQ ID NO: 21 or an allelic variant thereof; or is a fragment thereof having trehalase activity. In another aspect, the polypeptide comprises or consists of the mature polypeptide of SEQ ID NO: 21. In another aspect, the polypeptide comprises or consists of amino acids 19 to 1038 of SEQ ID NO: 21.

In an embodiment, the polypeptide has been isolated. A polypeptide of the present invention preferably comprises or consists of the amino acid sequence of SEQ ID NO: 23 or an allelic variant thereof; or is a fragment thereof having trehalase activity. In another aspect, the polypeptide comprises or consists of the mature polypeptide of SEQ ID NO: 23. In another aspect, the polypeptide comprises or consists of amino acids 21 to 1089 of SEQ ID NO: 23.

In another embodiment, the present invention relates to a polypeptide having trehalase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 20, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.). In an embodiment, the polypeptide has been isolated.

In another embodiment, the present invention relates to a polypeptide having trehalase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 22, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.). In an embodiment, the polypeptide has been isolated.

The polynucleotide of SEQ ID NO: 20 or SEQ ID NO: 22 or a subsequence thereof, as well as the polypeptide of SEQ ID NO: 21 or SEQ ID NO: 23 or a fragments thereof may be used to design nucleic acid probes to identify and clone DNA encoding polypeptides having trehalase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having trehalase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 20 or 22; (ii) the mature polypeptide coding sequence of SEQ ID NO: 20 or 22; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In another embodiment, the present invention relates to an polypeptide having trehalase activity encoded by a polynucleotide having a sequence identity to the mature polypeptide coding sequence of SEQ ID NO: 20 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to an polypeptide having trehalase activity encoded by a polynucleotide having a sequence identity to the mature polypeptide coding sequence of SEQ ID NO: 22 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 21 comprising a substitution, deletion, and/or insertion at one or more (e.g., several) positions. In an embodiment, the number of amino acid substitutions, deletions and/or insertions introduced into the mature polypeptide of SEQ ID NO: 21 is up to 10, e.g., 1, 2, 3, 4, 5, 6, 7, 8, 9, or 10.

In another embodiment, the present invention relates to variants of the mature polypeptide of SEQ ID NO: 23 comprising a substitution, deletion, and/or insertion at one or more (e.g., several) positions. In an embodiment, the number of amino acid substitutions, deletions and/or insertions introduced into the mature polypeptide of SEQ ID NO: 23 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for trehalase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Trehalase Activity

A polypeptide having trehalase activity of the present invention may be obtained from microorganisms of genus *Talaromyces*. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Talaromyces* polypeptide, e.g., a polypeptide obtained from *Talaromyces funiculosus* or from *Talaromyces leycettanus*, such as e.g., CBS 398.68.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 387 to 769 of SEQ ID NO: 21 of at least at least 80%, at least 85%, at least 90, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 387 to 769 of SEQ ID NO: 21.

The catalytic domain preferably comprises or consists of amino acids 387 to 769 of SEQ ID NO: 21; or is a fragment thereof having trehalase activity.

In another embodiment, the present invention also relates to catalytic domains encoded by polynucleotides having a sequence identity to nucleotides 1159 to 2037, and 2085 to 2354 of SEQ ID NO: 20 or the cDNA sequence thereof of at least 80%, at least 85%, at least 90, at least 92%, at least 93%, at least 94%, at least 95%, at least 96%, at least 97%, at least 98%, at least 99%, or 100%.

The polynucleotide encoding the catalytic domain preferably comprises or consists of nucleotides 1159 to 2037, and 2085 to 2354 of SEQ ID NO: 20.

In another embodiment, the present invention also relates to catalytic domain variants of amino acids 387 to 769 of SEQ ID NO: 21 comprising a substitution, deletion, and/or insertion at one or more (e.g., several) positions. In one aspect, the number of amino acid substitutions, deletions and/or insertions introduced into the sequence of amino acids 387 to 769 of SEQ ID NO: 21 is up to 10, e.g., 1, 2, 3, 4, 5, 6, 8, 9, or 10.

In one embodiment, the present invention also relates to catalytic domains having a sequence identity to amino acids 384 to 799 of SEQ ID NO: 23 of at least 75%, at least 80%, at least 85%, at least 90, at least at least 93%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 384 to 799 of SEQ ID NO: 23.

The catalytic domain preferably comprises or consists of amino acids 384 to 799 of SEQ ID NO: 23 or an allelic variant thereof; or is a fragment thereof having trehalase activity.

In another embodiment, the present invention also relates to catalytic domains encoded by polynucleotides having a sequence identity to nucleotides 1150 to 1740, and 2026 to 2313, and 2367 to 2735 of SEQ ID NO: 22 or the cDNA sequence thereof of at least 75%, at least 80%, at least 85%, at least 90, at least 93%, at least 95%, at least 96%, at least 97%, at least 98%, at least 99%, or 100%.

The polynucleotide encoding the catalytic domain preferably comprises or consists of nucleotides 1150 to 1740, and 2026 to 2313, and 2367 to 2735 of SEQ ID NO: 22.

In another embodiment, the present invention also relates to catalytic domain variants of amino acids 384 to 799 of SEQ ID NO: 23 comprising a substitution, deletion, and/or insertion at one or more (e.g., several) positions. In one aspect, the number of amino acid substitutions, deletions and/or insertions introduced into the sequence of amino acids 384 to 799 of SEQ ID NO: 23 is up to 10, e.g., 1, 2, 3, 4, 5, 6, 8, 9, or 10.

Polynucleotides

The present invention also relates to polynucleotides encoding a polypeptide, or a catalytic domain of the present invention, as described herein. In an embodiment, the polynucleotide encoding the polypeptide, or catalytic domain, of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Talaromyces*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. In one particular embodiment at least one control sequence is heterologous (of different origin/species) to the polynucleotide encoding the variant of the present invention.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites.

Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. In a particular embodiment the recombinant host cell comprises the polynucleotide encoding a trehalase polypeptide of the present invention in which the said polynucleotide is heterologous (of different origin/species) to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. In a particular embodiment the whole broth formulation is generated by fermentation of a recombinant host cell of the invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide having trehalase activity of the present invention. Preferably, the compositions are enriched in such a polypeptide. The term "enriched" indicates that the trehalase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In an embodiment the composition comprises a trehalase of the invention and a glucoamylase. In an embodiment the composition comprises a trehalase of the invention and a glucoamylase derived from *Talaromyces emersonii* (e.g., SEQ ID NO: 4). In an embodiment the composition comprises a trehalase of the invention and a glucoamylase derived from *Gloeophyllum*, such as *G. serpiarium* (e.g., SEQ ID NO: 5) or *G. trabeum* (e.g., SEQ ID NO: 6). In an embodiment the composition comprises a trehalase of the invention, a glucoamylase and an alpha-amylase. In an embodiment the composition comprises a trehalase of the invention, a glucoamylase and an alpha-amylase derived from *Rhizomucor*, preferably a strain the *Rhizomucor pusillus*, such as a *Rhizomucor pusillus* alpha-amylase hybrid having an linker (e.g., from *Aspergillus niger*) and starch-bonding domain (e.g., from *Aspergillus niger*). In an embodiment the composition comprises a trehalase of the invention, a glucoamylase, an alpha-amylase and a cellulolytic enzyme composition. In an embodiment the composition comprises a trehalase of the invention, a glucoamylase, an alpha-amylase and a cellulolytic enzyme composition, wherein the cellulolytic composition is derived from *Trichoderma reesei*. In an embodiment the composition comprises a trehalase of the invention, a glucoamylase, an alpha-amylase and a protease. In an embodiment the composition comprises a trehalase of the invention, a glucoamylase, an alpha-amylase and a protease. The protease may be derived from *Thermoascus aurantiacus*. In an embodiment the composition comprises a trehalase of the invention, a glucoamylase, an alpha-amylase, a cellulolytic enzyme composition and a protease. In an embodiment the composition comprises a trehalase of the invention, a glucoamylase, e.g., derived from *Talaromyces emersonii, Gloeophyllum serpiarium* or *Gloephyllum trabeum*, an alpha-amylase, e.g., derived from *Rhizomucor pusillus*, in particular one having a linker and starch-binding domain, in particular derived from *Aspergillus niger*, in particular one having the following substitutions: G128D+D143N (using SEQ ID NO: 7 for numbering); a cellulolytic enzyme composition derived from *Trichoderma reesei*, and a protease, e.g., derived from *Thermoascus aurantiacus* or *Meripilus giganteus*.

Examples of specifically contemplated secondary enzymes, e.g., a glucoamylase from *Talaromyces emersonii* shown in SEQ ID NO: 4 herein or a glucoamylase having, e.g., at least 60%, at least 70%, at least 80%, at least 90%, at least 95%, at least 96%, at least 97%, at least 98%, at least 99% identity to SEQ ID NO: 4 herein can be found in the "Enzymes" section below. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

Processes of the Invention

Producing a Fermentation Product from Gelatinized Starch Material Using a Trehalase of the Invention In this aspect the present invention relates to producing a fermentation product, in particular ethanol, from gelatinized and/or ungelatinized starch-containing material or cellulosic material. Fermentable sugars generated during saccharification/hydrolysis are converted to the desired fermentation in question, in particular ethanol, during fermentation by a fermenting organism, in particular yeast.

In an embodiment the invention relates to processes of producing a fermentation product, in particular ethanol, comprising (a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase;
ii) a trehalase of the invention;
iii) optionally a cellulolytic enzyme composition and/or a protease;
are present and/or added during
   saccharification step (b);
   fermentation step (c);
   simultaneous saccharification and fermentation;
   optionally presaccharification step before step (b).

Liquefaction Step (a)

According to processes of the invention, liquefaction in step (a) is carried out by subjecting starch-containing material at a temperature above the initial gelatinization temperature, in particular at a temperature between 80-90° C., to an alpha-amylase and optionally a protease and other enzymes, such as a glucoamylase, a pullulanase and/or a phytase.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466.

According to the invention liquefaction in step (a) is typically carried out at a temperature in the range from 70-100° C. In an embodiment the temperature in liquefaction is between 75-95° C., such as between 75-90° C., preferably between 80-90° C., such as 82-88° C., such as around 85° C. The pH in liquefaction may be in the range between 3 and 7, preferably from 4 to 6, or more preferably from 4.5 to 5.5.

According to the invention a jet-cooking step may be carried out prior to liquefaction in step (a). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

In an embodiment, the process of the invention further comprises, prior to the liquefaction step (a), the steps of:
x) reducing the particle size of the starch-containing material, preferably by dry milling;
z) forming a slurry comprising the starch-containing material and water.

According to the invention the dry solid content (DS) in liquefaction lies in the range from 20-55 wt.-%, preferably 25-45 wt.-%, more preferably 30-40 wt.-% or 30-45 wt-%.

The starch-containing starting material, such as whole grains, may be reduced in particle size, e.g., by milling, in order to open up the structure, to increase surface area, and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. According to the present invention dry milling is preferred.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

Liquefaction in step (a) may be carried out for 0.5-5 hours, such as 1-3 hours, such as typically around 2 hours.

The alpha-amylase and other optional enzymes, such as protease, may initially be added to the aqueous slurry to initiate liquefaction (thinning). In an embodiment only a portion of the enzymes (e.g., about ⅓) is added to the aqueous slurry, while the rest of the enzymes (e.g., about ⅔) are added in liquefaction step (a).

A non-exhaustive list of examples of alpha-amylases can be found below in the "Alpha-Amylase Present and/or Added In Liquefaction"-section. In a preferred embodiment the alpha-amylase is a bacterial alpha-amylase. Bacterial alpha-amylases are typically thermostable. In a preferred embodiment the alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 8 herein.

In an embodiment the alpha-amylase used in liquefaction step (a) is a variant of the *Bacillus stearothermophilus* alpha-amylase shown in SEQ ID NO: 8 herein, in particular with the double deletions in I181*+G182*, and optionally with a N193F substitution, and truncated to be around 491 amino acids long, e.g., from 480-495 amino acids long.

Examples of suitable *Bacillus stearothermophilus* alpha-amylase variants can be found below in the "Thermostable Alpha-Amylase"-section and include one from the following group of *Bacillus stearothermophilus* alpha-amylase variants with double deletions I181*+G182*, and optionally substitution N193F, and additionally the following substitutions:

E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 8 for numbering).

According to processes of the invention, liquefaction in step (a) may be carried out using a combination of alpha-amylase (e.g., *Bacillus stearothermophilus* alpha-amylase shown in SEQ ID NO: 8) and protease (e.g., *Pyrococcus furiosus* (pfu protease) shown in SEQ ID NO: 9). A glucoamylase may also be present, such as the one derived from *Penicillium oxalicum* shown in SEQ ID NO: 10 herein (see the "Glucoamylase Present and/or Added In Liquefaction Step (a)"—section below.

Saccharification and Fermentation

A trehalase of the invention, a glucoamylase and optionally a protease and/or a cellulolytic enzyme composition may be present and/or added in saccharification step (b); fermentation step (c); simultaneous saccharification and fermentation (SSF); optionally a presaccharification step before step (b).

In a preferred embodiment the glucoamylase is added together with a fungal alpha-amylase, in particular acid fungal alpha-amylase. Examples of glucoamylases can be found in the "Glucoamylases Present and/or Added In Saccharification and/or Fermentation"-section below. When doing sequential saccharification and fermentation, saccharification step (b) may be carried out at conditions well-known in the art, i.e., suitable for enzyme saccharification. For instance, the saccharification step (b) may last up to from about 24 to about 72 hours.

In an embodiment pre-saccharification is done before saccharification in step (b). Pre-saccharification is typically done for 40-90 minutes at a temperature between 30-65° C., typically about 60° C. Pre-saccharification is in an embodiment followed by saccharification during fermentation in simultaneous saccharification and fermentation (SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step (b) and the fermentation step (c) are carried out simultaneously. There is no holding stage for the saccharification, meaning that a fermenting organism, in particular yeast, and enzymes, may be added together. However, it is also contemplated to add the fermenting organism and enzymes separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 4-5.

In an embodiment of the invention a cellulolytic composition is present and/or added in saccharification step (b), fermentation step (c) or simultaneous saccharification and fermentation (SSF) or pre-saccharification before step (b). Examples of such cellulolytic compositions can be found in the "Cellulolytic Enzyme Composition present and/or added during Saccharification and/or Fermentation"-section below. The optional cellulolytic enzyme composition may be present and/or added together with the glucoamylase and trehalase of the invention. Examples of proteases can be found in the "Proteases Present and/or Added In Saccharification and/or Fermentation"-section below.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

Starch-Containing Materials

According to the invention any suitable starch-containing starting material may be used. The starting material is generally selected based on the desired fermentation product, in particular ethanol. Examples of starch-containing starting materials, suitable for use in processes of the present invention, include cereal, tubers or grains. Specifically the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

In a preferred embodiment the starch-containing starting material is oats.

Producing a Fermentation Product from Ungelatinized Starch Material Using a Trehalase of the Invention A trehalase of the invention may suitably be used in a raw starch hydrolysis (RSH) process for producing desired fermentation products, in particular ethanol. In RSH processes the starch does not gelatinize as the process is carried out at temperatures below the initial gelatinization temperature of the starch in question (defined above).

The desired fermentation product may in an embodiment be ethanol produced from ungelatinized (i.e., uncooked), preferably milled, grains, such as corn, or small grains such as wheat, oats, barley, rye, rice, or cereals such as sorghum. Examples of suitable starch-containing starting materials are listed in the section "Starch-Containing Materials"-section above.

Accordingly, in this aspect the invention relates to processes of producing fermentation products from starch-containing material comprising:
(a) saccharifying a starch-containing material at a temperature below the initial gelatinization temperature; and
(b) fermenting using a fermentation organism; and
(c) optionally recovering the fermentation product;
wherein saccharification and/or fermentation is done in the presence of the following enzymes: glucoamylase, alpha-amylase, trehalase of the invention, and optionally a cellulolytic enzyme composition and/or a protease.

Before step (a) an aqueous slurry of starch-containing material, such as granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants. Because a raw starch hydrolysis process of the invention is carried out below the initial gelatinization temperature, and thus no significant viscosity increase takes place, high levels of stillage may be used, if desired. In an embodiment the aqueous slurry contains from about 1 to about 70 vol.-%, preferably 15-60% vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like.

In an embodiment backset, or another recycled stream, is added to the slurry before step (a), or to the saccharification (step (a)), or to the simultaneous saccharification and fermentation steps (combined step (a) and step (b)).

A RSH process of the invention is conducted at a temperature below the initial gelatinization temperature, which means that the temperature at which a separate step (a) is carried out typically lies in the range between 25-75° C., such as between 30-70° C., or between 45-60° C.

In a preferred embodiment the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

In an embodiment of the invention fermentation is carried out for 30 to 150 hours, preferably 48 to 96 hours. 66.

In an embodiment fermentation is carried out so that the sugar level, such as glucose level, is kept at a low level, such as below 6 wt.-%, such as below about 3 wt.-%, such as below about 2 wt.-%, such as below about 1 wt.-%., such as below about 0.5%, or below 0.25% wt.-%, such as below about 0.1 wt.-%. Such low levels of sugar can be accomplished by simply employing adjusted quantities of enzymes and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt.-%, such as below about 0.2 wt.-%.

The process of the invention may be carried out at a pH from 3 and 7, preferably from 3 to 6, or more preferably from 3.5 to 5.0.

The term "granular starch" means raw uncooked starch, i.e., starch in its natural form found in, e.g., cereal, tubers or grains. Starch is formed within plant cells as tiny granules insoluble in water. When put in cold water, the starch granules may absorb a small amount of the liquid and swell. At temperatures up to around 50° C. to 75° C. the swelling may be reversible. However, at higher temperatures an irreversible swelling called "gelatinization" begins. The granular starch may be a highly refined starch, preferably at least 90%, at least 95%, at least 97% or at least 99.5% pure, or it may be a more crude starch-containing materials comprising (e.g., milled) whole grains including non-starch fractions such as germ residues and fibers.

The raw material, such as whole grains, may be reduced in particle size, e.g., by milling, in order to open up the structure and allowing for further processing. Examples of suitable particle sizes are disclosed in U.S. Pat. No. 4,514,496 and WO2004/081193 (both references are incorporated by reference). Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In a preferred embodiment starch-containing material is prepared by reducing the particle size of the starch-containing material, preferably by milling, such that at least 50% of the starch-containing material has a particle size of 0.1-0.5 mm.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

According to the invention the enzymes are added so that the glucoamylase is present in an amount of 0.001 to 10 AGU/g DS, preferably from 0.01 to 5 AGU/g DS, especially 0.1 to 0.5 AGU/g DS.

According to the invention the enzymes are added so that the alpha-amylase is present or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

According to the invention the enzymes are added so that the cellulolytic enzyme composition is present or added in an amount 1-10,000 micro grams EP/g DS, such as 2-5,000, such as 3 and 1,000, such as 4 and 500 micro grams EP/g DS.

According to the invention the enzymes are added so that the cellulolytic enzyme composition is present or added in an amount in the range from 0.1-100 FPU per gram total solids (TS), preferably 0.5-50 FPU per gram TS, especially 1-20 FPU per gram TS.

In an embodiment of the invention the enzymes are added so that the protease is present in an amount of 0.0001-1 mg enzyme protein per g DS, preferably 0.001 to 0.1 mg enzyme protein per g DS. Alternatively, the protease is present and/or added in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment of the invention the enzymes are added so that the protease is present or added in an amount in the range 1-1,000 µg EP/g DS, such as 2-500 µg EP/g DS, such as 3-250 µg EP/g DS.

In a preferred embodiment ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In a preferred embodiment the total dose of glucoamylase and alpha-amylase is according to the invention from 10-1,000 µg/g DS, such as from 50-500 µg/g DS, such as 75-250 µg/g DS.

In a preferred embodiment the total dose of cellulolytic enzyme composition added is from 10-500 µg/g DS, such as from 20-400 µg/g DS, such as 20-300 µg/g DS.

In an embodiment the glucoamylase, such as one derived from *Trametes cingulata*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 11.

In an embodiment the glucoamylase, such as one derived from *Pycnoporus sanguineus*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 12.

In an embodiment the alpha-amylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 7.

In a preferred embodiment the invention relates to processes of producing fermentation products from starch-containing material comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase;
  ii) alpha-amylase;
  iii) trehalase of the invention;
  iii) optionally a cellulolytic enzyme composition and/or a protease.

In a preferred embodiment the enzymes may be added as an enzyme composition of the invention. In a preferred embodiment steps (a) and (b) are carried out simultaneously (i.e., one-step fermentation). However, step (a) and (b) may also be carried our sequentially.

Fermentation

Fermentation is carried out in a fermentation medium. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms for Starch Based Fermentation

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as in particular ethanol. Examples of fermenting organisms include fungal organisms, such as in particular yeast. Preferred yeast includes strains of *Saccharomyces* spp., in particular, *Saccharomyces cerevisiae*. In a particular embodiment the *S. cerevisiae* expresses the trehalase of the invention.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Recovery

Subsequent to fermentation, e.g., SSF, the fermentation product, in particular ethanol may be separated from the fermentation medium. The slurry may be distilled to recover/extract the desired fermentation product (i.e., ethanol). Alternatively the desired fermentation product (i.e., ethanol) may be extracted from the fermentation medium by micro or membrane filtration techniques. The fermentation product (i.e., ethanol) may also be recovered by stripping or other method well known in the art.

Alpha-Amylase Present and/or Added in Liquefaction

According to the invention an alpha-amylase is present and/or added in liquefaction optionally together with other enzymes such as a protease, a glucoamylase, phytase and/or pullulanase. The alpha-amylase added in liquefaction step (a) may be any alpha-amylase. Preferred are bacterial alpha-amylases, which typically are stable at temperatures used in liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 8 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 8 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids, e.g., so that it is between 480-495 amino acids long, so it lacks a functional starch binding domain (compared to SEQ ID NO: 3 in WO 99/19467) or SEQ ID NO: 8 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 8 herein or the deletion of amino acids R179 and G180 using SEQ ID NO: 3 in WO 99/19467 or SEQ ID NO: 8 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 8 herein. The bacterial alpha-amylase may also have a substitution in a position corresponding to S239 in the *Bacillus licheniformis* alpha-amylase shown in SEQ ID NO: 4 in WO 99/19467, or a S242 and/or E188P variant of the *Bacillus stearothermophilus* alpha-amylase of SEQ ID NO: 3 in WO 99/19467 or SEQ ID NO: 8 herein.

In an embodiment the variant is a S242A, E or Q variant, preferably a S242Q variant, of the *Bacillus stearothermophilus* alpha-amylase (using SEQ ID NO: 8 herein for numbering).

In an embodiment the variant is a position E188 variant, preferably E188P variant of the *Bacillus stearothermophilus* alpha-amylase (using SEQ ID NO: 8 herein for numbering).

The bacterial alpha-amylase may in an embodiment be a truncated *Bacillus* alpha-amylase. Especially the truncation is so that, e.g., the *Bacillus stearothermophilus* alpha-amylase shown in SEQ ID NO: 3 in WO 99/19467 or SEQ ID NO: 8 herein, is around 491 amino acids long, such as from 480 to 495 amino acids long, or so it lack a functional starch binding domain.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:

G48A+T491+G107A+H156Y+A181T+N190F+I201F+ A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

The alpha-amylase may be a thermostable alpha-amylase, such as a thermostable bacterial alpha-amylase, preferably from *Bacillus stearothermophilus*.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 8 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optionally substitution N193F, further comprising mutations selected from below list:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;

-continued

59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q +Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A + Q89R + E129V + K177L + R179E + Q254S + M284V.
V59A + E129V + K177L + R179E + Q254S + M284V;

Specific information about the thermostability of above alpha-amylases variants can be found in WO12/088303 (Novozymes) which is hereby incorporated by reference.

In a preferred embodiment the alpha-amylase is selected from the group of *Bacillus stearothermophilus* alpha-amylase variants having a double deletion in I181+G182, and optionally a substitution in N193F, and substitutions from the following list E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 8 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 8 herein, or variants thereof, are truncated in the C-terminal and are typically around 491 amino acids long, such as from 480-495 amino acids long, or so that it lacks a functional starch binding domain.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 8 herein.

In an embodiment the bacterial alpha-amylase, e.g., *Bacillus* alpha-amylase, such as especially *Bacillus stearothermophilus* alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In an embodiment the bacterial alpha-amylase, e.g., *Bacillus* alpha-amylase, such as especially *Bacillus stearothermophilus* alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

Protease Present and/or Added in Liquefaction

According to the invention a protease may optionally be present and/or added in liquefaction together with the alpha-amylase, and an optional glucoamylase, phytase and/or pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

In one embodiment the protease is of fungal origin.

The protease may be a variant of, e.g., a wild-type protease as long as the protease is thermostable. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 13 herein, further with mutations selected from below list:

S5*+D79L+S87P+A112P+D142L;
D79L+S87P+A 112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

Specific information about the thermostability of above protease variants can be found in WO12/088303 (Novozymes), which is hereby incorporated by reference.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 13 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 13 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), or SEQ ID NO: 9 herein.

In another embodiment the thermostable protease is one disclosed in SEQ ID NO: 22 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 9 herein. *Pyroccus furiosus* protease can be purchased from Takara Bio, Japan.

Glucoamylase Present and/or Added in Liquefaction

According to the invention a glucoamylase may optionally be present and/or added in liquefaction step (a). In a preferred embodiment the glucoamylase is added together with or separately from the alpha-amylase and optional protease, phytase and/or pullulanase.

In a specific and preferred embodiment the glucoamylase, preferably of fungal origin, preferably a filamentous fungi, is from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 10 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 10 herein.

In a preferred embodiment the glucoamylase is a variant of the *Penicillium oxalicum* glucoamylase disclosed as SEQ ID NO: 2 in WO 2011/127802 and shown in SEQ ID NO: 10 herein, having a K79V substitution (using the mature sequence shown in SEQ ID NO: 10 herein for numbering). The K79V glucoamylase variant has reduced sensitivity to protease degradation relative to the parent as disclosed in WO 2013/036526 (which is hereby incorporated by reference).

In an embodiment the glucoamylase is derived from *Penicillium oxalicum*.

In an embodiment the glucoamylase is a variant of the *Penicillium oxalicum* glucoamylase disclosed as SEQ ID NO: 2 in WO 2011/127802 and shown in SEQ ID NO: 10 herein. In a preferred embodiment the *Penicillium oxalicum* glucoamylase is the one disclosed as SEQ ID NO: 2 in WO 2011/127802 and shown in SEQ ID NO: 10 herein having Val (V) in position 79 (using SEQ ID NO: 23 herein for numbering).

Contemplated *Penicillium oxalicum* glucoamylase variants are disclosed in WO 2013/053801 which is hereby incorporated by reference.

In an embodiment these variants have reduced sensitivity to protease degradation.

In an embodiment these variant have improved thermostability compared to the parent.

More specifically, in an embodiment the glucoamylase has a K79V substitution (using SEQ ID NO: 10 herein for numbering), (PE001 variant), and further comprises at least one of the following substitutions or combination of substitutions:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+V79A+Q327F+E501V+Y504T; or
P2N+P4S+P11F+T65A+V79G+Q327F+E501V+Y504T; or
P2N+P4S+P11F+T65A+V79I+Q327F+E501V+Y504T; or
P2N+P4S+P11F+T65A+V79L+Q327F+E501V+Y504T; or
P2N+P4S+P11F+T65A+V79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the *Penicillium oxalicum* glucoamylase variant has a K79V substitution (using SEQ ID NO: 10 herein for numbering), corresponding to the PE001 variant, and further comprises one of the following mutations:
P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The glucoamylase may be added in amounts from 0.1-100 micrograms EP/g, such as 0.5-50 micrograms EP/g, such as 1-25 micrograms EP/g, such as 2-12 micrograms EP/g DS.

Trehalase Present and/or Added in Saccharification and/or Fermentation

According to the process of the invention a trehalase of the invention is present and/or added during the
saccharification step (b);
fermentation step (c);
simultaneous saccharification and fermentation;
optionally presaccharification step before step (b).

In a preferred embodiment the mature trehalase disclosed in SEQ ID NO: 21. In a preferred embodiment the mature trehalase disclosed in SEQ ID NO: 23. In a preferred embodiment the trehalase is present and/or added in an amount between 0.01-20 ug EP (Enzyme Protein) trehalase/g DS, such as between 0.05-15 ug EP terhalase/g DS, such as between 0.5 and 10 ug EP trehalase/g DS.

Glucoamylase Present and/or Added in Saccharification and/or Fermentation

The glucoamylase present and/or added during saccharification step (b); fermentation step (c); simultaneous saccharification and fermentation; or presaccharification before step (b), may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (US patent no. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831). Contemplated fungal glucoamylases include *Trametes* cingulate (SEQ ID NO: 11), *Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus sanguineus* as described in WO 2011/066576 (SEQ ID NOs 2, 4 or 6), in particular the one shown a SEQ ID NO: 12 herein (corresponding to SEQ ID NO: 4 in WO 2011/066576) or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 2 in WO 2011/068803 or SEQ ID NO: 5 herein (i.e. *Gloeophyllum sepiarium* glucoamylase). In a preferred embodiment the glucoamylase is SEQ ID NO: 6 herein (i.e., *Gloeophyllum trabeum* glucoamylase discloses as SEQ ID NO: 3 in WO2014/177546) (all references hereby incorporated by reference).

Contemplated are also glucoamylases which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 4, 11, 5, 6 or 12 herein, respectively.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 6 herein.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 12 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Glucoamylases may in an embodiment be added to the saccharification and/or fermentation in an amount of 1-1,000 µg EP/g DS, preferably 10-500 µg/gDS, especially between 25-250 µg/g DS.

In an embodiment the glucoamylase is added as a blend further comprising an alpha-amylase.

In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 34 or SEQ ID NO: 4 herein and *Trametes cingulata* glucoamylase disclosed as SEQ ID NO: 2 in WO 06/069289 and SEQ ID NO: 11 herein.

In an embodiment the glucoamylase is a blend comprising *Talaromyces emersonii* glucoamylase disclosed in SEQ ID NO: 4 herein, *Trametes cingulata* glucoamylase disclosed as SEQ ID NO: 11 herein, and *Rhizomucor pusillus* alpha-amylase with *Aspergillus niger* glucoamylase linker and SBD disclosed as V039 in Table 5 in WO 2006/069290 or SEQ ID NO: 7 herein.

In an embodiment the glucoamylase is a blend comprising *Gloeophyllum sepiarium* glucoamylase shown as SEQ ID NO: 5 herein and *Rhizomucor pusillus* alpha-amylase with an *Aspergillus niger* glucoamylase linker and starch-binding domain (SBD), disclosed SEQ ID NO: 7 herein with the following substitutions: G128D+D143N.

In an embodiment the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290 or SEQ ID NO: 7 herein.

In an embodiment the *Rhizomucor pusillus* alpha-amylase or the *Rhizomucor pusillus* alpha-amylase with a linker and starch-binding domain (SBD), preferably *Aspergillus niger* glucoamylase linker and SBD, has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering or SEQ ID NO: 7 herein). In a preferred embodiment the glucoamylase blend comprises *Gloeophyllum sepiarium* glucoamylase (e.g., SEQ ID NO: 2 in WO 2011/068803 or SEQ ID NO: 5 herein) and *Rhizomucor pusillus* alpha-amylase.

In a preferred embodiment the glucoamylase blend comprises *Gloeophyllum sepiarium* glucoamylase shown as SEQ ID NO: 2 in WO 2011/068803 or SEQ ID NO: 5 herein and *Rhizomucor pusillus* with a linker and starch-binding domain (SBD), preferably *Aspergillus niger* glucoamylase linker and SBD, disclosed SEQ ID NO: 3 in WO 2013/006756 and SEQ ID NO: 7 herein with the following substitutions: G128D+D143N.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE™, and AMG™ E (from Novozymes A/S); OPTIDEX™ 300, GC480, GC417 (from DuPont-Danisco); AMIGASE™ and AMIGASE™ PLUS (from DSM); G-ZYME™ G900, G-ZYME™ and G990 ZR (from DuPont-Danisco).

Cellulolytic Enzyme Composition Present and/or Added in Saccharification and/or Fermentation According to the invention a cellulolytic enzyme composition may be present in saccharification, fermentation or simultaneous saccharification and fermentation (SSF).

The cellulolytic enzyme composition comprises a beta-glucosidase, a cellobiohydrolase and an endoglucanase.

Examples of suitable cellulolytic composition can be found in WO 2008/151079 and WO 2013/028928 which are incorporated by reference.

In preferred embodiments the cellulolytic enzyme composition is derived from a strain of *Trichoderma, Humicola*, or *Chrysosporium*.

In an embodiment the cellulolytic enzyme composition is derived from a strain of *Trichoderma reesei, Humicola insolens* and/or *Chrysosporium lucknowense*.

In an embodiment the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (in particular the *Aspergillus oryzae* beta-glucosidase variant fusion protein shown in SEQ ID NOs: 73 and 74, respectively, in WO 2008/057637 or the *Aspergillus oryzae* beta-glucosidase fusion protein shown in SEQ ID NOs: 75 and 76, respectively, in WO 2008/057637—both hereby incorporated by reference), or *Aspergillus fumigatus*, such as one disclosed in WO 2005/047499 or SEQ ID NO: 14 herein or an *Aspergillus fumigatus* beta-glucosidase variant disclosed in WO 2012/044915 (Novozymes), such as one with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 2 in WO 2011/057140 or SEQ ID NO: 17 herein, or a strain of the genus *Trichoderma*, such as a strain of *Trichoderma reesei*.

In an embodiment the cellulolytic composition comprises a cellobiohydrolase II (CBH II, such as one derived from a strain of the genus *Aspergillus*, such as a strain of *Aspergillus fumigatus* disclosed as SEQ ID NO: 18 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the cellulolytic enzyme composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499 or SEQ ID NO: 14 herein).

In an embodiment the cellulolytic enzyme composition is a *Trichoderma reesei* cellulolytic enzyme composition further comprising *Penicillium emersonii* GH61A polypeptide having cellulolytic enhancing activity disclosed as SEQ ID NO: 2 in WO 2011/041397 or SEQ ID NO: 16 herein and *Aspergillus fumigatus* beta-glucosidase (SEQ ID NO: 2 of WO 2005/047499 or SEQ ID NO: 14 herein) or a variant thereof with the following substitutions F100D, S283G, N456E, F512Y (using SEQ ID NO: 14 herein for numbering).

In a preferred embodiment the cellulolytic enzyme composition comprising one or more of the following components:
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

In an preferred embodiment the cellulolytic enzyme composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 16 herein), *Aspergillus fumigatus* beta-glucosidase (SEQ ID NO: 2 in WO 2005/047499 or SEQ ID NO: 14 herein) variant with the following substitutions: F100D, S283G, N456E, F512Y (disclosed in WO 2012/044915); *Aspergillus fumigatus* Cel7A CBH I disclosed as SEQ ID NO: 6 in WO2011/057140 or SEQ ID NO: 6 herein and *Aspergillus fumigatus* CBH II disclosed as SEQ ID NO: 17 in WO 2011/057140 or SEQ ID NO: 18 herein.

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Proteases Present and/or Added in Saccharification and/or Fermentation

Any suitable protease may be added in saccharification and/or fermentation, such as SSF.

In a preferred embodiment the protease is a metallo protease or a serine protease. In an embodiment the enzyme composition comprises a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 13 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 13 herein.

In an embodiment the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 9 herein.

In an embodiment the protease is the mature sequence from *Meripilus giganteus* protease 3 (peptidase family S53 protease) concerned in Example 2 in WO 2014/037438 (hereby incorporated by reference). In an embodiment the protease is the mature protease 3 sequence from a strain of *Meripilus*, in particular *Meripilus giganteus* shown as SEQ ID NO: 5 in WO 2014/037438 (hereby incorporated by reference) and SEQ ID NO: 19 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 19 herein shown as amino acids 1-547.

Alpha-Amylase Present and/or Added in Saccharification and/or Fermentation

Any suitable alpha-amylase, such as fungal acid alpha-amylase, may be present and/or added in saccharification and/or fermentation.

In a preferably embodiment the alpha-amylase is a fungal alpha-amylase, in particular one that has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 7. In a preferred embodiment the alpha-amylase has one or more of the following substitutions: G128D, D143N, in particular G128D+D143N.

Processes of Producing a Fermentation Product from Cellulolic Materials Using a Trehalase of the Invention In an embodiment the invention relates to processes of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product,
wherein a trehalase of the invention is added and/or present in hydrolysis step (a) and/or fermentation step (b).

According to the process of the invention hydrolysis and fermentation may be carried out separate or simultaneous. In an embodiment the process of the invention is carried out as separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); or direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step. SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in a HHF process can be carried out at different temperatures, i.e., high temperature enzymatic hydrolysis followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product.

According to the invention the cellulosic material is plant material chips, plant stem segments and/or whole plant stems. In an embodiment cellulosic material is selected from the group comprising arundo, bagasse, bamboo, corn cob, corn fiber, corn stover, miscanthus, orange peel, rice straw, switchgrass, wheat straw. In a preferred embodiment the source of the cellulosic material is corn stover, corn cobs, and/or wheat straw.

According to the invention any pretreatment may be used. In a preferred embodiment chemical pretreatment, physical pretreatment, or chemical pretreatment and a physical pretreatment is used. In a preferred embodiment the cellulosic material is pretreated with an acid, such as dilute acid pretreatment. In an embodiment the cellulosic material is prepared by pretreating cellulosic material at high temperature, high pressure with an acid.

In an embodiment hydrolysis is carried out at a temperature between 20-70° C., such as 30-60° C., preferably 45-55° C. at a pH in the range 4-6, such as 4.5-5.5.

In an embodiment the cellulosic material is present at 1-20 (w/w) % of TS, such as 2-10 (w/w) % TS, such as around 5 (w/w) % TS during hydrolysis.

In an embodiment the hydrolysis is carried out for 1-20 days, preferably between from 5-15 days.

In an embodiment the cellulolytic enzyme composition is derived from *Trichoderma reesei, Humicola insolens* or *Chrysosporium lucknowense*.

Cellulolytic enzyme composition: The term "cellulolytic enzyme composition" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 21 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Examples of cellulolytic compositions can be found in the "Cellulolytic Enzyme Composition present and/or added during Saccharification and/or Fermentation"-section above.

Cellulosic material: The term "cellulosic material" means any material containing cellulose. The predominant polysaccharide in the primary cell wall of cellulosic material is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Tomme et al. method can be used to determine cellobiohydrolase activity.

Endoglucanase: The term "endoglucanase" means an endo-1,4-(1,3; 1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of cellulose when used in conjunction with a cellulase or a mixture of cellulases.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50C, 55° C., or 60° C., and pH, e.g., 5.0 or 5.5.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Fermenting Organism for Cellulosic Based Fermentation

The term "fermenting organism" or "fermenting microorganism" refers to any organism, including bacterial and fungal organisms, suitable for use in a desired fermentation process to produce a fermentation product. The fermenting organism may be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting organisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida* blankii. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida* scehatae. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*.

In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is

*Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, FEMS Yeast Research 4: 655-664; Beall et al., 1991, Parametric studies of ethanol production from xylose and other sugars by recombinant *Escherichia coli*, Biotech. Bioeng. 38: 296-303; Ingram et al., 1998, Metabolic engineering of bacteria for ethanol production, Biotechnol. Bioeng. 58: 204-214; Zhang et al., 1995, Metabolic engineering of a pentose metabolism pathway in ethanologenic *Zymomonas mobilis*, Science 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coil*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the term "fermentation product" can be any substance derived from fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515. In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, Miya, and Kiriyama, 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy*, 13(1-2): 83-114.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

Recovery

The fermentation product(s) are optionally recovered after fermentation using any method known in the art including, but not limited to, chromatography, electrophoretic procedures, differential solubility, distillation, or extraction. For example, alcohol, such as ethanol, is separated from the fermented material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further disclosed in the following numbered embodiments.

Embodiment 1

A polypeptide having trehalase activity, selected from the group consisting of:
(a) a polypeptide having at least 93% sequence identity to the mature polypeptide of SEQ ID NO: 21 or at least 70% sequence identity to the mature polypeptide of SEQ ID NO: 23;
(b) a polypeptide encoded by a polynucleotide having at least 95% sequence identity to the mature polypeptide coding sequence of SEQ ID NO: 20 or the cDNA sequence thereof; or at least 80% sequence identity to the mature polypeptide coding sequence of SEQ ID NO: 22 or the cDNA sequence thereof;
(c) a variant of the mature polypeptide of SEQ ID NO: 21 or SEQ ID NO: 23 comprising a substitution, deletion, and/or insertion at one or more (e.g., several) positions; and
(d) a fragment of the polypeptide of (a), (b), or (c), that has trehalase activity.

Embodiment 2

The polypeptide of embodiment 1, having at least 93%, at least 94%, at least 95%, at least 96%, at least 97%, at least 98%, at least 99% or 100% sequence identity to the mature polypeptide of SEQ ID NO: 21.

Embodiment 3

The polypeptide of any of embodiments 1-2, which is encoded by a polynucleotide having at least 96%, at least 97%, at least 98%, at least 99% or 100% sequence identity to the mature polypeptide coding sequence of SEQ ID NO: 20 or the cDNA sequence thereof.

Embodiment 4

The polypeptide of any of embodiments 1-3, comprising or consisting of SEQ ID NO: 21 or the mature polypeptide of SEQ ID NO: 21 shown as amino acids 19-1038 of SEQ ID NO: 21.

Embodiment 5

The polypeptide of embodiment 1, having at least 75%, at least, 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 23.

Embodiment 6

The polypeptide of embodiment 1, which is encoded by a polynucleotide having at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 22 or the cDNA sequence thereof.

Embodiment 7

The polypeptide of embodiment 1, comprising or consisting of SEQ ID NO: 23 or the mature polypeptide of SEQ ID NO: 23 shown as amino acids 21-1089 of SEQ ID NO: 23.

Embodiment 8

The polypeptides of any of the preceding embodiments, having a thermal denaturing temperature, Td, determined by TSA of at least 60° C., at least 61° C., at least 62° C., at least 63° C., at least 64° C., at least 65° C., at least 66° C., at least 67° C., such as at least 68° C.

Embodiment 9

A composition comprising the polypeptide of any of embodiments 1-8.

Embodiment 10

A whole broth formulation or cell culture composition comprising the polypeptide of any of embodiments 1-8.

Embodiment 11

A polynucleotide encoding the polypeptide of any of embodiments 1-8.

Embodiment 12

A nucleic acid construct or expression vector comprising the polynucleotide of embodiment 11 operably linked to one or more heterologous control sequences that direct the production of the polypeptide in an expression host.

Embodiment 13

A recombinant host cell comprising the nucleic acid construct embodiment 12.

Embodiment 14

The recombinant host cell of embodiment 13, wherein the cell is a yeast cell, particularly a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell, most particularly *Saccharomyces cerevisiae*.

Embodiment 15

A method of producing a polypeptide having trehalase activity, comprising cultivating the host cell of embodiment 13 or 14 under conditions conducive for production of the polypeptide.

Embodiment 16

The method of embodiment 15, further comprising recovering the polypeptide.

Embodiment 17

A process of producing a fermentation product, comprising
(a) liquefying a starch-containing material with an alpha-amylase;
optionally pre-saccharifying the liquefied material before step (b);
(b) saccharifying the liquefied material;
(c) fermenting using a fermentation organism;

wherein
i) a glucoamylase;
ii) a trehalase of any of embodiments 1-8;
iii) optionally a cellulolytic enzyme composition and/or a protease;
are present and/or added during
saccharification step (b);
fermentation step (c);
simultaneous saccharification and fermentation;
optionally presaccharification step before step (b).

Embodiment 18

The process of embodiment 17, wherein the alpha-amylase is a bacterial alpha-amylase, in particular of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 8 herein.

Embodiment 19

The process of embodiment 18, wherein the *Bacillus stearothermophilus* alpha-amylase or variant thereof is truncated, preferably to be from 485-495 amino acids long, such as around 491 amino acids long.

Embodiment 20

The process of any of embodiments 17-19, wherein the *Bacillus stearothermophilus* alpha-amylase has a double deletion at positions I181+G182, and optionally a N193F substitution, or deletion of R179+G180 (using SEQ ID NO: 8 for numbering).

Embodiment 21

The process of any of embodiments 17-20, wherein the *Bacillus stearothermophilus* alpha-amylase has a substitution in position S242, preferably a S242A, E or Q substitution (using SEQ ID NO: 8 for numbering).

Embodiment 22

The process of any of embodiments 17-21, wherein the *Bacillus stearothermophilus* alpha-amylase has a substitution in position E188, preferably E188P substitution (using SEQ ID NO: 8 for numbering).

Embodiment 23

The process of any of embodiments 17-22, wherein the alpha-amylase in liquefaction step (a) is selected from the following group of *Bacillus stearothermophilus* alpha-amylase variants:
I181*+G182*+N193F+E129V+K177L+R179E;
I181*+G182*+N193F+V59A+Q89R+E129V+K177L+R179E+H208Y+K220P+N224L+Q254S
I181*+G182*+N193F+V59A+Q89R+E129V+K177L+R179E+Q254S+M284V;
I181*+G182*+N193F+V59A+E129V+K177L+R179E+Q254S+M284V and
I181*+G182*+N193F+E129V+K177L+R179E+K220P+N224L+S242Q+Q254S (using SEQ ID NO: 8 herein for numbering).

Embodiment 24

The process of any of embodiments 17-23, wherein the glucoamylase is of fungal origin, preferably from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Gloeophyllum*, such as *G. serpiarium* or *G. trabeum*.

Embodiment 25

The process of any of embodiments 17-24, wherein the glucoamylase is derived from *Talaromyces emersonii*, such as the one shown in SEQ ID NO: 4 herein.

Embodiment 26

The process of any of embodiments 17-25, wherein the glucoamylase is selected from the group consisting of:
(i) a glucoamylase comprising the polypeptide of SEQ ID NO: 4 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 4 herein.

Embodiment 27

The process of any of embodiments 17-24, wherein the glucoamylase is derived from *Gloeophyllum* serpiarium, such as the one shown in SEQ ID NO: 5 herein.

Embodiment 28

The process embodiment 27, wherein the glucoamylase is selected from the group consisting of:
(i) a glucoamylase comprising the polypeptide of SEQ ID NO: 5 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 5 herein.

Embodiment 29

The process of any of embodiments 17-24, wherein the glucoamylase is derived from *Gloeophyllum trabeum* such as the one shown in SEQ ID NO: 6 herein.

Embodiment 30

The process of embodiment 29, wherein the glucoamylase present and/or added in saccharification is selected from the group consisting of:
(i) a glucoamylase comprising the polypeptide of SEQ ID NO: 6 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 herein.

Embodiment 31

The process of any of embodiments 17-30, further wherein an alpha-amylase is present and/or added during saccharification step (b); fermentation step (c); simultaneous saccharification and fermentation; or the optional presaccharification step before step (b).

Embodiment 32

The process of embodiment 31, wherein the alpha-amylase is of fungal or bacterial origin.

Embodiment 33

The process of embodiment 31 or 32, wherein the alpha-amylase is derived from a strain of the genus Rhizomucor, preferably a strain the Rhizomucor pusillus, such as the one shown in SEQ ID NO: 3 in WO 2013/006756, such as a Rhizomucor pusillus alpha-amylase hybrid having an Aspergillus niger linker and starch-bonding domain, such as the one shown in SEQ ID NO: 7 herein.

Embodiment 34

The process of any of embodiments 31-33, wherein the alpha-amylase present and/or added in saccharification and/or fermentation is selected from the group consisting of:
(i) an alpha-amylase comprising the polypeptide of SEQ ID NO: 7 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7 herein.

Embodiment 35

The process of any of embodiments 31-34, wherein the alpha-amylase is a variant of the alpha-amylase shown in SEQ ID NO: 7 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 7 for numbering).

Embodiment 36

The process of any of embodiments 33-35, wherein the alpha-amylase is derived from a Rhizomucor pusillus, in particular with an Aspergillus niger glucoamylase linker and starch-binding domain (SBD), preferably the one disclosed as SEQ ID NO: 7 herein, preferably having one or more of the following substitutions: G128D, D143N, preferably G128D+D143N (using SEQ ID NO: 7 for numbering).

Embodiment 37

The process of any of embodiments 35-36, wherein the alpha-amylase variant has at least 60% identity, such as at least 70%, preferably at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 7 herein.

Embodiment 38

The process of any of embodiments 17-37, wherein the cellulolytic enzyme composition is derived from Trichoderma reesei, Humicola insolens or Chrysosporium lucknowense.

Embodiment 39

The process of any of embodiments 17-38, wherein the cellulolytic enzyme composition comprises a beta-glucosidase, a cellobiohydrolase, an endoglucanase and optionally a GH61 polypeptide.

Embodiment 40

The process of any of embodiment 17-39, wherein the cellulolytic enzyme composition comprises a beta-glucosidase, preferably one derived from a strain of the genus Aspergillus, such as Aspergillus oryzae, such as the one disclosed in WO 2002/095014 or the fusion protein having beta-glucosidase activity disclosed in WO 2008/057637, or Aspergillus fumigatus, such as one disclosed in SEQ ID NO: 2 in WO 2005/047499 or SEQ ID NO: 14 herein or an Aspergillus fumigatus beta-glucosidase variant disclosed in WO 2012/044915; in particular an Aspergillus fumigatus beta-glucosidase variant with one or more, such as all, of the following substitutions: F100D, S283G, N456E, F512Y; or a strain of the genus a strain Penicillium, such as a strain of the Penicillium brasilianum disclosed in WO 2007/019442, or a strain of the genus Trichoderma, such as a strain of Trichoderma reesei.

Embodiment 41

The process of any of embodiments 17-40, wherein the cellulolytic enzyme composition comprises a cellobiohydrolase I (CBH I), such as one derived from a strain of the genus Aspergillus, such as a strain of Aspergillus fumigatus, such as the Cel7a CBH I disclosed in SEQ ID NO: 6 in WO 2011/057140 or SEQ ID NO: 17 herein, or a strain of the genus Trichoderma, such as a strain of Trichoderma reesei.

Embodiment 42

The process of any of embodiments 17-41, wherein the cellulolytic enzyme composition comprises a cellobiohydrolase II (CBH II, such as one derived from a strain of the genus Aspergillus, such as a strain of Aspergillus fumigatus; such as the one disclosed as SEQ ID NO: 18 herein or a strain of the genus Trichoderma, such as Trichoderma reesei, or a strain of the genus Thielavia, such as a strain of Thielavia terrestris, such as cellobiohydrolase II CEL6A from Thielavia terrestris.

Embodiment 43

The process of any of embodiments 17-42, wherein the cellulolytic enzyme composition further comprises a GH61 polypeptide having cellulolytic enhancing activity such as one derived from the genus Thermoascus, such as a strain of

*Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

Embodiment 44

The process of any of embodiments 17-43, wherein the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499) or SEQ ID NO: 14 herein.

Embodiment 45

The process of any of embodiments 17-44, wherein the cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 16 herein; and *Aspergillus fumigatus* beta-glucosidase (SEQ ID NO: 2 of WO 2005/047499 or SEQ ID NO: 14 herein) or a variant thereof with one or more, such as all, of the following substitutions: F100D, S283G, N456E, F512Y.

Embodiment 46

The process of any of embodiments 17-45, wherein the cellulolytic enzyme composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

Embodiment 47

The process of any of embodiments 17-46, wherein the presaccharification is carried out at a temperature from 40-75° C., such as 50-70° C., preferably 60° C.; a pH between 4-6, preferably 5; for a period of 30-360 minutes, such as from 60-420 minutes, such as around between 150-180 minutes.

Embodiment 48

A process of any of embodiments 17-47, comprising the steps of:
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase;
ii) a trehalase of any of embodiments 1-8;
are present and/or added during
saccharification step (b);
fermentation step (c);
simultaneous saccharification and fermentation;
optionally presaccharification step before step (b).

Embodiment 49

A process of any of embodiments 17-48, comprising the steps of:
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase from *Talaromyces emersonii* or *Gloeophyllum serpiarium*;
ii) a trehalase shown in any of embodiments 1-8;
are present and/or added during
saccharification step (b);
fermentation step (c);
simultaneous saccharification and fermentation;
optionally presaccharification step before step (b).

Embodiment 50

A process of any of embodiments 17-49, comprising the steps of:
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase from *Talaromyces emersonii* or *Gloeophyllum serpiarium*;
ii) a trehalase shown any of embodiments 1-8;
iii) a cellulolytic enzyme composition derived from *Trichoderma reesei*;
are present and/or added during
saccharification step (b);
fermentation step (c);
simultaneous saccharification and fermentation;
optionally presaccharification step before step (b).

Embodiment 51

The process of any of embodiments 17-50, wherein saccharification step (a) and fermentation step (b) are done separately or simultaneously.

Embodiment 52

The process of any of embodiments 17-51, wherein the fermentation product is recovered after fermentation.

Embodiment 53

The process of any of embodiments 17-52, wherein the starch-containing material is plant material selected from the corn (maize), cobs, wheat, barley, rye, milo, sago, cassava, tapioca, sorghum, rice, peas, beans, sweet potatoes, or a mixture thereof, preferably corn.

Embodiment 54

The process of any of embodiments 17-53, wherein the temperature in liquefaction is above the initial gelatinization temperature, in particular in the range from 70-1000C, such as between 75-95° C., such as between 75-90° C., preferably between 80-90° C., such as 82-88° C., such as around 85° C.

Embodiment 55

The process of any of embodiments 17-54, wherein liquefaction step (a) is carried out at a pH in the range between 3 and 7, preferably from 4 to 6, or more preferably from 4.5 to 5.5.

Embodiment 56

The process of any of embodiments 17-55, wherein the dry solid content (DS) in liquefaction lies in the range from 20-55 wt.-%, preferably 25-45 wt.-%, more preferably 30-40 wt.-% or 30-45 wt-%.

Embodiment 57

The process of any of embodiments 17-56, further comprises, prior to the liquefaction step (a), the steps of:
x) reducing the particle size of the starch-containing material, preferably by dry milling;
y) forming a slurry comprising the starch-containing material and water.

Embodiment 58

The process of any of embodiments 17-57, wherein a jet-cooking step is carried out prior to liquefaction in step (a).

Embodiment 59

The process of any of embodiments 17-58, wherein the starch-containing material is reduced in particle size, such as by dry milling or wet milling or using particle size emulsion technology.

Embodiment 60

The process of any of embodiments 17-59, wherein the fermentation is carried out for 30 to 150 hours, preferably 48 to 96 hours.

Embodiment 61

The process of any of embodiments 17-60, wherein the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

Embodiment 62

The process of any of embodiments 17-61, wherein further a protease is present during saccharification and/or fermentation.

Embodiment 63

The process of any of embodiments 17-62, wherein glucoamylase is present and/or added in an amount of 0.001 to 10 AGU/g DS, preferably from 0.01 to 5 AGU/g DS, especially 0.1 to 0.5 AGU/g DS.

Embodiment 64

The process of any of embodiments 17-63, wherein the fermentation product is an alcohol, preferably ethanol, especially fuel ethanol, potable ethanol and/or industrial ethanol.

Embodiment 65

The process of any of embodiments 17-64, further wherein a protease is present and/or added during
saccharification step (b);
fermentation step (c);
simultaneous saccharification and fermentation;
optionally presaccharification step before step (b).

Embodiment 66

The process of any of embodiments 17-65, wherein the protease is derived from *Thermoascus*, in particular *Thermoascus aurantiacus*, especially *Thermoascus aurantiacus* CGMCC No. 0670 (classified as EC 3.4.24.39) shown in SEQ ID NO: 13 herein.

Embodiment 67

The process of embodiment 66, wherein the protease is the one shown in SEQ ID NO: 13 herein or a protease being at least 60%, such as at least 70%, such as at least 80%, such as at least 90%, such as at least 95%, such as at least 96%, such as at least 97%, as as at least 98%, such as at least 99% identical to SEQ ID NO: 13 herein.

Embodiment 68

The process of any of embodiments 17-65, wherein the protease is derived from a strain of *Meripilus*, in particular *Meripilus giganteus*, in particular the one shown as SEQ ID NO: 19 herein.

Embodiment 69

The process of embodiment 68, wherein the protease is the one shown in SEQ ID NO: 19 herein or a protease being at least 60%, such as at least 70%, such as at least 80%, such as at least 90%, such as at least 95%, such as at least 96%, such as at least 97%, as as at least 98%, such as at least 99% identical to SEQ ID NO: 19 herein.

Embodiment 70

The process of any of embodiments 17-69, wherein the fermenting organism is derived from a strain of *Saccharomyces*, such as *Saccharomyces cerevisae*.

Embodiment 71

The process according to any of the embodiments 17-70, wherein the yeast fermenting organism expresses the trehalse according to embodiments 1-8.

Embodiment 72

A process of producing fermentation products from starch-containing material comprising:
 (i) saccharifying a starch-containing material at a temperature below the initial gelatinization temperature; and
 (ii) fermenting using a fermentation organism;
 wherein saccharification and/or fermentation is done in the presence of the following enzymes: glucoamylase, alpha-amylase, trehalase of any of embodiments 1-8, and optionally a protease and/or a cellulolytic enzyme composition.

Embodiment 73

A process of producing a fermentation product from pretreated cellulosic material, comprising:
 (a) hydrolyzing said pretreated cellulosic material with a cellulolytic enzyme composition;
 (b) fermenting using a fermenting organism; and
 (c) optionally recovering the fermentation product,
 wherein a trehalase of any of embodiments 1-8 is added and/or present in hydrolysis step (a) and/or fermentation step (b).

Embodiment 74

The process of any of embodiments 17-73, wherein the trehalase is added in an amount between 0.01-20 ug EP trehalase/g DS, such as between 0.05-15 ug EP terhalase/g DS, such as between 0.5 and 10 ug EP trehalase/g DS.

Embodiment 75

The process of any of embodiments 17-74, wherein the cellulolytic enzyme composition is derived from *Trichoderma reesei*, *Humicola insolens* or *Chrysosporium lucknowense*.

Embodiment 76

The process of any of embodiments 72-75, wherein the cellulolytic enzyme composition comprising a beta-glucosidase, a cellobiohydrolase, an endoglucanase and optionally a GH61 polypeptide.

Embodiment 77

The process of any of embodiment 72-76, wherein the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 14 herein or an *Aspergillus fumigatus* beta-glucosidase variant disclosed in WO 2012/044915; in particular an *Aspergillus fumigatus* beta-glucosidase variant with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

Embodiment 78

The process of any of embodiments 72-77, wherein the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 17 herein, or a strain of the genus *Trichoderma*, such as a strain of *Trichoderma reesei*.

Embodiment 79

The process of any of embodiments 72-78, wherein the cellulolytic enzyme composition comprises a cellobiohydrolase II (CBH II, such as one derived from a strain of the genus *Aspergillus*, such as a strain of *Aspergillus fumigatus*; such as the one disclosed as SEQ ID NO: 18 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Embodiment 80

The process of any of embodiments 72-79, wherein the cellulolytic enzyme composition further comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

Embodiment 81

The process of any of embodiments 72-80, wherein the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499) or SEQ ID NO: 14 herein.

Embodiment 82

The process of any of embodiments 72-81, wherein the cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 16 herein; and *Aspergillus fumigatus* beta-glucosidase (SEQ ID NO: 2 of WO 2005/047499 or SEQ ID NO: 14 herein) or a variant thereof with one or more, such as all, of the following substitutions: F100D, S283G, N456E, F512Y.

Embodiment 83

The process of any of embodiments 72-82, wherein the cellulolytic enzyme composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

The present invention is further described by the following examples.

EXAMPLES

Materials & Methods
Enzymes and Yeast Used:
Alpha-Amylase BE369 (AA369):

Bacillus stearothermophilus alpha-amylase disclosed herein as SEQ ID NO: 8, and further having the mutations: I181*+G182*+N193F+V59A+Q89R+E129V+K177L+ R179E+Q254S+M284V truncated to 491 amino acids (using SEQ ID NO: 8 for numbering).

Protease PfuS shown in SEQ ID NO: 9 herein.
Glucoamylase X:

Blend comprising Talaromyces emersonii glucoamylase disclosed as SEQ ID NO: 34 in WO99/28448 (SEQ ID NO: 4 herein), Trametes cingulata glucoamylase disclosed as SEQ ID NO: 2 in WO 06/69289 (SEQ ID NO: 11 herein), and Rhizomucor pusillus alpha-amylase with Aspergillus niger glucoamylase linker and starch binding domain (SBD) disclosed in SEQ ID NO: 7 herein having the following substitutions G128D+D143N using SEQ ID NO: 7 for numbering (activity ratio in AGU:AGU:FAU-F is about 29:8:1).

Yeast: Ethanol Red®
Trehalase Assay:
Principle:

$$\text{Trehalose} + H_2O \xrightarrow{Trehalase} 2 \text{ Glucose}$$

T=37° C., pH=5.7, A340 nm, Light path=1 cm
Spectrophotometric Stop Rate Determination
Unit Definition:

One unit will convert 1.0 mmole of trehalose to 2.0 mmoles of glucose per minute at pH 5.7 at 37° C. (liberated glucose determined at pH 7.5).

(See Dahlqvist, A. (1968) Analytical Biochemistry 22, 99-107)
Trehalase Assay Used in Example 3.

Ten microliters of sample was mixed with 190 µl of substrate solution (1% trehalose in 50 mM sodium acetate, pH 4.3) and incubate at 32° C. for 1 hour. 10 µl of the solution was then taken out and 200 µl of glucose CII test WAKO was added. A505 was measured after 15 min-incubation at room temperature.

Strains

An improved Aspergillus oryzae host/vector system comparable to the one described in example 5 disclosed in WO 2016026938A1 was constructed. The improvement was made to reduce the size of the transforming DNA by moving the FLPase expression cassette located on PART-II of the plasmid pDAu724 (see page 34, FIG. 7 and SEQ ID NO:30 in WO 2016026938A1) to the integration locus amy2 in the genome of the host strain. The cloning of the FLPase expression cassette into pDAu703 (WO 2016026938A1 page 32 and FIG. 6 and SEQ ID:29) was done by amplification of the FLPase expression cassette from pDAu724 and cloning in between FRT-F3 and the amdS selection marker of pDAu703 to give the plasmid pDAu770. The same protocol as described in WO 2016026938A1 page 33 was used to transform the linearized plasmid pDAu770 into protoplasts of A. oryzae strain Ja11338 (disclosed in WO12160097A1). Transformants were selected on AmdS selection plates to obtain strain DAu785. The resulting recombinant host strain DAu785 has a modified amy2 locus comparable to the one in DAU716 (WO 2016026938A1) with the addition of the FLPase expression cassette. The host strain DAu785 is constitutively expressing the FLPase site specific recombinase allowing the integration at the FRT sites of the transforming DNA in this case the PCR fragments obtained by Overlap Extension PCR reaction described below. This strain was used for heterologous expression of the trehalase polypeptides SEQ ID NO: 21, and SEQ ID NO: 23.

Talaromyces funiculosus NRRL 1035 was kindly obtained in February 1992 from Pr. Jens Frisvad (Denmark Technical University, Department of Biotechnology and Biomedicine). T. funiculosus was originally isolated by George Smith in England in 1936. The strain was inoculated onto a PDA plate and incubated for 8 days at 26° C. in the darkness. Several mycelia-PDA plugs were inoculated into 500 ml shake flasks containing 100 ml of YPG medium. The shake flasks were incubated for 5 days at 26° C. with shaking at 100 rpm for production of biomass.

Talaromyces leycettanus reference CBS 398.68 (isolated in 1968 in England) was purchased from CBS-KNAW Fungal Biodiversity Centre, Uppsalalaan 8, 3584 CT, Utrecht, The Netherlands and inoculated onto a PDA plate and incubated for 8 days at 26° C. in the darkness. Several mycelia-PDA plugs were inoculated into 500 ml shake flasks containing 100 ml of YPG medium. The flasks were incubated for 5 days at 26° C. with shaking at 100 rpm for production of biomass.

Media and Solutions

PDA plates were composed of 39 g Potato Dextrose Agar (ref. 70139) (Sigma-Aldrich, Munich, Germany) and deionized water to 1000 ml. The medium was sterilized by autoclaving at 15 psi for 15 minutes (Bacteriological Analytical Manual, 8th Edition, Revision A, 1998).

LB-Bouillon was composed of 25 g of LB Bouillon (ref. L3152) (Sigma-Aldrich, Munich, Germany) and deionised water to 1000 ml. The medium was sterilized by autoclaving at 15 psi for 15 minutes (Bacteriological Analytical Manual, 8th Edition, Revision A, 1998).

Ampicillin LB-agar was composed of 37 g LB agar (ref. L3027) (Sigma-Aldrich, Munich, Germany), 5 g soluble starch, 0.01 M K2PO4, 0.04% glucose, and deionised water to 1000 ml. The medium was sterilized by autoclaving at 15 psi for 15 minutes (Bacteriological Analytical Manual, 8th Edition, Revision A, 1998). Medium was cooled to 50° C. and 50 mM ampicillin was added.

COVE-N-agar plates were composed of 218 g of sorbitol, 25 g of agar powder, 50 ml of COVE salt solution, and deionized water to 1000 ml. The medium was sterilized by autoclaving at 15 psi for 15 minutes (Bacteriological Analytical Manual, 8th Edition, Revision A, 1998). The medium was cooled to 50° C. and 10 mM acetamide, and Triton X-100 (50 µl/500 ml) were added.

Sucrose Agar 10 mM NaNO3 was composed of 342 g sucrose, 20 g agar powder, 20 ml COVE salt solution, and deionized water to 1000 ml. The medium was sterilized by autoclaving at 15 psi for 15 minutes (Bacteriological Analytical Manual, 8th Edition, Revision A, 1998). The medium was cooled to 50° C. and 10 mM NaNO3, and Triton X-100 (50 µl/500 ml) were added.

COVE salt solution was composed of 26 g of MgSO4.7H2O, 26 g of KCL, 76 g of KH2PO4, 50 ml of COVE trace metal solution, and deionized water to 1000 ml. Solution was sterile filtered.

COVE trace metal solution was composed of 0.04 g of Na2B4O7.10H2O, 0.4 g of CuSO4.5H2O, 1.2 g of FeSO4.7H2O, 0.7 g of MnSO4.H2O, 0.8 g of Na2MoO4.2H2O, 10 g of ZnSO4.7H2O, and deionized water to 1000 ml. Solution was sterile filtered.

DAP4C-1 medium was composed of 0.5 g yeast extract, 10 g maltose, 20 g dextrose, 11 g MgSO4.7H2O, 1 g KH2PO4, 2 g C6H8O7.H2O, 5.2 g K3PO4.H2O, 1 ml Dowfax 63N10 (antifoaming agent), 2.5 g calcium carbonate, supplemented with 0.5 ml KU6 trace metal solution, and deionised water to 1000 ml. The medium was sterilized by autoclaving at 15 psi for 15 minutes (Bacteriological Analytical Manual, 8th Edition, Revision A, 1998). Before use, 3.5 ml of sterile 50% (NH4)2HPO4 and 5 ml of sterile 20% lactic acid were added per 150 ml of DAP4C-1 medium.

MDU-2 medium was composed of 45 g maltose, 1 g MgSO4.7H2O, 1 g NaCl, 2 g K2SO4, 12 g KH2PO4, 0.5 ml KU6 trace metal, 0.1 ml Dowfax63N10 (antifoaming agent), and deionised water to 1000 ml. pH was adjusted to pH5 and the medium was sterilized by autoclaving at 15 psi for 15 minutes (Bacteriological Analytical Manual, 8th Edition, Revision A, 1998). 15 ml 50% sterile filtered urea was added after autoclaving.

YP2% glucose was composed of 10 g yeast extract, 20 g Bacto peptone, 20 g dextrose, and deionized water to 1000 ml. The medium was sterilized by autoclaving at 15 psi for 15 minutes (Bacteriological Analytical Manual, 8th Edition, Revision A, 1998).

KU6 trace metal solution was composed of 6.8 g ZnCl2, 2.5 g CuSO4.5H2O, 0.13 g NiCl2, 13.9 g FeSO4.7H2O, 8.45 g MnSO4.H2O, 3 g C6H8O7.H2O, and deionised water to 1000 ml. Solution was sterile filtered.

Example 1: Cloning of Trehalase Sequence

*Talaromyces* DNA sequences were PCR amplified from gDNA from *Talaromyces funiculosus* and *Talaromyces leycettanus* and cloned by overlap-extension PCR. pDAu724 plasmid (see Strain section above) was used as DNA template to amplify two PCR products (F1 and F3) in reactions composed of 10 µl of KAPA polymerase buffer 5×, 1 µl 10 mM KAPA PCR Nucleotide Mix, 1 µl of 10 µM of the appropriate forward primers (SEQ ID NO: 24 for F1 and SEQ ID NO: 26 for F3), 1 µl of 10 µM of the appropriate reverse primers (SEQ ID NO: 25 for F1 and SEQ ID NO: 27 for F3), 1 to 10 ng of pDAu724 plasmid, 1 µl of KAPA Biosystems polymerase KK2502 (1 unit) and PCR-grade water up to 50 µL. PCR amplification reactions were carried out on a DYAD® Dual-Block Thermal Cycler (MJ Research Inc., Waltham, Mass., USA) programmed for 2 min. at 98° C. and followed by 35 cycles of 10 sec. at 98° C. and 2 min. at 72° C. and one final cycle of 10 min. at 72° C. Five µl of the PCR reaction were analysed by 1% agarose gel electrophoresis using TAE buffer where DNA bands of the appropriate size were observed. The remaining PCR reactions were purified using an ILLUSTRA™ GFX™ PCR DNA and Gel Band Purification Kit according to the manufacturer's instructions.

Overlap Extension PCR reactions for cloning trehalase genes amplified from *Talaromyces funiculosus*, and *Talaromyces leycettanus* respectively were composed of 10 µl KAPA polymerase buffer (5×), 1 µl 10 mM KAPA PCR Nucleotide Mix, 50 ng of PCR fragment F1 and equimolar amounts of PCR fragment F3 and trehalase genes encoding for SEQ ID NO: 21, or SEQ ID NO: 23, 1 µl KAPA Biosystems polymerase KK2502 (1 unit) and PCR-grade water up to 48 µL. Reactions were incubated on a DYAD® Dual-Block Thermal Cycler (MJ Research Inc., Waltham, Mass., USA) using a program composed of 2 min. at 98° C., followed by 5 cycles each composed of 10 sec. at 98° C., 30 sec. at 68° C., and 5 min. at 72° C. and completed by a final extension of 8 min. at 72° C. During the Overlap Extention PCR reactions, annealing between fragment F1 and trehalase genes encoding for SEQ ID NO: 21, and SEQ ID NO: 23 was ensured by overlap sequence SEQ ID NO: 28 included in the forward cloning primers (SEQ ID NO: 31 and SEQ ID NO: 30). Annealing between fragment F3 and the trehalase genes encoding for SEQ ID NO: 21, SEQ ID NO: 23 was ensured by the overlap sequence SEQ ID NO: 29 included in the reverse cloning primers (SEQ ID NO: 33 and SEQ ID NO: 32). One µl of 10 µM primer SEQ ID NO: 24 and 1 µl of 10 µM primer SEQ ID NO: 27 were added to the Overlap Extention PCR reactions after the five initial cycles and the reactions were incubated a second time on a DYAD® Dual-Block Thermal Cycler (MJ Research Inc., Waltham, Mass., USA) using a program composed of 2 min. at 98° C.; followed by 25 cycles each composed of 10 sec. at 98° C., and 4 min. at 72° C. and completed by a final extension of 10 min. at 72° C. The PCR reactions resulted in two products: SEQ ID NO: 20 and SEQ ID NO: 22. Five µl of the PCR reactions were analysed by 1% agarose gel electrophoresis using TAE buffer where an DNA bands of the appropriate size were observed. The remaining PCR reactions were up-concentrated to 20 µl by heating the tubes at 60° C. Ten µl of those reactions were used for *Aspergillus oryzae* DAu785 protoplasts transformation.

Example 2: Heterologous Expression of Trehalases

Protoplasts of *Aspergillus oryzae* DAu785 strain were prepared according to WO 95/002043. 100 µl of *A. oryzae* protoplasts were mixed with 10 µl of up-concentrated Overlap Extention PCR encoding for *Talaromyces funiculosus*, and *Talaromyces leycettanus* trehalases polypeptide (amino acids 19-1038 of SEQ ID NO: 21 and amino acids 21-1089 of SEQ ID NO: 23), and 270 µl of 60% PEG 4000 (Applichem, Darmstadt, Germany) (polyethylene glycol, molecular weight 4,000), 10 mM CaCl2), and 10 mM Tris-HCl pH 7.5 and gently mixed. The mixture was incubated at 37° C. for 30 minutes and the protoplasts were spread onto Sucrose Agar plates containing 10 mM NaNO3. After incubation for 4-7 days at 37° C., spores of eight colonies were inoculated into MDU-2 medium in 96-well X50 microtiter plate PS from ThermoFisher (Life Technologies Europe BV, Naerum, Denmark) and covered with semi-permeable tape. After 4 days of static incubation at 30° C., the culture broths were analysed by sodium dodecyl sulfate polyacrylamide gel electrophoresis to identify colonies producing the highest amount of trehalase polypeptides. Spores of the best transformant were spread onto Sucrose Agar plates containing 0.01% TRITON® X-100 and 10 mM NaNO3 to isolate single colonies. The spreading was repeated twice.

Example 3: Characterization of Trehalases of the Invention

| Trehalases | Organism | GH |
| --- | --- | --- |
| Ms-trehalase | *Myceliophthora sepedonium* | 37 |
| Tr-trehalase | *Trichoderma reesei* | 65 |
| An-trehalase | *Aspergillus niger* | 65 |

| Trehalases | Organism | GH |
|---|---|---|
| Tl-trehalase | *Talaromyces leycettanus* | 65 |
| Tf-trehalase | *Talaromyces funiculosus* | 65 |

Purification

Purification of trehalase enzymes were carried out by two steps, desalting column and cation exchange chromatography column. Finally, the sample was dialyzed against 10 L of 20 mM sodium acetate buffer (pH 4.0) using 12 k-14 k MWCO (molecular weight-cutoff) dialysis membrane and then concentrated using 30 k MWCO centrifugal filter unit.

Thermostability Determination (TSA)

Purified enzyme was diluted to 0.5 mg/ml with 50 mM sodium acetate buffer (pH 4.5) and mixed with equal volume of SYPRO Orange (Invitrogen) diluted with Milli-Q water. Eighteen microliters of mixture solution was transfer to LightCycler 480 Multiwell Plate 384 (Roche Diagnostics) and the plate was sealed.

Equipment Parameters of TSA:

Apparatus: LightCycler 480 Real-Time PCR System (Roche Applied Science)

Scan rate: 0.02° C./sec

Scan range: 37-96° C.

Integration time: 1.0 sec

Excitation wave length 465 nm

Emission wave length 580 nm

The obtained fluorescence signal was normalized into a range of 0 and 1. The denaturing temperature (Td) was defined as the temperature where the normalized value is closest to 0.5. The temperature where the maximum signal intensity (normalized value is 1) was defined as Td2 and it used for an index of thermostability of M-tre PE variants.

Trehalase Assay

Ten microliters of sample was mixed with 190 µl of substrate solution (1% trehalose in 50 mM sodium acetate, pH 4.3) and incubate at 32° C. for 1 hour. 10 µl of the solution was then taken out and 200 µl of glucose CII test WAKO was added. A505 was measured after 15 min-incubation at room temperature.

SF Cultivation for Protease Cocktail Preparation

*Aspergillus niger* strains used to prepare protease cocktail is derivatives of NN059095, which was isolated by Novozymes and genetically modified to disrupt expression of amyloglycosidase activities from *Aspergillus niger* NN049184 isolated from soil.

Spores of *Aspergillus niger* strains were inoculated in 100 ml MLC media and cultivated at 30° C. for 2 days. 10 ml of MLC was inoculated to 100 ml of MU-1 medium and cultivated at 30° C. for 7 days. The supernatant was obtained by centrifugation.

MLC is composed of 40 g glucose, 50 g soybean powder, 4 g citric acid (pH 5) and water to 1 liter.

MU-1-glu is composed of 260 g glucose, 3 g $MgSO_4$-$7H_2O$, 5 g $KH_2PO_4$, 6 g $K_2SO_4$, 0.5 ml of trace metal solution and 2 g urea (pH 4.5) and water to 1 liter.

Trace metal solution is composed of 6.8 g $ZnCl_2$-$7H_2O$, 2.5 g $CuSO_4.5H_2O$, 0.24 g $NiCl_2'6H_2O$, 13.9 g $FeSO_4.7H_2O$, 13.5 g $MnSO_4$—$H_2O$ and 3 g citric acid and water to 1 liter.

Protease Stability Assay

Purified enzyme was diluted to 2 mg/ml with 50 mM sodium acetate buffer pH 4.0 and 100 µl of the sample was mixed with 100 µl of prepared protease cocktail. The solution was then incubated at −20, 4, 30 and 40° C. for 3 days and the residual activity was measured by trehalase assay.

Results

| Trehalases | Td [° C.] | Protease stability* 4° C. | 30° C. | 40° C. |
|---|---|---|---|---|
| Ms-trehalase SEQ ID NO: 1 | 56.9 | 90% | 42% | 15% |
| Tr-trehalase SEQ ID NO: 2 | 57.9 | 100% | 100% | 100% |
| An-trehalase SEQ ID NO: 3 | 53.1 | 100% | 97% | 68% |
| Tl-trehalase SEQ ID NO: 23 | 69.0 | 100% | 100% | 100% |
| Tf-trehalase SEQ ID NO: 21 | 65.2 | 100% | 100% | 100% |

*Residual activity after 3 days-incubation in an admixture with protease cocktail (−20° C. as 100%)

Example 4: Thermo-Stability of the Trehalases According to the Invention Compared to Two Prior Art Trehalases Thermo-stability of the trehalases of the invention, disclosed herein as SEQ ID NO: 21 and SEQ ID NO: 23, where compared to two prior art trehalses; one from *Talaromyces cellulolyticus* (SEQ ID NO: 34) (Fujii T, Hoshino T, Inoue H, Yano S. 2014. Taxonomic revision of the cellulose-degrading fungus *Acremonium cellulolyticus* nomen *nudum* to *Talaromyces* based on phylogenetic analysis. FEMS Microbiology Letters. 351: 32-41) and one from *Talaromyces verruculosus* (SEQ ID NO: 35) (published in 2015 as part of a genome sequence on the NCBI website as assembly GCA 001305275.1; polypeptide identified as EFP5BRM8N). The thermo-stability was measured as denaturing temperature using a Thermal Shift Assay (TSA).

Samples

| Trehalase | Organism |
|---|---|
| EXP13116 (SEQ ID NO: 34) | *Talaromyces celluloyticus* |
| EXP13117 (SEQ ID NO: 35) | *Talaromyces verruculosus* |
| Tl-trehalase (SEQ ID NO: 23) | *Talaromyces leycettanus* |
| Tf-trehalase (SEQ ID NO: 21) | *Talaromyces funiculosus* |

Strain Cultivation

Agar pieces of a strain cultivated onto COVE N-gly agar plate for 1 week at 30° C. were inoculated to 100 ml of MS9 in a 500 ml shaking flask and it was cultivated at 30° C. for 1 day with shaking at 220 rpm. Three ml of the seed culture was transferred to 100 ml of MDU-2BP-FuPE in 500 ml shaking flask and it was cultivated at 30° C. for 3 days with shaking at 220 rpm. The culture supernatant was filtrated with 0.2 µm cellulose acetate filter. Media components are described below.

COVE Nqly Aqar 218 g/L Sorbitol, 10 g/L Glycerol, 2.02 g/L Potassium Nitrate, 50 ml/L salt solution for COVE, pH 5.3

Salt Solution for COVE 26 g/L Potassium Chloride, 26 g/L Magnesium Sulfate Heptahydrate, 76 g/L Potassium Dihydrogenphosphate, 50 ml/L Trace metal solution for COVE Trace Metal Solution for COVE 0.04 g/L Sodium Tetraborate Decahydrate, 0.4 g/L Copper (II) Sulfate Pentahydrate, 1.2 g/L Iron(II) Sulfate Heptahydrate, 1 g/L Manganese(II) Sulfate Pentahydrate, 0.8 g/L Sodium molybdate dihydrate, 10 g/L Zinc Sulfate Heptahydrate

MS9

30 g/L Soybean powder, 20 g/L Glycerol

MDU-2BP FuPE 45 g/L Maltodextrin, 7 g/L Yeast extract, 1 g/L Magnesium Sulfate Heptahydrate, 1 g/L Sodium Chloride, 2 g/L Potassium Sulfate, 0.75 g/L Ammonium Chloride, 12 g/L Potassium Dihydrogenphosphate, 0.5 ml/L Trace metal solution for AMG (MU-1)

Trace Metal Solution for AMG (MU-1)

1.39% Iron (II) Sulfate Heptahydrate, 1.356% Manganese (II) Sulfate Pentahydrate, 0.68% Zinc Chloride, 0.25% Copper(II) Sulfate Pentahydrate, 0.024 g/L Nickel (II) Chloride Hexahydrate, 0.3% Citric acid Purification Purification of WT trehalases were carried out by two steps, desalting column and cation exchange chromatography column. Finally, the sample was dialyzed against 10 L of 20 mM sodium acetate buffer (pH 4.0) using 12 k-14 k MWCO dialysis membrane and then concentrated using 30 k MWCO centrifugal filter unit.

Thermostability Determination (TSA)

Purified enzyme was diluted to 0.5 mg/ml with 50 mM sodium acetate buffer (pH 4.5) and mixed with equal volume of SYPRO Orange (Invitrogen) diluted with Milli-Q water. Eighteen microliters of mixture solution was transfer to LightCycler 480 Multiwell Plate 384 (Roche Diagnostics) and the plate was sealed.

Equipment Parameters of TSA

Apparatus: LightCycler 480 Real-Time PCR System (Roche Applied Science)

Scan rate: 0.02° C./sec

Scan range: 37-96° C.

Integration time: 1.0 sec

Excitation wave length 465 nm

Emission wave length 580 nm

The obtained fluorescence signal was normalized into a range of 0 and 1. The denaturing temperature (Td) was defined as the temperature where the normalized value is closest to 0.5. Td are listed in TABLE 1.

TABLE 1

| List of Td | |
| --- | --- |
| Trehalase | Td [° C.] |
| EXP13116 | 51.7 |
| EXP13117 | 47.1 |

TABLE 1-continued

| List of Td | |
| --- | --- |
| Trehalase | Td [° C.] |
| Tl-trehalase | 67.5 |
| Tf-trehalase | 64.7 |

Example 5: Use of Tf-Trehalase of the Invention in a Process for Producing Ethanol Enzymes and Yeast Used:

Alpha-Amylase BE369 (AA369):

*Bacillus stearothermophilus* alpha-amylase disclosed herein as SEQ ID NO: 8, and further having the mutations: I181*+G182*+N193F+V59A+Q89R+E129V+K177L+R179E+Q254S+M284V truncated to 491 amino acids (using SEQ ID NO: 8 for numbering).

Protease PfuS shown in SEQ ID NO: 9 herein.

Glucoamylase X:

Blend comprising *Talaromyces emersonii* glucoamylase disclosed as SEQ ID NO: 34 in WO99/28448 (SEQ ID NO: 4 herein), *Trametes cingulata* glucoamylase disclosed as SEQ ID NO: 2 in WO 06/69289 (SEQ ID NO: 11 herein), and *Rhizomucor pusillus* alpha-amylase with *Aspergillus niger* glucoamylase linker and starch binding domain (SBD) disclosed in SEQ ID NO: 7 herein having the following substitutions G128D+D143N using SEQ ID NO: 7 for numbering (activity ratio in AGU:AGU:FAU-F is about 29:8:1).

Yeast: Ethanol Red®

The ability of trehalase to reduce trehalose was evaluated by running a saccharification and fermentation (SSF) using either Glucoamylase blend X alone or with the addition of either Ms or Tf trehalase. The Ms trehalase dose was set at 1 μg enzyme protein (EP) per gram of dry solids (DS) while three Tf trehalose doses were used for comparison (0.6, 0.7 and 0.8 ug EP/g DS). Glucoamylase blend X were dosed at 0.6 AGU/g DS and in according to the following calculation. Two plant mashes (corn starch liquefied using alpha-amylase BE369 or BE369 and protease PfuS) were used. Mash 1 represented BE369+PfuS and Mash 2 represented BE369 mash. For Mash 1 BE369 and PfuS were dosed at 2.3 μg EP/g DS and 2.6 μg EP/g DS, respectively. For Mash 2 BE369 dose was 2.81 μg EP/g DS. The urea dose for Mash 1 and Mash 2 were 400 ppm and 1000 ppm, respectively.

$$\text{Enz. dose } (uL) = \frac{\text{Total GA dose}\left(\frac{AGU}{g\ DS}\right) \times \text{Mass Weight (g)} \times \text{Dry solid content (\% DS)} \times 1000}{\text{Stock enzyme conc.}\left(\frac{AGU}{mL}\right)}$$

TABLE 2

Enzyme treatment in SSF of two industrial plant mashes

| Glucoamylase | Trehalase treatment | Trehalase Dose (ug EP/g DS) |
|---|---|---|
| Blend X | None | 0 |
| Blend X | Ms-trehalase | 1 |
| Blend X | Tf-trehalase | 0.6 |
| Blend X | Tf-trehalase | 0.7 |
| Blend X | Tf-trehalase | 0.8 |

The blends were evaluated in an SSF using two liquefied industrial plant corn mashes Mash 1 and Mash 2. The mashes were supplemented with 3 ppm penicillin. The amount of urea added to Mash 1 and Mash 2 were 400 ppm and 1000 ppm, respectively. The pH of both plant mashes was adjusted to pH 5.1 using 40% $H_2SO_4$ prior to dispensing mash into flasks. Approximately 60 g (55±0.03) of mash was added into each 125 mL and they were run in duplicates. Corning Disposable Erlenmeyer flask that had a 0.048" hole on the cap for venting. Each flask was dosed with enzymes according to Table 2 and 1.2 mL of rehydrated Ethanol Red yeast. Ethanol red was rehydrated by resuspending 5.5 g yeast with 100 mL tap water and incubated at 32° C. for 30-40 min. Flasks were incubated for the total of 52 hr at 32° C. while shaking at 120 rpm. Samples were collected at 52 hrs. Collected samples were prepared for HPLC by removing approximately 4 grams of fermentation sample and mixed it with 40 uL of 40% $H_2SO_4$. The mixture was centrifuged for 10 minutes at 3500×g, and the supernatant was filtered through 0.2 μM Whatman nylon filter. Filtered samples were analyzed on an Agilent HPLC 1100/1200 series with Chemstation software. Samples were separated on Bio-Rad HPX-87H Ion Exclusion column (300 mm×7.8 mm) with a cation H guard cartridge. The mobile phase, 5 mM $H_2SO_4$, was run at 0.8 ml/min at 65° C. and the RI detector temperature was set at 55° C. The method quantifies several analytes using calibration standards (4 point calibration with forced through zero) for dextrins (DP4+), maltotriose (DP3), maltose (DP2), glucose (DP1), fructose, acetic acid, lactic acid, glycerol and ethanol. HPLC results on ethanol, DP2 (maltose) are shown in Table 3. DP2 was analyzed since this sugar also contain the trehalose. In addition to the HPLC analysis, filtered samples of only Mash 1 were also analyzed on a Dionex ICS-3000 ion chromatography (IC) using Chromeleon 5 software to separate trehalose from other DP2 sugars (such as isomaltose, maltose and cellobiose). Samples were separated using the Carbopack PA1 column. The mobile phase were water, 0.2 M NaOH, 1 M sodium acetate and the flowrate was 1 mL/min and both the column and detector (PAD detector with disposable gold electrode) were at 30° C. The IC was run for 65 minutes and the trehalose level were reported in Table 4. Tf-trehalase has slightly better performance than Ms-trehalase since 0.6-0.8 ug EP of Tf had similar level of DP2 following SSF for 52 hrs. Without any trehalase addition, there were significant amount of DP2 left at the end of fermentation. The ethanol levels were compared between Ms and Tf-trehalase treatment in both plant mashes and there was no statistical significance between them. Therefore, Tf-trehalase, at 20% to 40% lower protein dose relative to Ms-trehalase, has similar application performance as Ms-trehalase in SSF using two different types of plant mash.

TABLE 3

Ethanol, and DP2 levels following SSF in two plant mashes for 52 Hrs

| Gluco-amylase | Trehalase | Trehalase dose (μg EP/g DS) | Average ethanol level (% w/v) Mash 1 | Average ethanol level (% w/v) Mash 2 | Average DP2 level (% w/v) Mash 1 | Average DP2 level (% w/v) Mash 2 |
|---|---|---|---|---|---|---|
| Blend X | None |   | 13.517 | 13.0545 | 0.2405 | 0.1785 |
|   | Ms-trehalase | 1 | 13.590 | 13.080 | 0.141 | 0.110 |
|   | Tf-trehalase | 0.6 | 13.622 | 13.101 | 0.140 | 0.109 |
|   | Tf-trehalase | 0.7 | 13.608 | 13.122 | 0.139 | 0.106 |
|   | Tf-trehalase | 0.8 | 13.612 | 13.151 | 0.141 | 0.111 |

TABLE 4

Trehalose levels following SSF in two plant mashes for 52 Hrs

| Glucoamylase | Trehalase | Trehalase dose (μg EP/g DS) | Average trehalose level (% w/v) Mash 1 | Average trehalose level (% w/v) Mash 2 |
|---|---|---|---|---|
| Blend X | None |   | 0.0661 | n/a |
|   | Ms-trehalase | 1 | 0.0134 | n/a |
|   | Tf-trehalase | 0.6 | 0.0150 | n/a |
|   | Tf-trehalase | 0.7 | 0.0147 | n/a |
|   | Tf-trehalase | 0.8 | 0.0151 | n/a |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A process of producing a fermentation product, comprising (a) liquefying a starch-containing material with an alpha-amylase;
   optionally presaccharifying the liquefied material before step (b);
   (b) saccharifying the liquefied material;
   (c) fermenting using a fermentation microorganism; wherein
   i) a glucoamylase; and
   ii) a polypeptide having trehalase activity selected from the group consisting of a polypeptide having at least 93% sequence identity to the mature polypeptide of SEQ ID NO: 21 and a polypeptide encoded by a polynucleotide having at least 95% sequence identity to the mature polypeptide coding sequence of SEQ ID NO: 20 or the cDNA sequence thereof; and
   iii) optionally a cellulolytic enzyme composition, a protease, or both a cellulolytic enzyme composition and a protease are present or added during
   the saccharification step (b);
   the fermentation step (c); or
   the optionally presaccharification step before step (b).

2. The process of claim 1, wherein an alpha-amylase is present and/or added during saccharification step (b); fermentation step (c); or the optional presaccharification step before step (b).

3. The process of claim 1, wherein the alpha-amylase is the one disclosed as SEQ ID NO: 7, having one or more of the following substitutions: G128D, D143N, or G128D+D143N (using SEQ ID NO: 7 for numbering), and wherein the alpha-amylase variant has at least 80%, but less than 100% identity to the mature part of the polypeptide of SEQ ID NO: 7.

4. The process of claim 1, wherein the fermenting microorganism is derived from a strain of *Saccharomyces*.

5. The process according to claim 4, wherein the yeast fermenting organism expresses the polypeptide having trehalase activity.

6. A process of producing fermentation products from starch-containing material comprising:
   (i) saccharifying a starch-containing material at a temperature below the initial gelatinization temperature; and
   (ii) fermenting using a fermentation microorganism;
   wherein saccharification, fermentation, or saccharification and fermentation is done in the presence of the following enzymes:
   a. glucoamylase;
   b. alpha-amylase; and
   c. a polypeptide having trehalase activity selected from the group consisting of a polypeptide having at least 93% sequence identity to the mature polypeptide of SEQ ID NO: 21 and a polypeptide encoded by a polynucleotide having at least 95% sequence identity to the mature polypeptide coding sequence of SEQ ID NO: 20 or the cDNA sequence thereof; and
   d. optionally a protease, a cellulolytic enzyme composition, or a protease and a cellulolytic composition.

7. The process of claim 1, wherein steps (b) and (c) are performed simultaneously in a simultaneous saccharification and fermentation.

8. The process of claim 7, wherein an alpha-amylase is present or added during the simultaneous saccharification and fermentation.

9. The process of claim 7, wherein the cellulolytic enzyme composition is present or added during the simultaneous saccharification and fermentation.

10. The process of claim 7, wherein the protease is present or added during the simultaneous saccharification and fermentation.

* * * * *

SEQUENCE LISTING

<160> NUMBER OF SEQ ID NOS: 35

<210> SEQ ID NO 1
<211> LENGTH: 694
<212> TYPE: PRT
<213> ORGANISM: Myceliophthora sepedonium

<400> SEQUENCE: 1

```
Met Ala Leu Arg His Ile Ala Ala Ala Ala Ile Ala Gly Leu Ala Ser
1               5                   10                  15

Arg Thr Ala Ala Leu Tyr Ile Asn Gly Ser Val Thr Ala Pro Cys Asp
            20                  25                  30

Ser Pro Ile Tyr Cys Gln Gly Glu Leu Leu Lys Ala Val Glu Leu Ala
        35                  40                  45

Arg Pro Phe Val Asp Ser Lys Thr Phe Val Asp Met Pro Thr Ile Lys
    50                  55                  60

Pro Val Asp Glu Val Leu Ala Ala Phe Ser Lys Leu Ser Leu Pro Leu
65                  70                  75                  80

Ser Asn Asn Ser Glu Leu Asn Ala Phe Leu Tyr Glu Asn Phe Ala Gln
                85                  90                  95

Ala Gly His Glu Leu Glu Glu Val Pro Asp Ser Glu Leu Glu Thr Asp
            100                 105                 110

Ala Lys Phe Leu Asp Lys Leu Glu Asp Arg Thr Ile Lys Glu Phe Val
        115                 120                 125

Gly Lys Val Ile Asp Ile Trp Pro Asp Leu Thr Arg Arg Tyr Ala Gly
    130                 135                 140

Pro Ser Asn Cys Thr Glu Cys Ala Asn Ser Phe Ile Pro Val Asn Arg
145                 150                 155                 160

Thr Phe Val Val Ala Gly Gly Arg Phe Arg Glu Pro Tyr Tyr Trp Asp
                165                 170                 175

Ser Tyr Trp Ile Val Glu Gly Leu Leu Arg Thr Gly Gly Ala Phe Thr
            180                 185                 190

His Ile Ser Lys Asn Ile Ile Glu Asn Phe Leu Asp Phe Val Asp Thr
        195                 200                 205

Ile Gly Phe Ile Pro Asn Gly Ala Arg Ile Tyr Tyr Leu Asn Arg Ser
    210                 215                 220

Gln Pro Pro Leu Leu Thr Leu Met Val Lys Ser Tyr Val Asp Tyr Thr
225                 230                 235                 240

Asn Asp Thr Ser Ile Leu Asp Arg Ala Leu Pro Leu Leu Ile Lys Glu
                245                 250                 255

His Glu Phe Phe Met Asn Asn Arg Thr Val Ser Ile Thr Gly Ser Asn
            260                 265                 270

Gly Lys Glu Tyr Thr Leu Asn Arg Tyr His Val Glu Asn Asn Gln Pro
        275                 280                 285

Arg Pro Glu Ser Phe Arg Glu Asp Tyr Ile Thr Ala Asn Asn Gly Ser
    290                 295                 300

Tyr Tyr Ala Ser Ser Gly Ile Ile Tyr Pro Val Lys Thr Pro Leu Asn
305                 310                 315                 320

Glu Thr Glu Lys Ala Ala Leu Tyr Ser Asn Leu Ala Thr Gly Ala Glu
                325                 330                 335

Ser Gly Trp Asp Tyr Thr Ser Arg Trp Leu Gly Val Pro Ser Asp Ala
            340                 345                 350

Ala Arg Asp Val Tyr Phe Pro Leu Arg Ser Leu Asn Val Arg Asp Ile
        355                 360                 365
```

Val Pro Val Asp Leu Asn Ser Ile Leu Tyr Gln Asn Glu Val Ile Ile
370                 375                 380

Ala Glu Tyr Leu Glu Lys Ala Gly Asn Ser Ser Ala Ala Lys Arg Phe
385                 390                 395                 400

Ala Thr Ala Ala Glu Gln Arg Ser Gly Ala Met Tyr Ser Leu Met Trp
            405                 410                 415

Asn Ala Thr His Trp Ser Tyr Phe Asp Tyr Asn Leu Thr Asp Asn Thr
            420                 425                 430

Gln His Ile Phe Val Pro Ala Asp Glu Asp Thr Ala Pro Gln Asp Arg
            435                 440                 445

Ile Glu Ala Pro Pro Gly Gln Gln Val Phe Phe His Ile Ala Gln Leu
450                 455                 460

Tyr Pro Phe Trp Thr Gly Ala Ala Pro Ala Ser Leu Lys Ala Asn Pro
465                 470                 475                 480

Leu Ala Val Gln Gln Ala Tyr Ala Arg Val Ala Arg Met Leu Asp Ile
            485                 490                 495

Lys Lys Gly Ala Ile Pro Ala Thr Asn Tyr Arg Thr Gly Gln Gln Trp
            500                 505                 510

Asp Gln Pro Asn Val Trp Pro Pro Leu Gln His Ile Leu Met Lys Gly
            515                 520                 525

Leu Leu Asn Thr Pro Ala Thr Phe Gly Lys Ser Asp Pro Ala Tyr Gln
530                 535                 540

Ser Val Gln Asn Leu Ala Leu Arg Leu Ala Gln Arg Tyr Leu Asp Ser
545                 550                 555                 560

Thr Phe Cys Thr Trp Tyr Ala Thr Gly Gly Ser Thr Ser Asp Phe Pro
            565                 570                 575

Gln Leu Glu Gly Val Thr Pro Gly Ala Thr Gly Val Met Phe Glu Lys
            580                 585                 590

Tyr Ala Asp Asn Ala Thr Asn Val Ala Gly Gly Gly Glu Tyr Glu
            595                 600                 605

Val Val Glu Gly Phe Gly Trp Thr Asn Gly Val Leu Ile Trp Ala Ala
610                 615                 620

Asp Val Phe Gly Asn Lys Leu Lys Arg Pro Asp Cys Gly Asn Ile Thr
625                 630                 635                 640

Ala Ala His Thr His Ser Ser Ala Lys Arg Gly Leu Glu Glu Asn Lys
            645                 650                 655

Leu Pro Arg Arg Ala Val Glu Leu Asp Pro Trp Asp Ala Ala Trp Thr
            660                 665                 670

Lys Met Phe Gly Arg Ser Lys Leu Arg Arg Glu Ala Glu Asp Val
            675                 680                 685

Arg Lys Arg Trp Met Ser
    690

<210> SEQ ID NO 2
<211> LENGTH: 1079
<212> TYPE: PRT
<213> ORGANISM: Trichoderma reesei

<400> SEQUENCE: 2

Met Arg Ser Thr Val Thr Ser Ala Ala Leu Leu Ser Leu Leu Gln
1               5                   10                  15

Leu Val Ser Pro Val His Gly Thr Thr Leu Val Asp Arg Val Thr Lys
            20                  25                  30

Cys Leu Ser Arg His Asp Gly Ser Asp Ala Glu Ser His Phe Ser Lys
            35                  40                  45

```
Asn Val Tyr Lys Thr Asp Phe Ala Gly Val Thr Trp Asp Glu Asp Asn
                 50                  55                  60

Trp Leu Leu Ser Thr Thr Gln Leu Lys Gln Gly Ala Phe Glu Ala Arg
 65                  70                  75                  80

Gly Ser Val Ala Asn Gly Tyr Leu Gly Ile Asn Val Ala Ser Val Gly
                 85                  90                  95

Pro Phe Phe Glu Val Asp Thr Glu Glu Asp Gly Asp Val Ile Ser Gly
                100                 105                 110

Trp Pro Leu Phe Ser Arg Arg Gln Ser Phe Ala Thr Val Ala Gly Phe
                115                 120                 125

Trp Asp Ala Gln Pro Gln Met Asn Gly Thr Asn Phe Pro Trp Leu Ser
130                 135                 140

Gln Tyr Gly Ser Asp Thr Ala Ile Ser Gly Ile Pro His Trp Ser Gly
145                 150                 155                 160

Leu Val Leu Asp Leu Gly Gly Thr Tyr Leu Asp Ala Thr Val Ser
                165                 170                 175

Asn Lys Thr Ile Ser His Phe Arg Ser Thr Tyr Asp Tyr Lys Ala Gly
                180                 185                 190

Val Leu Ser Trp Ser Tyr Lys Trp Thr Pro Lys Gly Asn Lys Gly Ser
                195                 200                 205

Phe Asp Ile Ser Tyr Arg Leu Phe Ala Asn Lys Leu His Val Asn Gln
                210                 215                 220

Ala Val Val Asp Met Gln Val Thr Ala Ser Lys Asn Val Gln Ala Ser
225                 230                 235                 240

Ile Val Asn Val Leu Asp Gly Phe Ala Ala Val Arg Thr Asp Phe Val
                245                 250                 255

Glu Ser Gly Glu Asp Gly Ser Ala Ile Phe Ala Ala Val Arg Pro Asn
                260                 265                 270

Gly Val Ala Asn Val Thr Ala Tyr Val Tyr Ala Asp Ile Thr Gly Ser
                275                 280                 285

Gly Gly Val Asn Leu Ser Ser Arg Lys Ile Val His Asn Lys Pro Tyr
                290                 295                 300

Val His Ala Asn Ala Ser Ser Ile Ala Gln Ala Val Pro Val Lys Phe
305                 310                 315                 320

Ala Ala Gly Arg Thr Val Arg Val Thr Lys Phe Val Gly Ala Ala Ser
                325                 330                 335

Ser Asp Ala Phe Lys Asn Pro Lys Gln Val Ala Lys Lys Ala Ala Ala
                340                 345                 350

Ala Gly Leu Ser Asn Gly Tyr Thr Lys Ser Leu Lys Ala His Val Glu
                355                 360                 365

Glu Trp Ala Thr Val Met Pro Glu Ser Ser Val Asp Ser Phe Ala Asp
                370                 375                 380

Pro Lys Thr Gly Lys Leu Pro Ala Asp Ser His Ile Val Asp Ser Ala
385                 390                 395                 400

Ile Ile Ala Val Thr Asn Thr Tyr Tyr Leu Leu Gln Asn Thr Val Gly
                405                 410                 415

Lys Asn Gly Ile Lys Ala Val Asp Gly Ala Pro Val Asn Val Asp Ser
                420                 425                 430

Ile Ser Val Gly Gly Leu Thr Ser Asp Ser Tyr Ala Gly Gln Ile Phe
                435                 440                 445

Trp Asp Ala Asp Leu Trp Met Gln Pro Gly Leu Val Ala Ala His Pro
450                 455                 460
```

-continued

```
Glu Ala Ala Glu Arg Ile Thr Asn Tyr Arg Leu Ala Arg Tyr Gly Gln
465                 470                 475                 480

Ala Lys Glu Asn Val Lys Thr Ala Tyr Ala Gly Ser Gln Asn Glu Thr
            485                 490                 495

Phe Phe Ser Ala Ser Ala Ala Val Phe Pro Trp Thr Ser Gly Arg Tyr
            500                 505                 510

Gly Asn Cys Thr Ala Thr Gly Pro Cys Trp Asp Tyr Glu Tyr His Leu
            515                 520                 525

Asn Gly Asp Ile Gly Ile Ser Leu Val Asn Gln Trp Val Val Asn Gly
            530                 535                 540

Asp Thr Lys Asp Phe Glu Lys Asn Leu Phe Pro Val Tyr Asp Ser Val
545                 550                 555                 560

Ala Gln Leu Tyr Gly Asn Leu Leu Arg Pro Asn Lys Thr Ser Trp Thr
            565                 570                 575

Leu Thr Asn Met Thr Asp Pro Asp Glu Tyr Ala Asn His Val Asp Ala
            580                 585                 590

Gly Gly Tyr Thr Met Pro Leu Ile Ala Glu Thr Leu Gln Lys Ala Asn
            595                 600                 605

Ser Phe Arg Gln Gln Phe Gly Ile Glu Gln Asn Lys Thr Trp Asn Asp
            610                 615                 620

Met Ala Ser Asn Val Leu Val Leu Arg Glu Asn Gly Val Thr Leu Glu
625                 630                 635                 640

Phe Thr Ala Met Asn Gly Thr Ala Val Val Lys Gln Ala Asp Val Ile
                    645                 650                 655

Met Leu Thr Tyr Pro Leu Ser Tyr Gly Thr Asn Tyr Ser Ala Gln Asp
            660                 665                 670

Ala Leu Asn Asp Leu Asp Tyr Tyr Ala Asn Lys Gln Ser Pro Asp Gly
            675                 680                 685

Pro Ala Met Thr Tyr Ala Phe Phe Ser Ile Val Ala Asn Glu Ile Ser
690                 695                 700

Pro Ser Gly Cys Ser Ala Tyr Thr Tyr Ala Gln Asn Ala Phe Lys Pro
705                 710                 715                 720

Tyr Val Arg Ala Pro Phe Tyr Gln Ile Ser Glu Gln Leu Ile Asp Asp
                    725                 730                 735

Ala Ser Val Asn Gly Gly Thr His Pro Ala Tyr Pro Phe Leu Thr Gly
            740                 745                 750

His Gly Gly Ala His Gln Val Val Leu Phe Gly Tyr Leu Gly Leu Arg
            755                 760                 765

Leu Val Pro Asp Asp Val Ile His Ile Glu Pro Asn Leu Pro Pro Gln
770                 775                 780

Ile Pro Tyr Leu Arg Tyr Arg Thr Phe Tyr Trp Arg Gly Trp Pro Ile
785                 790                 795                 800

Ser Ala Trp Ser Asn Tyr Thr His Thr Thr Leu Ser Arg Ala Ala Gly
                    805                 810                 815

Val Ala Ala Leu Glu Gly Ala Asp Gln Arg Phe Ala Arg Lys Pro Ile
            820                 825                 830

Thr Ile His Ala Gly Pro Glu Gln Asp Pro Thr Ala Tyr Arg Leu Pro
            835                 840                 845

Val Lys Gly Ser Val Val Ile Pro Asn Lys Gln Ile Gly Ser Gln Gln
            850                 855                 860

Thr Tyr Ala Gly Asn Leu Val Gln Cys His Ala Ala Ser Ser Pro Asn
865                 870                 875                 880

Asp Tyr Val Pro Gly Gln Phe Pro Ile Ala Ala Val Asp Gly Ala Thr
```

```
                              885                 890                 895
Ser Thr Lys Trp Gln Pro Ala Ser Ala Asp Lys Val Ser Ser Ile Thr
                    900                 905                 910

Val Ser Leu Asp Lys Glu Asp Val Gly Ser Leu Val Ser Gly Phe His
                915                 920                 925

Phe Asp Trp Ala Gln Ala Pro Pro Val Asn Ala Thr Val Ile Phe His
            930                 935                 940

Asp Glu Ala Leu Ala Asp Pro Ala Thr Ala Leu Ala Ser Ala His Lys
945                 950                 955                 960

His Asn Ser Lys Tyr Thr Thr Val Thr Ser Leu Thr Asn Ile Glu Leu
                965                 970                 975

Ser Asp Pro Tyr Val Ser Thr Lys Asp Leu Asn Ala Ile Ala Ile Pro
            980                 985                 990

Ile Gly Asn Thr Thr Asn Val Thr Leu Ser His Pro Val Ala Ala Ser
        995                 1000                1005

Arg Tyr Ala Ser Leu Leu Ile Val Gly Asn Gln Gly Leu Asp Pro
    1010                1015                1020

Val Asp Val Lys Ala Lys Asn Gly Thr Gly Ala Thr Val Ala Glu
    1025                1030                1035

Trp Ala Ile Phe Gly His Gly Lys Glu His Ser Gly Lys Pro Ser
    1040                1045                1050

Ser His Ser Lys Arg Arg Leu Asn Val Arg Thr Ala Ala Thr Leu
    1055                1060                1065

Ser Asn Pro Arg Ser Phe Met Arg Arg Arg Leu
    1070                1075

<210> SEQ ID NO 3
<211> LENGTH: 1072
<212> TYPE: PRT
<213> ORGANISM: Aspergillus niger

<400> SEQUENCE: 3

Met Gln Val Lys Phe Leu Ala Thr Leu Leu Pro Leu Leu Leu His Leu
1               5                   10                  15

Pro Ala Ala Val Asp Gly Leu Pro Gly Lys Asn Ala Arg Ile Ser Ala
            20                  25                  30

Ser Leu Lys Arg His Ala Gly Arg Asp Val Pro Gln Thr Ala Leu Asn
        35                  40                  45

Ser Thr Asn Val Tyr Gln Thr Lys Phe Ser Gly Val Thr Trp Asp Glu
    50                  55                  60

Asp His Trp Leu Leu Thr Thr Thr Pro Asp Gln Gly His Tyr Gln
65                  70                  75                  80

Ser Arg Gly Ser Val Ala Asn Gly Tyr Leu Gly Ile Asn Val Ala Asn
                85                  90                  95

Ile Gly Pro Phe Phe Glu Leu Asp Glu Pro Val Asn Gly Asp Val Ile
            100                 105                 110

Asn Gly Trp Pro Leu Tyr Ser Arg Arg Gln Ser Phe Ala Thr Ile Ser
        115                 120                 125

Gly Phe Trp Asp Arg Gln Ala His Thr Asn Gly Ser Asn Phe Pro Trp
    130                 135                 140

Leu Ser Gln Tyr Gly Asp Asp Ser Val Ile Ser Gly Val Pro His Trp
145                 150                 155                 160

Ser Gly Leu Ile Leu Asp Leu Gly Asp Asp Thr Tyr Leu Asp Ala Thr
                165                 170                 175
```

Val Asp Asn Arg Thr Ile Ser Asn Phe Lys Ser Thr Tyr Asp Phe Lys
                180                 185                 190

Ser Gly Val Leu Ser Trp Ser Tyr Thr Trp Thr Pro Gln Gly Asn Lys
        195                 200                 205

Gly Ser Tyr Ala Ile Thr Tyr Arg Leu Phe Ala His Lys Leu Tyr Val
        210                 215                 220

Asn Arg Ala Val Val Asp Met Glu Ile Thr Pro Leu Thr Asn Gly Asn
225                 230                 235                 240

Ala Thr Val Val Asn Val Leu Asp Gly Tyr Ala Ala Val Arg Thr Asp
                245                 250                 255

Phe Val Ala Ser Gly Gln Glu Glu Gly Ala Ile Phe Ser Ala Val Arg
                260                 265                 270

Pro Trp Gly Val Asn Asn Val Thr Ala Tyr Val Tyr Ala Thr Leu Asp
                275                 280                 285

Gly Ser Asp Ser Val Asp Leu Ser Ser Arg Arg Ile Val Thr Asp Lys
        290                 295                 300

Pro Tyr Val Ser Thr Asn Ser Ser Val Ala Gln Ala Val Asp Val
305                 310                 315                 320

Met Phe Thr Ala Asn Glu Thr Val Arg Ile Thr Lys Phe Val Gly Gly
                325                 330                 335

Ala Thr Thr Asp Tyr Phe Leu Ala Thr Gln Glu Thr Ala Lys Ala Ala
                340                 345                 350

Cys Leu Ala Gly Leu Ala Asp Gly Tyr Val Lys Ser Leu Gln Ser His
        355                 360                 365

Val Gly Glu Trp Ala Thr Ile Met His Asp His Ser Val Asp Arg Phe
        370                 375                 380

Thr Asp Pro Ala Thr Gly Lys Leu Pro Glu Asp Ser His Ile Val Asp
385                 390                 395                 400

Ser Ala Ile Ile Ala Val Thr Asn Thr Tyr Tyr Leu Leu Gln Asn Thr
                405                 410                 415

Ala Gly Thr Asn Ala Ile Val Ala Gly Gly Ile Pro Val Asn Val
                420                 425                 430

Asp Ser Cys Ala Pro Gly Gly Leu Thr Ser Asp Ser Tyr Gly Gly Gln
        435                 440                 445

Ile Phe Trp Asp Ala Asp Leu Trp Met Gln Pro Gly Leu Val Ala Ser
        450                 455                 460

His Pro Glu Ser Ala Gln Arg Phe Thr Asn Tyr Arg Ile Ala Leu His
465                 470                 475                 480

Tyr Gln Ala Gln Ala Asn Ile Glu Thr Ala Phe Thr Gly Ser Lys Asn
                485                 490                 495

Gln Thr Ser Phe Ser Ser Ala Ala Ile Tyr Pro Trp Thr Ser Gly
        500                 505                 510

Arg Phe Gly Asn Cys Thr Ala Thr Gly Pro Cys Trp Asp Tyr Gln Tyr
        515                 520                 525

His Leu Asn Gly Asp Ile Gly Leu Ala Met Ile Asn Gln Trp Val Ala
        530                 535                 540

Ser Gly Asp Thr Ala Trp Phe Lys Asn Tyr Leu Phe Pro Ile Tyr Asp
545                 550                 555                 560

Ala Ala Ala Thr Leu Tyr Ser Glu Leu Val Glu Arg Asn Gly Ser Ser
                565                 570                 575

Trp Thr Leu Thr Asn Met Thr Asp Pro Asp Glu Tyr Ala Asn Ser Ile
                580                 585                 590

Asn Ala Gly Gly Tyr Thr Met Pro Leu Ile Ala Glu Thr Leu Gln Asn

```
                595                 600                 605
Ala Asn Lys Leu Arg Lys Gln Phe Gly Leu Glu Pro Asn Glu Thr Trp
610                 615                 620

Asp Glu Ile Ala Glu Asp Val Leu Ile Leu Arg Glu Asn Gly Val Thr
625                 630                 635                 640

Leu Glu Tyr Thr Ser Met Asn Gly Ser Ala Val Val Lys Gln Ala Asp
                645                 650                 655

Ile Val Leu Asn Thr Phe Pro Leu Thr Tyr Glu Ser Asp Asn Tyr Thr
                660                 665                 670

Ala Thr Asn Ser Leu Thr Asp Leu Asp Tyr Tyr Ala Asn Lys Gln Ser
                675                 680                 685

Ala Asp Gly Pro Ala Met Thr Tyr Ala Ile Phe Ala Ile Val Ala Ser
690                 695                 700

Asp Val Ser Pro Ser Gly Cys Ser Ala Phe Thr Tyr His Gln Tyr Ser
705                 710                 715                 720

Tyr Ala Pro Tyr Ala Arg Gly Pro Trp Tyr Gln Leu Ser Glu Gln Met
                725                 730                 735

Ile Asp Asp Ala Ser Ile Asn Gly Gly Thr His Pro Ala Phe Pro Phe
                740                 745                 750

Leu Thr Gly His Gly Gly Ala Asn Gln Val Ala Leu Tyr Gly Tyr Leu
                755                 760                 765

Gly Leu Arg Leu His Pro Asp Asp Thr Ile Tyr Ile Asp Pro Asn Leu
770                 775                 780

Pro Pro Gln Ile Pro His Ile Thr Tyr Arg Thr Phe Tyr Trp His Gly
785                 790                 795                 800

Trp Pro Ile Ser Ala Trp Ser Asn Tyr Thr His Thr Ile Gln Arg
                805                 810                 815

Asp Ser Ser Leu Ala Pro Leu Ala Ser Ala Asp Leu Leu Phe Ser Asn
                820                 825                 830

Val Ser Ile Lys Val Gln Val Gly Gln Ser Thr Ala Ser Ala Asp Glu
                835                 840                 845

Ala Thr Ile Tyr Tyr Leu Pro Leu Ser Gly Ala Leu Thr Val Pro Asn
850                 855                 860

Arg Met Ile Gly Ser Val Asn Thr Thr Pro Gly Asn Gln Val Gln Cys
865                 870                 875                 880

His Pro Val Tyr Ser Pro Asp Ala Tyr Glu Pro Gly Gln Phe Pro Ile
                885                 890                 895

Ser Ala Val Asp Gly Ala Thr Ser Thr Lys Trp Gln Pro Ser Thr Ser
                900                 905                 910

Asp Leu Thr Ser Leu Thr Val Thr Leu Ser Thr Thr Ala Glu Ala Gly
                915                 920                 925

Ala Glu Glu Val Ser Gly Phe Tyr Phe Asp Trp Ser Gln Ala Pro Pro
930                 935                 940

Glu Asn Leu Thr Val Ile Phe His Asp Ser Pro Ile Gly Asn Pro Ser
945                 950                 955                 960

Thr Val Phe Ala Ala Ala Gly Ser Asn Ser Thr Gly Tyr Arg Val Ile
                965                 970                 975

Thr Ser Met Ser Asn Ile Val Gln Ser Lys Pro Tyr Asn Ala Ile Ser
                980                 985                 990

Ala Glu Glu Leu Asn Val Val Ser Ile Pro Thr Ala Asn Thr Thr Thr
                995                 1000                1005

Ile Thr Leu Asp Ala Pro Val Gln Lys Ala Arg Tyr Ala Thr Leu
        1010                1015                1020
```

Leu Ile Ala Gly Asn Gln Ala Asn Glu Thr Ala Gly Ala Thr Val
    1025                1030                1035

Ala Glu Trp Val Ile Leu Gly Gln Asn Ser Thr Ser Ser Ser Ser
    1040                1045                1050

Ala Gln Ala Lys Arg Lys Met Ser Ala Arg Ser Lys Ala Thr Leu
    1055                1060                1065

Ala Gln Leu Ser
    1070

<210> SEQ ID NO 4
<211> LENGTH: 598
<212> TYPE: PRT
<213> ORGANISM: Talaromyces emersonii

<400> SEQUENCE: 4

Arg Ala Pro Val Ala Ala Arg Ala Thr Gly Ser Leu Asp Ser Phe Leu
  1               5                  10                  15

Ala Thr Glu Thr Pro Ile Ala Leu Gln Gly Val Leu Asn Asn Ile Gly
             20                  25                  30

Pro Asn Gly Ala Asp Val Ala Gly Ala Ser Ala Gly Ile Val Val Ala
         35                  40                  45

Ser Pro Ser Arg Ser Asp Pro Asn Tyr Phe Tyr Ser Trp Thr Arg Asp
     50                  55                  60

Ala Ala Leu Thr Ala Lys Tyr Leu Val Asp Ala Phe Ile Ala Gly Asn
 65                  70                  75                  80

Lys Asp Leu Glu Gln Thr Ile Gln Gln Tyr Ile Ser Ala Gln Ala Lys
                 85                  90                  95

Val Gln Thr Ile Ser Asn Pro Ser Gly Asp Leu Ser Thr Gly Gly Leu
            100                 105                 110

Gly Glu Pro Lys Phe Asn Val Asn Glu Thr Ala Phe Thr Gly Pro Trp
        115                 120                 125

Gly Arg Pro Gln Arg Asp Gly Pro Ala Leu Arg Ala Thr Ala Leu Ile
    130                 135                 140

Ala Tyr Ala Asn Tyr Leu Ile Asp Asn Gly Glu Ala Ser Thr Ala Asp
145                 150                 155                 160

Glu Ile Ile Trp Pro Ile Val Gln Asn Asp Leu Ser Tyr Ile Thr Gln
                165                 170                 175

Tyr Trp Asn Ser Ser Thr Phe Asp Leu Trp Glu Val Glu Gly Ser
            180                 185                 190

Ser Phe Phe Thr Thr Ala Val Gln His Arg Ala Leu Val Glu Gly Asn
195                 200                 205

Ala Leu Ala Thr Arg Leu Asn His Thr Cys Ser Asn Cys Val Ser Gln
    210                 215                 220

Ala Pro Gln Val Leu Cys Phe Leu Gln Ser Tyr Trp Thr Gly Ser Tyr
225                 230                 235                 240

Val Leu Ala Asn Phe Gly Gly Ser Gly Arg Ser Gly Lys Asp Val Asn
                245                 250                 255

Ser Ile Leu Gly Ser Ile His Thr Phe Asp Pro Ala Gly Gly Cys Asp
            260                 265                 270

Asp Ser Thr Phe Gln Pro Cys Ser Ala Arg Ala Leu Ala Asn His Lys
        275                 280                 285

Val Val Thr Asp Ser Phe Arg Ser Ile Tyr Ala Ile Asn Ser Gly Ile
    290                 295                 300

Ala Glu Gly Ser Ala Val Ala Val Gly Arg Tyr Pro Glu Asp Val Tyr

```
            305                 310                 315                 320

Gln Gly Gly Asn Pro Trp Tyr Leu Ala Thr Ala Ala Ala Glu Gln
            325                 330                 335

Leu Tyr Asp Ala Ile Tyr Gln Trp Lys Lys Ile Gly Ser Ile Ser Ile
            340                 345                 350

Thr Asp Val Ser Leu Pro Phe Phe Gln Asp Ile Tyr Pro Ser Ala Ala
            355                 360                 365

Val Gly Thr Tyr Asn Ser Gly Ser Thr Thr Phe Asn Asp Ile Ile Ser
            370                 375                 380

Ala Val Gln Thr Tyr Gly Asp Gly Tyr Leu Ser Ile Val Glu Lys Tyr
385                 390                 395                 400

Thr Pro Ser Asp Gly Ser Leu Thr Glu Gln Phe Ser Arg Thr Asp Gly
            405                 410                 415

Thr Pro Leu Ser Ala Ser Ala Leu Thr Trp Ser Tyr Ala Ser Leu Leu
            420                 425                 430

Thr Ala Ser Ala Arg Arg Gln Ser Val Val Pro Ala Ser Trp Gly Glu
            435                 440                 445

Ser Ser Ala Ser Ser Val Pro Ala Val Cys Ser Ala Thr Ser Ala Thr
            450                 455                 460

Gly Pro Tyr Ser Thr Ala Thr Asn Thr Val Trp Pro Ser Ser Gly Ser
465                 470                 475                 480

Gly Ser Ser Thr Thr Thr Ser Ser Ala Pro Cys Thr Thr Pro Thr Ser
            485                 490                 495

Val Ala Val Thr Phe Asp Glu Ile Val Ser Thr Ser Tyr Gly Glu Thr
            500                 505                 510

Ile Tyr Leu Ala Gly Ser Ile Pro Glu Leu Gly Asn Trp Ser Thr Ala
            515                 520                 525

Ser Ala Ile Pro Leu Arg Ala Asp Ala Tyr Thr Asn Ser Asn Pro Leu
            530                 535                 540

Trp Tyr Val Thr Val Asn Leu Pro Pro Gly Thr Ser Phe Glu Tyr Lys
545                 550                 555                 560

Phe Phe Lys Asn Gln Thr Asp Gly Thr Ile Val Trp Glu Asp Asp Pro
            565                 570                 575

Asn Arg Ser Tyr Thr Val Pro Ala Tyr Cys Gly Gln Thr Thr Ala Ile
            580                 585                 590

Leu Asp Asp Ser Trp Gln
            595

<210> SEQ ID NO 5
<211> LENGTH: 556
<212> TYPE: PRT
<213> ORGANISM: Gloeophyllum sepiarium

<400> SEQUENCE: 5

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Val Ala Ser Pro Ser Thr Ser Asp Pro Asp Tyr
            35                  40                  45

Trp Tyr Thr Trp Thr Arg Asp Ser Ser Leu Val Phe Lys Ser Leu Ile
            50                  55                  60

Asp Gln Tyr Thr Thr Gly Ile Asp Ser Thr Ser Ser Leu Arg Thr Leu
65              70                  75                  80
```

```
Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
            115                 120                 125

Gly Pro Ala Leu Arg Ser Thr Ala Leu Ile Thr Tyr Gly Asn Trp Leu
            130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Ser Phe Phe Thr Thr Ala
            180                 185                 190

Val Gln His Arg Ala Leu Arg Glu Gly Ala Ala Phe Ala Thr Ala Ile
            195                 200                 205

Gly Gln Thr Ser Gln Val Ser Ser Tyr Thr Thr Gln Ala Asp Asn Leu
            210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
            260                 265                 270

Phe Gln Pro Cys Ser Asp Lys Ala Leu Ser Asn Leu Lys Val Tyr Val
            275                 280                 285

Asp Ser Phe Arg Ser Val Tyr Ser Ile Asn Ser Gly Val Ala Ser Asn
            290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
            355                 360                 365

Tyr Ser Ser Ser Ser Ser Thr Tyr Ser Thr Leu Thr Ser Ala Ile Lys
            370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
            435                 440                 445

Thr Val Pro Ser Ser Cys Ser Gly Asn Ser Gly Gly Pro Thr Val Ala
            450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
```

```
                    500                 505                 510
Leu Pro Ala Ser Thr Ala Ile Glu Tyr Lys Tyr Ile Arg Lys Asn Asn
            515                 520                 525

Gly Ala Val Thr Trp Glu Ser Asp Pro Asn Asn Ser Ile Thr Thr Pro
        530                 535                 540

Ala Ser Gly Ser Thr Thr Glu Asn Asp Thr Trp Arg
545                 550                 555

<210> SEQ ID NO 6
<211> LENGTH: 559
<212> TYPE: PRT
<213> ORGANISM: Gloephyllum trabeum

<400> SEQUENCE: 6

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Ile Ala Ser Asn
290                 295                 300

Ala Ala Val Ala Thr Gly Arg Tyr Pro Glu Asp Ser Tyr Gln Gly Gly
305                 310                 315                 320
```

```
Asn Pro Trp Tyr Leu Thr Thr Phe Ala Val Ala Glu Gln Leu Tyr Asp
            325                 330                 335

Ala Leu Asn Val Trp Ala Ala Gln Gly Ser Leu Asn Val Thr Ser Ile
        340                 345                 350

Ser Leu Pro Phe Phe Gln Gln Phe Ser Ser Ser Val Thr Ala Gly Thr
        355                 360                 365

Tyr Ala Ser Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Val Gly Leu
            435                 440                 445

Thr Val Pro Thr Ser Cys Ser Ser Asn Ser Gly Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
                500                 505                 510

Thr Val Asn Leu Pro Ala Ser Thr Ala Ile Gln Tyr Lys Tyr Ile Arg
            515                 520                 525

Lys Asn Asn Gly Ala Val Thr Trp Glu Ser Asp Pro Asn Asn Ser Ile
    530                 535                 540

Thr Thr Pro Ala Ser Gly Ser Val Thr Glu Asn Asp Thr Trp Arg
545                 550                 555

<210> SEQ ID NO 7
<211> LENGTH: 583
<212> TYPE: PRT
<213> ORGANISM: Rhizomucor pusillus

<400> SEQUENCE: 7

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140
```

```
Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
            165                 170                 175

Trp Val Gly Asn Tyr Ser Phe Asp Gly Ile Arg Ile Asp Thr Val Lys
        180                 185                 190

His Ile Arg Lys Asp Phe Trp Thr Gly Tyr Ala Glu Ala Ala Gly Val
    195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
450                 455                 460

Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
530                 535                 540

Lys Phe Ile Arg Ile Glu Ser Asp Asp Ser Val Glu Trp Glu Ser Asp
545                 550                 555                 560
```

Pro Asn Arg Glu Tyr Thr Val Pro Gln Ala Cys Gly Thr Ser Thr Ala
            565                 570                 575

Thr Val Thr Asp Thr Trp Arg
            580

<210> SEQ ID NO 8
<211> LENGTH: 515
<212> TYPE: PRT
<213> ORGANISM: Bacillus stearothermophilus

<400> SEQUENCE: 8

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

-continued

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 9
<211> LENGTH: 413
<212> TYPE: PRT
<213> ORGANISM: Pyrococcus furiosus

<400> SEQUENCE: 9

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly

```
                195                 200                 205
Arg Leu Lys Pro Glu Val Val Ala Pro Gly Asn Trp Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410

<210> SEQ ID NO 10
<211> LENGTH: 595
<212> TYPE: PRT
<213> ORGANISM: Penicillium oxalicum

<400> SEQUENCE: 10

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
                20                  25                  30

Lys Lys Thr Pro Gly Thr Ala Ala Gly Leu Phe Ile Ala Ser Pro Asn
            35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160
```

-continued

Lys Ser Asp Val Ser Gln Val Met Trp Pro Ile Ile Ala Asn Asp Leu
                165                 170                 175
Ala Tyr Val Gly Gln Tyr Trp Asn Asn Thr Gly Phe Asp Leu Trp Glu
            180                 185                 190
Glu Val Asp Gly Ser Ser Phe Phe Thr Ile Ala Val Gln His Arg Ala
        195                 200                 205
Leu Val Glu Gly Ser Gln Leu Ala Lys Lys Leu Gly Lys Ser Cys Asp
    210                 215                 220
Ala Cys Asp Ser Gln Pro Pro Gln Ile Leu Cys Phe Leu Gln Ser Phe
225                 230                 235                 240
Trp Asn Gly Lys Tyr Ile Thr Ser Asn Ile Asn Thr Gln Ala Ser Arg
                245                 250                 255
Ser Gly Ile Asp Leu Asp Ser Val Leu Gly Ser Ile His Thr Phe Asp
            260                 265                 270
Pro Glu Ala Ala Cys Asp Asp Ala Thr Phe Gln Pro Cys Ser Ala Arg
        275                 280                 285
Ala Leu Ala Asn His Lys Val Tyr Val Asp Ser Phe Arg Ser Ile Tyr
    290                 295                 300
Lys Ile Asn Ala Gly Leu Ala Glu Gly Ser Ala Ala Asn Val Gly Arg
305                 310                 315                 320
Tyr Pro Glu Asp Val Tyr Gln Gly Gly Asn Pro Trp Tyr Leu Ala Thr
                325                 330                 335
Leu Gly Ala Ser Glu Leu Leu Tyr Asp Ala Leu Tyr Gln Trp Asp Arg
            340                 345                 350
Leu Gly Lys Leu Glu Val Ser Glu Thr Ser Leu Ser Phe Phe Lys Asp
        355                 360                 365
Phe Asp Ala Thr Val Lys Ile Gly Ser Tyr Ser Arg Asn Ser Lys Thr
    370                 375                 380
Tyr Lys Lys Leu Thr Gln Ser Ile Lys Ser Tyr Ala Asp Gly Phe Ile
385                 390                 395                 400
Gln Leu Val Gln Gln Tyr Thr Pro Ser Asn Gly Ser Leu Ala Glu Gln
                405                 410                 415
Tyr Asp Arg Asn Thr Ala Ala Pro Leu Ser Ala Asn Asp Leu Thr Trp
            420                 425                 430
Ser Phe Ala Ser Phe Leu Thr Ala Thr Gln Arg Arg Asp Ala Val Val
        435                 440                 445
Pro Pro Ser Trp Gly Ala Lys Ser Ala Asn Lys Val Pro Thr Thr Cys
    450                 455                 460
Ser Ala Ser Pro Val Val Gly Thr Tyr Lys Ala Pro Thr Ala Thr Phe
465                 470                 475                 480
Ser Ser Lys Thr Lys Cys Val Pro Ala Lys Asp Ile Val Pro Ile Thr
                485                 490                 495
Phe Tyr Leu Ile Glu Asn Thr Tyr Tyr Gly Glu Asn Val Phe Met Ser
            500                 505                 510
Gly Asn Ile Thr Ala Leu Gly Asn Trp Asp Ala Lys Lys Gly Phe Pro
        515                 520                 525
Leu Thr Ala Asn Leu Tyr Thr Gln Asp Gln Asn Leu Trp Phe Ala Ser
    530                 535                 540
Val Glu Phe Ile Pro Ala Gly Thr Pro Phe Glu Tyr Lys Tyr Tyr Lys
545                 550                 555                 560
Val Glu Pro Asn Gly Asp Ile Thr Trp Glu Lys Gly Pro Asn Arg Val
                565                 570                 575
Phe Val Ala Pro Thr Gly Cys Pro Val Gln Pro His Ser Asn Asp Val

-continued

```
                         580                 585                 590

Trp Gln Phe
        595

<210> SEQ ID NO 11
<211> LENGTH: 556
<212> TYPE: PRT
<213> ORGANISM: Trametes cingulata

<400> SEQUENCE: 11

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
    50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350
```

Ser Leu Pro Phe Phe Gln Gln Phe Ser Ser Gly Val Thr Val Gly Thr
355                 360                 365

Tyr Ala Ser Ser Ser Thr Phe Lys Thr Leu Thr Ser Ala Ile Lys
        370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
            420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Ser Gly Ala Gly Thr Val Ala
    450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
    530                 535                 540

Ala Ser Gly Thr Phe Thr Gln Asn Asp Thr Trp Arg
545                 550                 555

<210> SEQ ID NO 12
<211> LENGTH: 555
<212> TYPE: PRT
<213> ORGANISM: Pycnoporus sanguineus

<400> SEQUENCE: 12

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
        35                  40                  45

Asp Tyr Leu Tyr Thr Trp Thr Arg Asp Ser Ser Leu Val Phe Lys Leu
    50                  55                  60

Leu Ile Asp Gln Phe Thr Ser Gly Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
        115                 120                 125

Gly Pro Ala Leu Arg Ala Thr Ser Ile Ile Arg Tyr Ala Asn Trp Leu
    130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Phe Phe Thr Thr Ala
            180                 185                 190

Val Gln His Arg Ala Leu Arg Glu Gly Ala Thr Phe Ala Ser Arg Ile
        195                 200                 205

Gly Gln Ser Ser Val Val Ser Gly Tyr Thr Thr Gln Ala Asp Asn Leu
    210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Thr Ile Asn Asn Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
        355                 360                 365

Tyr Ser Ala Ser Ser Ser Thr Tyr Ala Thr Leu Thr Ser Ala Ile Arg
    370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Ala Leu Thr Ala Phe
            420                 425                 430

Ala Ala Arg Glu Gly Lys Thr Tyr Gly Ser Trp Gly Ala Ala Gly Leu
        435                 440                 445

Thr Val Pro Ala Ser Cys Ser Gly Gly Gly Ala Thr Val Ala Val
    450                 455                 460

Thr Phe Asn Val Gln Ala Thr Val Phe Gly Glu Asn Ile Tyr Ile
465                 470                 475                 480

Thr Gly Ser Val Ala Ala Leu Gln Asn Trp Ser Pro Asp Asn Ala Leu
                485                 490                 495

Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
        515                 520                 525

Gln Val Thr Trp Glu Ser Asp Pro Asn Asn Gln Ile Thr Thr Pro Ser
    530                 535                 540

Gly Gly Ser Phe Thr Gln Asn Asp Val Trp Arg
545                 550                 555

<210> SEQ ID NO 13
<211> LENGTH: 177
<212> TYPE: PRT
<213> ORGANISM: Thermoascus aurantiacus

<400> SEQUENCE: 13

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
130                 135                 140

Ala Tyr Gly Tyr Gln Ala Ala Met Gly Leu Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 14
<211> LENGTH: 844
<212> TYPE: PRT
<213> ORGANISM: Aspergillus fumigatus

<400> SEQUENCE: 14

Gln Glu Leu Ala Phe Ser Pro Pro Phe Tyr Pro Ser Pro Trp Ala Asp
1               5                   10                  15

Gly Gln Gly Glu Trp Ala Asp Ala His Arg Arg Ala Val Glu Ile Val
            20                  25                  30

Ser Gln Met Thr Leu Ala Glu Lys Val Asn Leu Thr Thr Gly Thr Gly
        35                  40                  45

Trp Glu Met Asp Arg Cys Val Gly Gln Thr Gly Ser Val Pro Arg Leu
50                  55                  60

Gly Ile Asn Trp Gly Leu Cys Gly Gln Asp Ser Pro Leu Gly Ile Arg
65                  70                  75                  80

Phe Ser Asp Leu Asn Ser Ala Phe Pro Ala Gly Thr Asn Val Ala Ala
                85                  90                  95

Thr Trp Asp Lys Thr Leu Ala Tyr Leu Arg Gly Lys Ala Met Gly Glu
            100                 105                 110

Glu Phe Asn Asp Lys Gly Val Asp Ile Leu Leu Gly Pro Ala Ala Gly
        115                 120                 125

Pro Leu Gly Lys Tyr Pro Asp Gly Gly Arg Ile Trp Glu Gly Phe Ser
130                 135                 140

Pro Asp Pro Val Leu Thr Gly Val Leu Phe Ala Glu Thr Ile Lys Gly
145                 150                 155                 160

Ile Gln Asp Ala Gly Val Ile Ala Thr Ala Lys His Tyr Ile Leu Asn
                165                 170                 175

Glu Gln Glu His Phe Arg Gln Val Gly Glu Ala Gln Gly Tyr Gly Tyr

```
                180             185             190
Asn Ile Thr Glu Thr Ile Ser Ser Asn Val Asp Asp Lys Thr Met His
            195                 200                 205
Glu Leu Tyr Leu Trp Pro Phe Ala Asp Ala Val Arg Ala Gly Val Gly
            210                 215                 220
Ala Val Met Cys Ser Tyr Asn Gln Ile Asn Asn Ser Tyr Gly Cys Gln
225                 230                 235                 240
Asn Ser Gln Thr Leu Asn Lys Leu Leu Lys Ala Glu Leu Gly Phe Gln
                245                 250                 255
Gly Phe Val Met Ser Asp Trp Ser Ala His His Ser Gly Val Gly Ala
                260                 265                 270
Ala Leu Ala Gly Leu Asp Met Ser Met Pro Gly Asp Ile Ser Phe Asp
                275                 280                 285
Asp Gly Leu Ser Phe Trp Gly Thr Asn Leu Thr Val Ser Val Leu Asn
                290                 295                 300
Gly Thr Val Pro Ala Trp Arg Val Asp Asp Met Ala Val Arg Ile Met
305                 310                 315                 320
Thr Ala Tyr Tyr Lys Val Gly Arg Asp Arg Leu Arg Ile Pro Pro Asn
                325                 330                 335
Phe Ser Ser Trp Thr Arg Asp Glu Tyr Gly Trp Glu His Ser Ala Val
                340                 345                 350
Ser Glu Gly Ala Trp Thr Lys Val Asn Asp Phe Val Asn Val Gln Arg
                355                 360                 365
Ser His Ser Gln Ile Ile Arg Glu Ile Gly Ala Ala Ser Thr Val Leu
                370                 375                 380
Leu Lys Asn Thr Gly Ala Leu Pro Leu Thr Gly Lys Glu Val Lys Val
385                 390                 395                 400
Gly Val Leu Gly Glu Asp Ala Gly Ser Asn Pro Trp Gly Ala Asn Gly
                405                 410                 415
Cys Pro Asp Arg Gly Cys Asp Asn Gly Thr Leu Ala Met Ala Trp Gly
                420                 425                 430
Ser Gly Thr Ala Asn Phe Pro Tyr Leu Val Thr Pro Glu Gln Ala Ile
                435                 440                 445
Gln Arg Glu Val Ile Ser Asn Gly Gly Asn Val Phe Ala Val Thr Asp
                450                 455                 460
Asn Gly Ala Leu Ser Gln Met Ala Asp Val Ala Ser Gln Ser Ser Val
465                 470                 475                 480
Ser Leu Val Phe Val Asn Ala Asp Ser Gly Glu Gly Phe Ile Ser Val
                485                 490                 495
Asp Gly Asn Glu Gly Asp Arg Lys Asn Leu Thr Leu Trp Lys Asn Gly
                500                 505                 510
Glu Ala Val Ile Asp Thr Val Val Ser His Cys Asn Asn Thr Ile Val
                515                 520                 525
Val Ile His Ser Val Gly Pro Val Leu Ile Asp Arg Trp Tyr Asp Asn
                530                 535                 540
Pro Asn Val Thr Ala Ile Ile Trp Ala Gly Leu Pro Gly Gln Glu Ser
545                 550                 555                 560
Gly Asn Ser Leu Val Asp Val Leu Tyr Gly Arg Val Asn Pro Ser Ala
                565                 570                 575
Lys Thr Pro Phe Thr Trp Gly Lys Thr Arg Glu Ser Tyr Gly Ala Pro
                580                 585                 590
Leu Leu Thr Glu Pro Asn Asn Gly Asn Gly Ala Pro Gln Asp Asp Phe
                595                 600                 605
```

```
Asn Glu Gly Val Phe Ile Asp Tyr Arg His Phe Asp Lys Arg Asn Glu
            610                 615                 620

Thr Pro Ile Tyr Glu Phe Gly His Gly Leu Ser Tyr Thr Thr Phe Gly
625                 630                 635                 640

Tyr Ser His Leu Arg Val Gln Ala Leu Asn Ser Ser Ser Ser Ala Tyr
            645                 650                 655

Val Pro Thr Ser Gly Glu Thr Lys Pro Ala Pro Thr Tyr Gly Glu Ile
            660                 665                 670

Gly Ser Ala Ala Asp Tyr Leu Tyr Pro Glu Gly Leu Lys Arg Ile Thr
            675                 680                 685

Lys Phe Ile Tyr Pro Trp Leu Asn Ser Thr Asp Leu Glu Asp Ser Ser
            690                 695                 700

Asp Asp Pro Asn Tyr Gly Trp Glu Asp Ser Glu Tyr Ile Pro Glu Gly
705                 710                 715                 720

Ala Arg Asp Gly Ser Pro Gln Pro Leu Leu Lys Ala Gly Gly Ala Pro
            725                 730                 735

Gly Gly Asn Pro Thr Leu Tyr Gln Asp Leu Val Arg Val Ser Ala Thr
            740                 745                 750

Ile Thr Asn Thr Gly Asn Val Ala Gly Tyr Glu Val Pro Gln Leu Tyr
            755                 760                 765

Val Ser Leu Gly Gly Pro Asn Glu Pro Arg Val Val Leu Arg Lys Phe
            770                 775                 780

Asp Arg Ile Phe Leu Ala Pro Gly Glu Gln Lys Val Trp Thr Thr Thr
785                 790                 795                 800

Leu Asn Arg Arg Asp Leu Ala Asn Trp Asp Val Glu Ala Gln Asp Trp
            805                 810                 815

Val Ile Thr Lys Tyr Pro Lys Lys Val His Val Gly Ser Ser Ser Arg
            820                 825                 830

Lys Leu Pro Leu Arg Ala Pro Leu Pro Arg Val Tyr
            835                 840

<210> SEQ ID NO 15
<211> LENGTH: 227
<212> TYPE: PRT
<213> ORGANISM: Thermoascus aurantiacus

<400> SEQUENCE: 15

Phe Val Gln Asn Ile Val Ile Asp Gly Lys Lys Tyr Tyr Gly Gly Tyr
1               5                   10                  15

Leu Val Asn Gln Tyr Pro Tyr Met Ser Asn Pro Pro Glu Val Ile Ala
            20                  25                  30

Trp Ser Thr Thr Ala Thr Asp Leu Gly Phe Val Asp Gly Thr Gly Tyr
        35                  40                  45

Gln Thr Pro Asp Ile Ile Cys His Arg Gly Ala Lys Pro Gly Ala Leu
    50                  55                  60

Thr Ala Pro Val Ser Pro Gly Gly Thr Val Glu Leu Gln Trp Thr Pro
65                  70                  75                  80

Trp Pro Asp Ser His His Gly Pro Val Ile Asn Tyr Leu Ala Pro Cys
            85                  90                  95

Asn Gly Asp Cys Ser Thr Val Asp Lys Thr Gln Leu Glu Phe Phe Lys
            100                 105                 110

Ile Ala Glu Ser Gly Leu Ile Asn Asp Asp Asn Pro Pro Gly Ile Trp
        115                 120                 125

Ala Ser Asp Asn Leu Ile Ala Ala Asn Asn Ser Trp Thr Val Thr Ile
```

```
                130                 135                 140
Pro Thr Thr Ile Ala Pro Gly Asn Tyr Val Leu Arg His Glu Ile Ile
145                 150                 155                 160

Ala Leu His Ser Ala Gln Asn Gln Asp Gly Ala Gln Asn Tyr Pro Gln
                165                 170                 175

Cys Ile Asn Leu Gln Val Thr Gly Gly Ser Asp Asn Pro Ala Gly
            180                 185                 190

Thr Leu Gly Thr Ala Leu Tyr His Asp Thr Asp Pro Gly Ile Leu Ile
                195                 200                 205

Asn Ile Tyr Gln Lys Leu Ser Ser Tyr Ile Ile Pro Gly Pro Pro Leu
210                 215                 220

Tyr Thr Gly
225

<210> SEQ ID NO 16
<211> LENGTH: 228
<212> TYPE: PRT
<213> ORGANISM: Penicillium emersonii

<400> SEQUENCE: 16

His Gly Phe Val Gln Gly Ile Val Ile Gly Asp Gln Phe Tyr Ser Gly
1               5                   10                  15

Tyr Ile Val Asn Ser Phe Pro Tyr Glu Ser Asn Pro Pro Val Ile
            20                  25                  30

Gly Trp Ala Thr Thr Ala Thr Asp Leu Gly Phe Val Asp Gly Thr Gly
                35                  40                  45

Tyr Gln Gly Pro Asp Ile Ile Cys His Arg Asn Ala Thr Pro Ala Pro
            50                  55                  60

Leu Thr Ala Pro Val Ala Ala Gly Gly Thr Val Glu Leu Gln Trp Thr
65                  70                  75                  80

Pro Trp Pro Asp Ser His His Gly Pro Val Ile Thr Tyr Leu Ala Pro
                85                  90                  95

Cys Asn Gly Asn Cys Ser Thr Val Asp Lys Thr Thr Leu Glu Phe Phe
            100                 105                 110

Lys Ile Asp Gln Gln Gly Leu Ile Asp Asp Thr Ser Pro Pro Gly Thr
            115                 120                 125

Trp Ala Ser Asp Asn Leu Ile Ala Asn Asn Ser Trp Thr Val Thr
130                 135                 140

Ile Pro Asn Ser Val Ala Pro Gly Asn Tyr Val Leu Arg His Glu Ile
145                 150                 155                 160

Ile Ala Leu His Ser Ala Asn Asn Lys Asp Gly Ala Gln Asn Tyr Pro
                165                 170                 175

Gln Cys Ile Asn Ile Glu Val Thr Gly Gly Ser Asp Ala Pro Glu
            180                 185                 190

Gly Thr Leu Gly Glu Asp Leu Tyr His Asp Thr Asp Pro Gly Ile Leu
                195                 200                 205

Val Asp Ile Tyr Glu Pro Ile Ala Thr Tyr Thr Ile Pro Gly Pro Pro
            210                 215                 220

Glu Pro Thr Phe
225

<210> SEQ ID NO 17
<211> LENGTH: 506
<212> TYPE: PRT
<213> ORGANISM: Aspergillus fumigatus
```

<400> SEQUENCE: 17

```
Gln Gln Val Gly Thr Ser Gln Ala Glu Val His Pro Ser Met Thr Trp
1               5                   10                  15
Gln Ser Cys Thr Ala Gly Gly Ser Cys Thr Thr Asn Asn Gly Lys Val
                20                  25                  30
Val Ile Asp Ala Asn Trp Arg Trp Val His Lys Val Gly Asp Tyr Thr
            35                  40                  45
Asn Cys Tyr Thr Gly Asn Thr Trp Asp Thr Thr Ile Cys Pro Asp Asp
        50                  55                  60
Ala Thr Cys Ala Ser Asn Cys Ala Leu Glu Gly Ala Asn Tyr Glu Ser
65                  70                  75                  80
Thr Tyr Gly Val Thr Ala Ser Gly Asn Ser Leu Arg Leu Asn Phe Val
                85                  90                  95
Thr Thr Ser Gln Gln Lys Asn Ile Gly Ser Arg Leu Tyr Met Met Lys
            100                 105                 110
Asp Asp Ser Thr Tyr Glu Met Phe Lys Leu Leu Asn Gln Glu Phe Thr
        115                 120                 125
Phe Asp Val Asp Val Ser Asn Leu Pro Cys Gly Leu Asn Gly Ala Leu
130                 135                 140
Tyr Phe Val Ala Met Asp Ala Asp Gly Gly Met Ser Lys Tyr Pro Thr
145                 150                 155                 160
Asn Lys Ala Gly Ala Lys Tyr Gly Thr Gly Tyr Cys Asp Ser Gln Cys
                165                 170                 175
Pro Arg Asp Leu Lys Phe Ile Asn Gly Gln Ala Asn Val Glu Gly Trp
            180                 185                 190
Gln Pro Ser Ser Asn Asp Ala Asn Ala Gly Thr Gly Asn His Gly Ser
        195                 200                 205
Cys Cys Ala Glu Met Asp Ile Trp Glu Ala Asn Ser Ile Ser Thr Ala
210                 215                 220
Phe Thr Pro His Pro Cys Asp Thr Pro Gly Gln Val Met Cys Thr Gly
225                 230                 235                 240
Asp Ala Cys Gly Gly Thr Tyr Ser Ser Asp Arg Tyr Gly Gly Thr Cys
                245                 250                 255
Asp Pro Asp Gly Cys Asp Phe Asn Ser Phe Arg Gln Gly Asn Lys Thr
            260                 265                 270
Phe Tyr Gly Pro Gly Met Thr Val Asp Thr Lys Ser Lys Phe Thr Val
        275                 280                 285
Val Thr Gln Phe Ile Thr Asp Asp Gly Thr Ser Ser Gly Thr Leu Lys
290                 295                 300
Glu Ile Lys Arg Phe Tyr Val Gln Asn Gly Lys Val Ile Pro Asn Ser
305                 310                 315                 320
Glu Ser Thr Trp Thr Gly Val Ser Gly Asn Ser Ile Thr Thr Glu Tyr
                325                 330                 335
Cys Thr Ala Gln Lys Ser Leu Phe Gln Asp Gln Asn Val Phe Glu Lys
            340                 345                 350
His Gly Gly Leu Glu Gly Met Gly Ala Ala Leu Ala Gln Gly Met Val
        355                 360                 365
Leu Val Met Ser Leu Trp Asp Asp His Ser Ala Asn Met Leu Trp Leu
370                 375                 380
Asp Ser Asn Tyr Pro Thr Thr Ala Ser Ser Thr Thr Pro Gly Val Ala
385                 390                 395                 400
Arg Gly Thr Cys Asp Ile Ser Ser Gly Val Pro Ala Asp Val Glu Ala
                405                 410                 415
```

Asn His Pro Asp Ala Tyr Val Tyr Ser Asn Ile Lys Val Gly Pro
            420                 425                 430

Ile Gly Ser Thr Phe Asn Ser Gly Ser Asn Pro Gly Gly Gly Thr
        435                 440                 445

Thr Thr Thr Thr Thr Thr Gln Pro Thr Thr Thr Thr Thr Ala Gly
    450                 455                 460

Asn Pro Gly Gly Thr Gly Val Ala Gln His Tyr Gly Gln Cys Gly Gly
465                 470                 475                 480

Ile Gly Trp Thr Gly Pro Thr Thr Cys Ala Ser Pro Tyr Thr Cys Gln
            485                 490                 495

Lys Leu Asn Asp Tyr Tyr Ser Gln Cys Leu
            500                 505

<210> SEQ ID NO 18
<211> LENGTH: 435
<212> TYPE: PRT
<213> ORGANISM: Aspergillus fumigatus

<400> SEQUENCE: 18

Gln Gln Thr Val Trp Gly Gln Cys Gly Gly Gln Gly Trp Ser Gly Pro
1               5                   10                  15

Thr Ser Cys Val Ala Gly Ala Ala Cys Ser Thr Leu Asn Pro Tyr Tyr
            20                  25                  30

Ala Gln Cys Ile Pro Gly Ala Thr Ala Thr Ser Thr Thr Leu Thr Thr
        35                  40                  45

Thr Thr Ala Ala Thr Thr Thr Ser Gln Thr Thr Thr Lys Pro Thr Thr
    50                  55                  60

Thr Gly Pro Thr Thr Ser Ala Pro Thr Val Thr Ala Ser Gly Asn Pro
65                  70                  75                  80

Phe Ser Gly Tyr Gln Leu Tyr Ala Asn Pro Tyr Tyr Ser Ser Glu Val
                85                  90                  95

His Thr Leu Ala Met Pro Ser Leu Pro Ser Ser Leu Gln Pro Lys Ala
            100                 105                 110

Ser Ala Val Ala Glu Val Pro Ser Phe Val Trp Leu Asp Val Ala Ala
        115                 120                 125

Lys Val Pro Thr Met Gly Thr Tyr Leu Ala Asp Ile Gln Ala Lys Asn
130                 135                 140

Lys Ala Gly Ala Asn Pro Pro Ile Ala Gly Ile Phe Val Val Tyr Asp
145                 150                 155                 160

Leu Pro Asp Arg Asp Cys Ala Ala Leu Ala Ser Asn Gly Glu Tyr Ser
                165                 170                 175

Ile Ala Asn Asn Gly Val Ala Asn Tyr Lys Ala Tyr Ile Asp Ala Ile
            180                 185                 190

Arg Ala Gln Leu Val Lys Tyr Ser Asp Val His Thr Ile Leu Val Ile
        195                 200                 205

Glu Pro Asp Ser Leu Ala Asn Leu Val Thr Asn Leu Asn Val Ala Lys
    210                 215                 220

Cys Ala Asn Ala Gln Ser Ala Tyr Leu Glu Cys Val Asp Tyr Ala Leu
225                 230                 235                 240

Lys Gln Leu Asn Leu Pro Asn Val Ala Met Tyr Leu Asp Ala Gly His
                245                 250                 255

Ala Gly Trp Leu Gly Trp Pro Ala Asn Leu Gly Pro Ala Ala Thr Leu
            260                 265                 270

Phe Ala Lys Val Tyr Thr Asp Ala Gly Ser Pro Ala Ala Val Arg Gly

```
                275                 280                 285
Leu Ala Thr Asn Val Ala Asn Tyr Asn Ala Trp Ser Leu Ser Thr Cys
        290                 295                 300
Pro Ser Tyr Thr Gln Gly Asp Pro Asn Cys Asp Glu Lys Lys Tyr Ile
305                 310                 315                 320
Asn Ala Met Ala Pro Leu Leu Lys Glu Ala Gly Phe Asp Ala His Phe
                325                 330                 335
Ile Met Asp Thr Ser Arg Asn Gly Val Gln Pro Thr Lys Gln Asn Ala
            340                 345                 350
Trp Gly Asp Trp Cys Asn Val Ile Gly Thr Gly Phe Gly Val Arg Pro
            355                 360                 365
Ser Thr Asn Thr Gly Asp Pro Leu Gln Asp Ala Phe Val Trp Ile Lys
        370                 375                 380
Pro Gly Gly Glu Ser Asp Gly Thr Ser Asn Ser Thr Ser Pro Arg Tyr
385                 390                 395                 400
Asp Ala His Cys Gly Tyr Ser Asp Ala Leu Gln Pro Ala Pro Glu Ala
                405                 410                 415
Gly Thr Trp Phe Gln Ala Tyr Phe Glu Gln Leu Leu Thr Asn Ala Asn
            420                 425                 430
Pro Ser Phe
        435
```

<210> SEQ ID NO 19
<211> LENGTH: 547
<212> TYPE: PRT
<213> ORGANISM: Meripilus giganteus

<400> SEQUENCE: 19

```
Thr Pro Thr Gly Arg Asn Leu Lys Leu His Glu Ala Arg Glu Asp Leu
1               5                   10                  15
Pro Ala Gly Phe Ser Leu Arg Gly Ala Ala Ser Pro Asp Thr Thr Leu
                20                  25                  30
Lys Leu Arg Ile Ala Leu Val Gln Asn Asn Phe Ala Glu Leu Glu Asp
            35                  40                  45
Lys Leu Tyr Asp Val Ser Thr Pro Ser Ser Ala Asn Tyr Gly Asn His
        50                  55                  60
Leu Ser Lys Glu Glu Val Glu Gln Tyr Ile Ala Pro Ala Pro Glu Ser
65                  70                  75                  80
Val Lys Ala Val Asn Ala Trp Leu Thr Glu Asn Gly Leu Asp Ala His
                85                  90                  95
Thr Ile Ser Pro Ala Gly Asp Trp Leu Ala Phe Glu Val Pro Val Ser
            100                 105                 110
Lys Ala Asn Glu Leu Phe Asp Ala Asp Phe Ser Val Phe Thr His Asp
        115                 120                 125
Glu Ser Gly Leu Glu Ala Ile Arg Thr Leu Ala Tyr Ser Ile Pro Ala
    130                 135                 140
Glu Leu Gln Gly His Leu Asp Leu Val His Pro Thr Val Thr Phe Pro
145                 150                 155                 160
Asn Pro Asn Ala His Leu Pro Val Val Arg Ser Thr Gln Pro Ile Arg
                165                 170                 175
Asn Leu Thr Gly Arg Ala Ile Pro Ala Ser Cys Ala Ser Thr Ile Thr
            180                 185                 190
Pro Ala Cys Leu Gln Ala Ile Tyr Gly Ile Pro Thr Thr Lys Ala Thr
        195                 200                 205
```

```
Gln Ser Ser Asn Lys Leu Ala Val Ser Gly Phe Ile Asp Gln Phe Ala
    210                 215                 220
Asn Lys Ala Asp Leu Lys Ser Phe Leu Ala Gln Phe Arg Lys Asp Ile
225                 230                 235                 240
Ser Ser Ser Thr Thr Phe Ser Leu Gln Thr Leu Asp Gly Gly Glu Asn
                245                 250                 255
Asp Gln Ser Pro Ser Glu Ala Gly Ile Glu Ala Asn Leu Asp Ile Gln
            260                 265                 270
Tyr Thr Val Gly Leu Ala Thr Gly Val Pro Thr Thr Phe Ile Ser Val
        275                 280                 285
Gly Asp Asp Phe Gln Asp Gly Asn Leu Glu Gly Phe Leu Asp Ile Ile
    290                 295                 300
Asn Phe Leu Leu Gly Glu Ser Asn Pro Pro Gln Val Leu Thr Thr Ser
305                 310                 315                 320
Tyr Gly Gln Asn Glu Asn Thr Ile Ser Ala Lys Leu Ala Asn Gln Leu
                325                 330                 335
Cys Asn Ala Tyr Ala Gln Leu Gly Ala Arg Gly Thr Ser Ile Leu Phe
            340                 345                 350
Ala Ser Gly Asp Gly Gly Val Ser Gly Ser Gln Ser Ala His Cys Ser
        355                 360                 365
Asn Phe Val Pro Thr Phe Pro Ser Gly Cys Pro Phe Met Thr Ser Val
    370                 375                 380
Gly Ala Thr Gln Gly Val Ser Pro Glu Thr Ala Ala Phe Ser Ser
385                 390                 395                 400
Gly Gly Phe Ser Asn Val Phe Gly Ile Pro Ser Tyr Gln Ala Ser Ala
                405                 410                 415
Val Ser Gly Tyr Leu Ser Ala Leu Gly Ser Thr Asn Ser Gly Lys Phe
            420                 425                 430
Asn Arg Ser Gly Arg Gly Phe Pro Asp Val Ser Thr Gln Gly Val Asp
        435                 440                 445
Phe Gln Ile Val Ser Gly Gly Gln Thr Ile Gly Val Asp Gly Thr Ser
    450                 455                 460
Cys Ala Ser Pro Thr Phe Ala Ser Val Ile Ser Leu Val Asn Asp Arg
465                 470                 475                 480
Leu Ile Ala Ala Gly Lys Ser Pro Leu Gly Phe Leu Asn Pro Phe Leu
                485                 490                 495
Tyr Ser Ser Ala Gly Lys Ala Ala Leu Asn Asp Val Thr Ser Gly Ser
            500                 505                 510
Asn Pro Gly Cys Ser Thr Asn Gly Phe Pro Ala Lys Ala Gly Trp Asp
        515                 520                 525
Pro Val Thr Gly Leu Gly Thr Pro Asn Phe Ala Lys Leu Leu Thr Ala
    530                 535                 540
Val Gly Leu
545

<210> SEQ ID NO 20
<211> LENGTH: 3164
<212> TYPE: DNA
<213> ORGANISM: Talaromyces funiculosus

<400> SEQUENCE: 20
atgtatagtg caacgctact tcaggccctg tgccttctgc ccttggccgc aggactcccg      60
ttcaacgagc gagtagatca agtcctccgc tcatatgagg tgacctcaaa actcgactcc     120
cgcagcacca aaccttcaaa acatggccac acctaccaga ctcaattcct cggcgtaacc     180
```

```
tgggaccaac gcaactggcg cctccaaagc accgtcctcg atcagggaca ttatgagtct    240
cgtggatcca ttgccaacgg ctacattggc ctaaacgtcg ccggtgctgg ccccttgttt    300
gagctggatt cccccgtcga tggcgatgta atcaatggct ggcctctgtt ttcgcgtcga    360
cagacgtttg ctgggttagc gggattttac gatttacagc ctagaactaa tggtacgaat    420
tttccgtggt tgtctcagta tggcgatgat agcgcaatta gcggtgtgcc gcattggggt    480
gggatggtct tagatttggg tgacggagag tatctcgatg cgacggtgga caattccacc    540
atatcggatt atacgactac ttatgattat aaagcgggtg ttttgtcgtg ggattacaaa    600
tggaccccga aaaatgccaa tgggtcgttt ggaataagct acaagatctt tgcgaacaag    660
cttgatgtta atcaggctgt ggtgcaattg agcattactc cgtcgacgaa tgggtcagcg    720
tctgtggtga atgtgattga tggatatgcc gctgttcgga cggactttgt ctcatcgggg    780
aatgagagtg acgttgtcta caccgctgtc aaacctaatg gcgtgaccaa tgttaccgca    840
tggatctata ctgcgttgga tggagatgat gcttttgaca tttcttcggc ggctcttgtg    900
aacgataagc catacgtgca tcaaaatgac tcttcgattg cgcagtctgt caatgttaca    960
ttcactgccg gtactaccat cacgatcaac aaatttgtcg gcgctgcatc taccgatgca   1020
ttcccggacc ctcaaagcac cgccagagaa gctgccttgt ctgctcgtcg cagaggcttt   1080
gacgacctct tccgctctca catctccgaa tgggctcaag tcatgcccga cgactccgtc   1140
gacgatttca cactcgcaaa cggcactcta cccaatgaca cgttcatcat cgaatctgct   1200
gtaatggccg ttgtaaatcc ttactaccta ctacagaata cggttgggcc aaatgctctt   1260
cgtcgagtaa acaatgcccc ggtcaatgac tggagtatac ccgtcggcgg tctgacgtcg   1320
gattcttacg ctggacaaat cttctgggat gccgatgtct ggatgcagcc tggcctggtc   1380
gcagcattcc ctgaatctgc taagcgtatc actaattacc gagcagccaa atattcccaa   1440
gccctggaaa atgcaaagac ggcatacact agttcccaga accagacgtg gttctcgccc   1500
gatgctgcaa tttactcatg gactagtgga agagtcggca actgtactgc cacaggtcca   1560
tgctgggatt atgaatatca cttgaacggc gacatcggaa tttcgcttgt caacgagtgg   1620
gttgtcagcg gtgataacga gactttcaag aacaagcatt tcccaattta caactccatt   1680
gcgacgttgt atggagactt gttgaaaaag aatggtagtt attacacact cactaacatg   1740
actgatcctg atgaatatgc aaacaatgtt gatgctggtg gatatacgat gacgctgatt   1800
tcgcagacgt tgtcgaatgc caacgcattc cggaaacagt ttggcatgaa cgagaacaca   1860
acctggacag agatggcaga caacattctc ttgattcgcg agaatgatgt aaccctcgag   1920
tatacaacta tgaacaacag tgtggccgtc aaacaggccg atgtgattct gtccaccttc   1980
ccattggact ataccaaaaa ctacaccacc agcgctgctc tcaatgatct agattacgta   2040
tgttctccct atccagtcat tcaataacct gctaacattc acagtacgcg ctgaaacaat   2100
ctcctgacgg tcccggcatg acatacgcca tcttctccat cgttgccaac gacgtttccc   2160
catctggctg ctcagcatac acctatgccc aatattccta cgacccgtac atccgcggac   2220 cattttttcca attctccgaa caactactag atgactatac tatcaatggc ggcacgcatc   2280
ccgccttccc cttttttgact ggtcacggag gcgcaaacca ggtcgttctg tacgggtatc   2340
tgggtctgag gctgctaccg gacgatatgt tgcatatcga tcccaaccta ccgcctcaaa   2400
ttcccagcat taaatatcgc actttctact ggcgcggatg gccatccaa gcagcctcaa   2460 attacacaca cactaccatt caacgcgcaa caacagtcgc gccattatca accgccgacc   2520
```

-continued

```
caacctacgc taataagagc atacatgtct cggtcggcca caacaccgtc aactccacaa    2580
cctattccct gtctgcgaac gggtctgcgc tcgttgtgcc taacagacaa atcggctcca    2640
tcaacactgt tgctggcaac gtggtgcagt gcaaatccgt tttgtcgaca gacgcatacc    2700
aaaaggggca ataccccatc tcggcggttg atggtgcagc gtcgacgaag tggcagcctg    2760
agtttgcggc gaacattagc tctttgacag tggatctgac cggtagcaat gttagtagtg    2820
tgtctgggtt ctattttgat tgggctcagg caccgcctac caatatcact gtactcctac    2880
acaactcgtc atctgcagca ctcgcttctt ctggcgacaa acctggaagc tcggcagtga    2940
cattgaatat aacaatctca aaccccctaca acgcatcaac ctacaacgcg aatatcatcg    3000
cattaccttc tagtaattcg acaaactata cgttcccggc accggtacca aagccgaggt    3060
atgcaacctt gtttgtgcag gggaatcagg cgctggatga gacagataca aaatctggga    3120
atggtaccgg agcgacggtt gcggagtggg cgatattgag ttga                     3164
```

<210> SEQ ID NO 21
<211> LENGTH: 1038
<212> TYPE: PRT
<213> ORGANISM: Talaromyces funiculosus

<400> SEQUENCE: 21

```
Met Tyr Ser Ala Thr Leu Leu Gln Ala Leu Cys Leu Leu Pro Leu Ala
1               5                   10                  15

Ala Gly Leu Pro Phe Asn Glu Arg Val Asp Gln Val Leu Arg Ser Tyr
            20                  25                  30

Glu Val Thr Ser Lys Leu Asp Ser Arg Ser Thr Lys Pro Ser Lys His
        35                  40                  45

Gly His Thr Tyr Gln Thr Gln Phe Leu Gly Val Thr Trp Asp Gln Arg
    50                  55                  60

Asn Trp Arg Leu Gln Ser Thr Val Leu Asp Gln Gly His Tyr Glu Ser
65                  70                  75                  80

Arg Gly Ser Ile Ala Asn Gly Tyr Ile Gly Leu Asn Val Ala Gly Ala
                85                  90                  95

Gly Pro Leu Phe Glu Leu Asp Ser Pro Val Asp Gly Asp Val Ile Asn
            100                 105                 110

Gly Trp Pro Leu Phe Ser Arg Arg Gln Thr Phe Ala Gly Leu Ala Gly
        115                 120                 125

Phe Tyr Asp Leu Gln Pro Arg Thr Asn Gly Thr Asn Phe Pro Trp Leu
    130                 135                 140

Ser Gln Tyr Gly Asp Asp Ser Ala Ile Ser Gly Val Pro His Trp Gly
145                 150                 155                 160

Gly Met Val Leu Asp Leu Gly Asp Gly Glu Tyr Leu Asp Ala Thr Val
                165                 170                 175

Asp Asn Ser Thr Ile Ser Asp Tyr Thr Thr Thr Tyr Asp Tyr Lys Ala
            180                 185                 190

Gly Val Leu Ser Trp Asp Tyr Lys Trp Thr Pro Lys Asn Ala Asn Gly
        195                 200                 205

Ser Phe Gly Ile Ser Tyr Lys Ile Phe Ala Asn Lys Leu Asp Val Asn
    210                 215                 220

Gln Ala Val Val Gln Leu Ser Ile Thr Pro Ser Thr Asn Gly Ser Ala
225                 230                 235                 240

Ser Val Val Asn Val Ile Asp Gly Tyr Ala Ala Val Arg Thr Asp Phe
                245                 250                 255

Val Ser Ser Gly Asn Glu Ser Asp Val Val Tyr Thr Ala Val Lys Pro
```

```
            260                 265                 270
Asn Gly Val Thr Asn Val Thr Ala Trp Ile Tyr Thr Ala Leu Asp Gly
            275                 280                 285

Asp Asp Ala Phe Asp Ile Ser Ser Ala Ala Leu Val Asn Asp Lys Pro
            290                 295                 300

Tyr Val His Gln Asn Asp Ser Ser Ile Ala Gln Ser Val Asn Val Thr
305                 310                 315                 320

Phe Thr Ala Gly Thr Thr Ile Thr Ile Asn Lys Phe Val Gly Ala Ala
                325                 330                 335

Ser Thr Asp Ala Phe Pro Asp Pro Gln Ser Thr Ala Arg Glu Ala Ala
            340                 345                 350

Leu Ser Ala Arg Arg Gly Phe Asp Asp Leu Phe Arg Ser His Ile
            355                 360                 365

Ser Glu Trp Ala Gln Val Met Pro Asp Asp Ser Val Asp Asp Phe Thr
            370                 375                 380

Leu Ala Asn Gly Thr Leu Pro Asn Asp Thr Phe Ile Ile Glu Ser Ala
385                 390                 395                 400

Val Met Ala Val Val Asn Pro Tyr Tyr Leu Leu Gln Asn Thr Val Gly
                405                 410                 415

Pro Asn Ala Leu Arg Arg Val Asn Asn Ala Pro Val Asn Asp Trp Ser
                420                 425                 430

Ile Pro Val Gly Gly Leu Thr Ser Asp Ser Tyr Ala Gly Gln Ile Phe
            435                 440                 445

Trp Asp Ala Asp Val Trp Met Gln Pro Gly Leu Val Ala Ala Phe Pro
            450                 455                 460

Glu Ser Ala Lys Arg Ile Thr Asn Tyr Arg Ala Ala Lys Tyr Ser Gln
465                 470                 475                 480

Ala Leu Glu Asn Ala Lys Thr Ala Tyr Thr Ser Ser Gln Asn Gln Thr
                485                 490                 495

Trp Phe Ser Pro Asp Ala Ala Ile Tyr Ser Trp Thr Ser Gly Arg Val
            500                 505                 510

Gly Asn Cys Thr Ala Thr Gly Pro Cys Trp Asp Tyr Glu Tyr His Leu
            515                 520                 525

Asn Gly Asp Ile Gly Ile Ser Leu Val Asn Glu Trp Val Val Ser Gly
            530                 535                 540

Asp Asn Glu Thr Phe Lys Asn Lys His Phe Pro Ile Tyr Asn Ser Ile
545                 550                 555                 560

Ala Thr Leu Tyr Gly Asp Leu Leu Lys Lys Asn Gly Ser Tyr Tyr Thr
                565                 570                 575

Leu Thr Asn Met Thr Asp Pro Asp Glu Tyr Ala Asn Asn Val Asp Ala
            580                 585                 590

Gly Gly Tyr Thr Met Thr Leu Ile Ser Gln Thr Leu Ser Asn Ala Asn
            595                 600                 605

Ala Phe Arg Lys Gln Phe Gly Met Asn Glu Asn Thr Thr Trp Thr Glu
            610                 615                 620

Met Ala Asp Asn Ile Leu Leu Ile Arg Glu Asn Asp Val Thr Leu Glu
625                 630                 635                 640

Tyr Thr Thr Met Asn Asn Ser Val Ala Val Lys Gln Ala Asp Val Ile
                645                 650                 655

Leu Ser Thr Phe Pro Leu Asp Tyr Thr Lys Asn Tyr Thr Thr Ser Ala
            660                 665                 670

Ala Leu Asn Asp Leu Asp Tyr Tyr Ala Leu Lys Gln Ser Pro Asp Gly
            675                 680                 685
```

Pro Gly Met Thr Tyr Ala Ile Phe Ser Ile Val Ala Asn Asp Val Ser
        690                 695                 700

Pro Ser Gly Cys Ser Ala Tyr Thr Tyr Ala Gln Tyr Ser Tyr Asp Pro
705                 710                 715                 720

Tyr Ile Arg Gly Pro Phe Phe Gln Phe Ser Glu Gln Leu Leu Asp Asp
                725                 730                 735

Tyr Thr Ile Asn Gly Gly Thr His Pro Ala Phe Pro Phe Leu Thr Gly
            740                 745                 750

His Gly Gly Ala Asn Gln Val Val Leu Tyr Gly Tyr Leu Gly Leu Arg
        755                 760                 765

Leu Leu Pro Asp Asp Met Leu His Ile Asp Pro Asn Leu Pro Pro Gln
770                 775                 780

Ile Pro Ser Ile Lys Tyr Arg Thr Phe Tyr Trp Arg Gly Trp Pro Ile
785                 790                 795                 800

Gln Ala Ala Ser Asn Tyr Thr His Thr Thr Ile Gln Arg Ala Thr Thr
                805                 810                 815

Val Ala Pro Leu Ser Thr Ala Asp Pro Thr Tyr Ala Asn Lys Ser Ile
            820                 825                 830

His Val Ser Val Gly His Asn Thr Val Asn Ser Thr Thr Tyr Ser Leu
        835                 840                 845

Ser Ala Asn Gly Ser Ala Leu Val Val Pro Asn Arg Gln Ile Gly Ser
850                 855                 860

Ile Asn Thr Val Ala Gly Asn Val Val Gln Cys Lys Ser Val Leu Ser
865                 870                 875                 880

Thr Asp Ala Tyr Gln Lys Gly Gln Tyr Pro Ile Ser Ala Val Asp Gly
                885                 890                 895

Ala Ala Ser Thr Lys Trp Gln Pro Glu Phe Ala Ala Asn Ile Ser Ser
            900                 905                 910

Leu Thr Val Asp Leu Thr Gly Ser Asn Val Ser Ser Val Ser Gly Phe
        915                 920                 925

Tyr Phe Asp Trp Ala Gln Ala Pro Pro Thr Asn Ile Thr Val Leu Leu
930                 935                 940

His Asn Ser Ser Ser Ala Ala Leu Ala Ser Ser Gly Asp Lys Pro Gly
945                 950                 955                 960

Ser Ser Ala Val Thr Leu Asn Ile Thr Ile Ser Asn Pro Tyr Asn Ala
                965                 970                 975

Ser Thr Tyr Asn Ala Asn Ile Ile Ala Leu Pro Ser Ser Asn Ser Thr
            980                 985                 990

Asn Tyr Thr Phe Pro Ala Pro Val Pro Lys Pro Arg Tyr Ala Thr Leu
        995                 1000                1005

Phe Val Gln Gly Asn Gln Ala Leu Asp Glu Thr Asp Thr Lys Ser
    1010                1015                1020

Gly Asn Gly Thr Gly Ala Thr Val Ala Glu Trp Ala Ile Leu Ser
1025                1030                1035

<210> SEQ ID NO 22
<211> LENGTH: 3608
<212> TYPE: DNA
<213> ORGANISM: Talaromyces leycettanus

<400> SEQUENCE: 22
atgcagtcaa agctcctggc tctgctgccg cttctgctgc aactccctgc agtaagcggc    60
acgtctgcca acgcgcgcat caacagatgc gtcaagaaac acgcaggtgg gaaaacccca   120

```
agtggcccat ccaacaacac ctatcaaacc agattcccccg gagtcacctg ggaccaggac    180
aactggtgcc tctccacgac caccctggac cagggtcact acgaatcgcg cggctccgtc    240
gccaatgggt acttgggtat taatgttgcc agcgttggcc cgttcttcga atttgacaca    300
cccgtcgatg cgacgtgat caatggctgg ccttttgttcg accggcgcat gtcctttgcc    360
accatcagtg gcttctggga ccagcagccc acgacgaatg gatccaactt cccctggctg    420
tatcagtacg gtggtgagag cgtcatcagc ggtgtgcctc actggagcgg cctgattctc    480
gatctgggcg acaacaccta cttggacgcg acggtggaca gccgcaccat ttcgggcttc    540
agcacgacgt atgacttcaa gtcgggtgtt ctgtcctggt cctatcagtg gactcccgcc    600
ggaaacatgg gctcctacaa catcacgtac cgtctctttg cgcacaagct gtacgtcaac    660
caggccgtcg tggacatgga ggttgtctcc tcgacggaag caaaggccac cgtcgtgaac    720
gtgattgatg gtgcctcggc tgtccgcacg gattttgtgg aatccggcca ggatgacggt    780
gcgatctaca cggctgtgcg gccgtgggga atcgccaacg tcacggccta catttatgcc    840
aacatcacgg gctccgacaa cgtggacatg cgctctcgcg cgctggttac gaacaagccg    900
tacgtcaacg gcaatgcctc gtccatcacg caagccgtca acgttcactt cactcctgga    960
aagagcgttc gcatcaccaa gtttgtcggc ggtgcctcgt cggatgcgtt ttccaaccct   1020
cagcagatcg ccaagcaggc ttgttcgacc gcccaggcca acggatatgt gaagtcgctg   1080
cgttcccacg ttgccgagtg ggccagcgtc atgccggatg actctgtcga tgactttacc   1140
ttccccagca atggcactct gcccgcagat gagtacatca tcgaatcgca aatcatctcc   1200
gtggcgaata cgtactatct cttgcagaac acggtcggca agaacgccat caatgcatcc   1260
tcgagcaccg agctgaacaa ggactccatc gccgtcggtg gtctgacttc ggaatcgtac   1320
gccggtatga tcttctggga cgccgacgtc tggatgcaac cgggtcttgt cgcgtcccat   1380
cccgaggcgg cccagcgcat caccaactat cgagtggcca aatatcccca ggccaaagcg   1440
aacgttgcga ctgcctatca gagctctaag aaccagacaa acttctcccc ggacgcagct   1500
gtttactctt ggacgagtgc tcggtatgga aactgcactg ccaccggtcc ttgctgggat   1560
tacgagtatc atttgaacgg cgatattgga ctgtccatca tcaatcagta tgtggccagc   1620
ggtgacactc agaccttcaa ggagaagctc ttcccggttt tcgactccgt tgcgacactt   1680
tactcgaata ttgttcagaa gaatggctcg tcgtggactt tgactaacat gactgatcct   1740
gtatgtctct cccccttgtct cttgtctctt gtttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttggt tgtgtgctt ggctgacgtg tctaggatga atatgcaaac    2040
caggtcgatg ccggtggtta caccatgccc ctgattgctc agacgctgtt gtacgccaac   2100
tctttccgcc agcaattcgg tcttgagacc aacgacacgt ggaatgagat tgcacaggac   2160
gtcttggtga tccgcgagaa tggtgtcacg ctggaattca ccaccatgaa cggaagtgct   2220
gtggtcaagc aggccgacgt ggtgctggac acttatcctc tgggttatac acacaactac   2280
gggcccacag atgctctgaa tgacttggac tacgtgagtg aaacgacgcc tttctgatgg   2340
gatcctggag ttactgactt gaccagtatg ccaacaggca atcgcccgac ggccctgcca   2400
tgacctgggc catcttctcc gtcgtcgcca accaaatctc tccttcgggc tgctctgcgt   2460
acacgtacgc ccagtacgcc ttcagcccct acgctcgcgc acccttctac cagcttttccg   2520
```

```
agcagttgat cgacgacgcc tcgctcaacg gcggcactca ccctgcctac ccgttcttga   2580
ccggccacgg cggtgccctc caagtcaacc ttttcgggta cctgggattc cgctacctcc   2640
ctgacaatgt catccacatt gatcccaacc ttccaccaca aatcccccac atcacctacc   2700
gcaccttcta ctggcgcggc tggcccatca ccgccgcctc cacctacacc cacacgacgc   2760
tcagccgagc ctggaacgtc tcgtccctcg acagcgccga ccccaaattc gccaacgcct   2820
ccatccccgt ccacgtcggc ctcgaatcga acgtgaccgt ctaccgtctc cccgtcaacg   2880
gcaccctcac cgtccccaac cgcatggtcg gctccaagaa cactctcgct ggcaacatgg   2940
tgcagtgccg tcccgtccaa tccatggacg gctatcaacc cggccaattc cccatctccg   3000
tcgtcgacgg tgcctcctcc acgaaatggc aacctctcta ctctgcgaac gtctcctccg   3060
tgacagttac tctgtcctcg tcagccgtcg gcaagagtgt gaacgggttc tacttcgact   3120
gggcgcaaaa cccacccgtc aacgccgcgg tggtcttcca caactcttcc tttgcacaga   3180
accccgccac gacgttctcg ttcgacaacc cttccgccag tggcaacttg tactccgttg   3240
tttcggtcct gaaggatatc caattgtccg atccctatga tcctgcaact acagacctgg   3300
acgtcatcgc cattccaaag ggaaatacca cgaacgtaac tctttcctcg cccgtccctg   3360
ccgcgagata cgccacgctc ttcatccagg gtaaccaggc gaacagtccc gcggaggtgg   3420
ctgcgaagaa cggcacgggc gcgacggtcg ccgagtgggc gattctaggg caggaggtgc   3480
agaataacgg ttacggggat cagattgaag cgagaagact cgatgtgagg ggcgcggctg   3540
cgttgtcggg gatggggagt ttcacgcagc ggaggaagag gaagatgatt ttgccgcggt   3600
tcgattag                                                           3608
```

<210> SEQ ID NO 23  
<211> LENGTH: 1089  
<212> TYPE: PRT  
<213> ORGANISM: Talaromyces leycettanus

<400> SEQUENCE: 23

```
Met Gln Ser Lys Leu Leu Ala Leu Leu Pro Leu Leu Leu Gln Leu Pro
1               5                   10                  15

Ala Val Ser Gly Thr Ser Ala Asn Ala Arg Ile Asn Arg Cys Val Lys
            20                  25                  30

Lys His Ala Gly Lys Thr Pro Ser Gly Pro Ser Asn Asn Thr Tyr
        35                  40                  45

Gln Thr Arg Phe Pro Gly Val Thr Trp Asp Gln Asp Asn Trp Cys Leu
    50                  55                  60

Ser Thr Thr Thr Leu Asp Gln Gly His Tyr Glu Ser Arg Gly Ser Val
65                  70                  75                  80

Ala Asn Gly Tyr Leu Gly Ile Asn Val Ala Ser Val Gly Pro Phe Phe
                85                  90                  95

Glu Phe Asp Thr Pro Val Asp Gly Asp Val Ile Asn Gly Trp Pro Leu
            100                 105                 110

Phe Asp Arg Arg Met Ser Phe Ala Thr Ile Ser Gly Phe Trp Asp Gln
        115                 120                 125

Gln Pro Thr Thr Asn Gly Ser Asn Phe Pro Trp Leu Tyr Gln Tyr Gly
    130                 135                 140

Gly Glu Ser Val Ile Ser Gly Val Pro His Trp Ser Gly Leu Ile Leu
145                 150                 155                 160

Asp Leu Gly Asp Asn Thr Tyr Leu Asp Ala Thr Val Asp Ser Arg Thr
                165                 170                 175
```

-continued

Ile Ser Gly Phe Ser Thr Thr Tyr Asp Phe Lys Ser Gly Val Leu Ser
            180                 185                 190

Trp Ser Tyr Gln Trp Thr Pro Ala Gly Asn Met Gly Ser Tyr Asn Ile
        195                 200                 205

Thr Tyr Arg Leu Phe Ala His Lys Leu Tyr Val Asn Gln Ala Val Val
    210                 215                 220

Asp Met Glu Val Val Ser Ser Thr Glu Ala Lys Ala Thr Val Val Asn
225                 230                 235                 240

Val Ile Asp Gly Ala Ser Ala Val Arg Thr Asp Phe Val Glu Ser Gly
                245                 250                 255

Gln Asp Asp Gly Ala Ile Tyr Thr Ala Val Arg Pro Trp Gly Ile Ala
            260                 265                 270

Asn Val Thr Ala Tyr Ile Tyr Ala Asn Ile Thr Gly Ser Asp Asn Val
        275                 280                 285

Asp Met Arg Ser Arg Ala Leu Val Thr Asn Lys Pro Tyr Val Asn Gly
    290                 295                 300

Asn Ala Ser Ser Ile Thr Gln Ala Val Asn Val His Phe Thr Pro Gly
305                 310                 315                 320

Lys Ser Val Arg Ile Thr Lys Phe Val Gly Gly Ala Ser Ser Asp Ala
                325                 330                 335

Phe Ser Asn Pro Gln Gln Ile Ala Lys Gln Ala Cys Ser Thr Ala Gln
            340                 345                 350

Ala Asn Gly Tyr Val Lys Ser Leu Arg Ser His Val Ala Glu Trp Ala
        355                 360                 365

Ser Val Met Pro Asp Asp Ser Val Asp Asp Phe Thr Phe Pro Ser Asn
    370                 375                 380

Gly Thr Leu Pro Ala Asp Glu Tyr Ile Ile Glu Ser Gln Ile Ile Ser
385                 390                 395                 400

Val Ala Asn Thr Tyr Tyr Leu Leu Gln Asn Thr Val Gly Lys Asn Ala
                405                 410                 415

Ile Asn Ala Ser Ser Ser Thr Glu Leu Asn Lys Asp Ser Ile Ala Val
            420                 425                 430

Gly Gly Leu Thr Ser Glu Ser Tyr Ala Gly Met Ile Phe Trp Asp Ala
        435                 440                 445

Asp Val Trp Met Gln Pro Gly Leu Val Ala Ser His Pro Glu Ala Ala
    450                 455                 460

Gln Arg Ile Thr Asn Tyr Arg Val Ala Lys Tyr Pro Gln Ala Lys Ala
465                 470                 475                 480

Asn Val Ala Thr Ala Tyr Gln Ser Ser Lys Asn Gln Thr Asn Phe Ser
                485                 490                 495

Pro Asp Ala Ala Val Tyr Ser Trp Thr Ser Ala Arg Tyr Gly Asn Cys
            500                 505                 510

Thr Ala Thr Gly Pro Cys Trp Asp Tyr Glu Tyr His Leu Asn Gly Asp
        515                 520                 525

Ile Gly Leu Ser Ile Ile Asn Gln Tyr Val Ala Ser Gly Asp Thr Gln
    530                 535                 540

Thr Phe Lys Glu Lys Leu Phe Pro Val Phe Asp Ser Val Ala Thr Leu
545                 550                 555                 560

Tyr Ser Asn Ile Val Gln Lys Asn Gly Ser Ser Trp Thr Leu Thr Asn
                565                 570                 575

Met Thr Asp Pro Asp Glu Tyr Ala Asn Gln Val Asp Ala Gly Gly Tyr
            580                 585                 590

-continued

```
Thr Met Pro Leu Ile Ala Gln Thr Leu Leu Tyr Ala Asn Ser Phe Arg
        595                 600                 605

Gln Gln Phe Gly Leu Glu Thr Asn Asp Thr Trp Asn Glu Ile Ala Gln
610                 615                 620

Asp Val Leu Val Ile Arg Glu Asn Gly Val Thr Leu Glu Phe Thr Thr
625                 630                 635                 640

Met Asn Gly Ser Ala Val Val Lys Gln Ala Asp Val Val Leu Asp Thr
                645                 650                 655

Tyr Pro Leu Gly Tyr Thr His Asn Tyr Gly Pro Thr Asp Ala Leu Asn
                660                 665                 670

Asp Leu Asp Tyr Tyr Ala Asn Arg Gln Ser Pro Asp Gly Pro Ala Met
            675                 680                 685

Thr Trp Ala Ile Phe Ser Val Val Ala Asn Gln Ile Ser Pro Ser Gly
            690                 695                 700

Cys Ser Ala Tyr Thr Tyr Ala Gln Tyr Ala Phe Ser Pro Tyr Ala Arg
705                 710                 715                 720

Ala Pro Phe Tyr Gln Leu Ser Glu Gln Leu Ile Asp Asp Ala Ser Leu
                725                 730                 735

Asn Gly Gly Thr His Pro Ala Tyr Pro Phe Leu Thr Gly His Gly Gly
                740                 745                 750

Ala Leu Gln Val Asn Leu Phe Gly Tyr Leu Gly Phe Arg Tyr Leu Pro
            755                 760                 765

Asp Asn Val Ile His Ile Asp Pro Asn Leu Pro Pro Gln Ile Pro His
770                 775                 780

Ile Thr Tyr Arg Thr Phe Tyr Trp Arg Gly Trp Pro Ile Thr Ala Ala
785                 790                 795                 800

Ser Thr Tyr Thr His Thr Thr Leu Ser Arg Ala Trp Asn Val Ser Ser
                805                 810                 815

Leu Asp Ser Ala Asp Pro Lys Phe Ala Asn Ala Ser Ile Pro Val His
                820                 825                 830

Val Gly Leu Glu Ser Asn Val Thr Val Tyr Arg Leu Pro Val Asn Gly
            835                 840                 845

Thr Leu Thr Val Pro Asn Arg Met Val Gly Ser Lys Asn Thr Leu Ala
850                 855                 860

Gly Asn Met Val Gln Cys Arg Pro Val Gln Ser Met Asp Gly Tyr Gln
865                 870                 875                 880

Pro Gly Gln Phe Pro Ile Ser Val Val Asp Gly Ala Ser Ser Thr Lys
                885                 890                 895

Trp Gln Pro Leu Tyr Ser Ala Asn Val Ser Ser Val Thr Val Thr Leu
                900                 905                 910

Ser Ser Ser Ala Val Gly Lys Ser Val Asn Gly Phe Tyr Phe Asp Trp
            915                 920                 925

Ala Gln Asn Pro Pro Val Asn Ala Ala Val Val Phe His Asn Ser Ser
930                 935                 940

Phe Ala Gln Asn Pro Ala Thr Thr Phe Ser Phe Asp Asn Pro Ser Ala
945                 950                 955                 960

Ser Gly Asn Leu Tyr Ser Val Val Ser Val Leu Lys Asp Ile Gln Leu
                965                 970                 975

Ser Asp Pro Tyr Asp Pro Ala Thr Thr Asp Leu Asp Val Ile Ala Ile
                980                 985                 990

Pro Lys Gly Asn Thr Thr Asn Val  Thr Leu Ser Ser Pro  Val Pro Ala
            995                 1000                1005

Ala Arg  Tyr Ala Thr Leu Phe  Ile Gln Gly Asn Gln  Ala Asn Ser
```

-continued

```
              1010                1015                1020

Pro Ala Glu Val Ala Ala Lys Asn Gly Thr Gly Ala Thr Val Ala
        1025                1030                1035

Glu Trp Ala Ile Leu Gly Gln Glu Val Gln Asn Asn Gly Tyr Gly
    1040                1045                1050

Asp Gln Ile Glu Ala Arg Arg Leu Asp Val Arg Gly Ala Ala Ala
    1055                1060                1065

Leu Ser Gly Met Gly Ser Phe Thr Gln Arg Arg Lys Arg Lys Met
    1070                1075                1080

Ile Leu Pro Arg Phe Asp
        1085
```

<210> SEQ ID NO 24
<211> LENGTH: 27
<212> TYPE: DNA
<213> ORGANISM: Artificial
<220> FEATURE:
<223> OTHER INFORMATION: PCR primer

<400> SEQUENCE: 24
gaattcgagc tcggtacctt gaagttc                                       27

<210> SEQ ID NO 25
<211> LENGTH: 31
<212> TYPE: DNA
<213> ORGANISM: Artificial
<220> FEATURE:
<223> OTHER INFORMATION: PCR primer

<400> SEQUENCE: 25
ggtggatccc cagttgtgta tatagaggat t                                  31

<210> SEQ ID NO 26
<211> LENGTH: 26
<212> TYPE: DNA
<213> ORGANISM: Artificial
<220> FEATURE:
<223> OTHER INFORMATION: PCR primer

<400> SEQUENCE: 26
tggccggcgc ggctgggtcg actcta                                        26

<210> SEQ ID NO 27
<211> LENGTH: 29
<212> TYPE: DNA
<213> ORGANISM: Artificial
<220> FEATURE:
<223> OTHER INFORMATION: PCR primer

<400> SEQUENCE: 27
gaccatgatt acgccaagct tttgaagtt                                     29

<210> SEQ ID NO 28
<211> LENGTH: 25
<212> TYPE: DNA
<213> ORGANISM: Artificial
<220> FEATURE:
<223> OTHER INFORMATION: PCR primer

<400> SEQUENCE: 28
ctatatacac aactggggat ccacc                                         25

<210> SEQ ID NO 29

```
<211> LENGTH: 26
<212> TYPE: DNA
<213> ORGANISM: Artificial
<220> FEATURE:
<223> OTHER INFORMATION: PCR primer

<400> SEQUENCE: 29
tagagtcgac ccagccgcgc cggcca                                          26

<210> SEQ ID NO 30
<211> LENGTH: 62
<212> TYPE: DNA
<213> ORGANISM: Artificial
<220> FEATURE:
<223> OTHER INFORMATION: PCR primer

<400> SEQUENCE: 30
ctatatacac aactggggat ccaccatgca gtcaaagctc ctggctctgc tgccgcttct     60
gc                                                                    62

<210> SEQ ID NO 31
<211> LENGTH: 65
<212> TYPE: DNA
<213> ORGANISM: Artificial
<220> FEATURE:
<223> OTHER INFORMATION: PCR primer

<400> SEQUENCE: 31
ctatatacac aactggggat ccaccatgta tagtgcaacg ctacttcagg ccctgtgcct     60
tctgc                                                                 65

<210> SEQ ID NO 32
<211> LENGTH: 52
<212> TYPE: DNA
<213> ORGANISM: Artificial
<220> FEATURE:
<223> OTHER INFORMATION: PCR primer

<400> SEQUENCE: 32
tagagtcgac ccagccgcgc cggccactaa tcgaaccgcg gcaaaatcat ct             52

<210> SEQ ID NO 33
<211> LENGTH: 50
<212> TYPE: DNA
<213> ORGANISM: Artificial
<220> FEATURE:
<223> OTHER INFORMATION: PCR primer

<400> SEQUENCE: 33
tagagtcgac ccagccgcgc cggccatcaa ctcaatatcg cccactccgc                50

<210> SEQ ID NO 34
<211> LENGTH: 1034
<212> TYPE: PRT
<213> ORGANISM: Talaromyces cellulolyticus

<400> SEQUENCE: 34

Met His Ser Ala Ala Leu Leu Gln Ala Leu Cys Leu Leu Pro Leu Val
1               5                   10                  15

Ala Gly Leu Pro Phe Asn Glu Arg Val Asp Gln Ile Leu Arg Ser Tyr
            20                  25                  30

Ser Pro Lys Asn Leu Glu Ser Arg Ser Thr Lys His Gly Asn Ser Tyr
        35                  40                  45
```

```
Gln Thr Gln Phe Ser Gly Val Thr Trp Asp Gln Arg Asn Trp Arg Leu
 50                  55                  60
Gln Ser Thr Val Leu Asp Gln Gly His Tyr Glu Ser Arg Gly Ser Ile
 65                  70                  75                  80
Ala Asn Gly Tyr Ile Gly Leu Asn Val Ala Gly Ala Gly Pro Phe Phe
                 85                  90                  95
Glu Leu Asp Thr Ala Val Asp Gly Asp Val Ile Asn Gly Trp Pro Leu
                100                 105                 110
Phe Ser Arg Arg Gln Thr Phe Ala Gly Leu Ala Gly Phe Tyr Asp Leu
                115                 120                 125
Gln Pro Thr Thr Asn Gly Ser Asn Phe Pro Trp Leu Ser Gln Tyr Gly
130                 135                 140
Asp Asp Ser Ala Ile Ser Gly Val Pro His Trp Gly Leu Ile Leu
145                 150                 155                 160
Asp Leu Gly Asp Gly Glu Tyr Leu Asp Ala Thr Val Asp Asn Ser Thr
                165                 170                 175
Ile Ser Asp Tyr Thr Thr Thr Tyr Asp Tyr Lys Ala Gly Val Leu Ser
                180                 185                 190
Trp Asp Tyr Lys Trp Thr Pro Lys Asn Ser Lys Ala Ser Phe Gly Ile
                195                 200                 205
Asn Tyr Lys Ile Phe Ala Asn Lys Leu Asp Val Asn Gln Ala Val Val
210                 215                 220
Gln Leu Ser Ile Thr Pro Ser Ala Asn Gly Ser Gly Ser Val Val Asn
225                 230                 235                 240
Val Ile Asp Gly Tyr Ser Ala Val Arg Thr Asp Phe Val Ser Ser Gly
                245                 250                 255
Asn Glu Ser Asp Val Ile Tyr Thr Ala Val Lys Pro Val Gly Val Asn
                260                 265                 270
Asn Val Thr Ala Trp Ile Tyr Ala Ala Leu Asp Gly Asp Glu Ala Phe
                275                 280                 285
Asp Phe Ser Ser Ala Glu Leu Val Asn Asp Lys Pro Tyr Val His Gln
                290                 295                 300
Asn Asp Ser Ser Ile Ala Gln Ser Val Asn Val Thr Phe Thr Ala Gly
305                 310                 315                 320
Thr Thr Ile Thr Ile Asn Lys Phe Val Gly Ala Ala Ser Thr Asp Ala
                325                 330                 335
Phe Pro Asp Pro Gln Ser Thr Ala Arg Glu Ala Ala Met Thr Ala Arg
                340                 345                 350
Arg Arg Gly Phe Asp Asp Leu Phe Arg Ser His Val Ser Glu Trp Ala
                355                 360                 365
Gln Val Met Pro Asp Asp Ser Val Asp Phe Thr Leu Ala Asn Gly
                370                 375                 380
Thr Leu Pro Asn Asp Thr Phe Ile Ile Glu Ser Ala Val Met Ala Val
385                 390                 395                 400
Val Asn Pro Tyr Tyr Leu Leu Gln Asn Thr Val Gly Ala Asn Ala Leu
                405                 410                 415
Arg Arg Val Asn Asn Ala Pro Val Asn Asp Trp Ser Ile Pro Val Gly
                420                 425                 430
Gly Leu Thr Ser Asp Ser Tyr Ala Gly Gln Ile Phe Trp Asp Ala Asp
                435                 440                 445
Val Trp Met Gln Pro Gly Leu Val Ala Ala Phe Pro Glu Ser Ala Lys
450                 455                 460
Arg Ile Thr Asn Tyr Arg Thr Ala Lys Tyr Ser Gln Ala Leu Glu Asn
```

```
         465                 470                 475                 480
Ala Lys Thr Ala Tyr Thr Ser Ser Gln Asn Gln Thr Ser Phe Ser Ser
                    485                 490                 495

Asp Ala Ala Ile Tyr Ser Trp Thr Ser Gly Arg Tyr Gly Asn Cys Thr
                500                 505                 510

Ala Thr Gly Pro Cys Trp Asp Tyr Glu Tyr His Leu Asn Gly Asp Ile
                515                 520                 525

Gly Ile Ser Leu Val Asn Gln Trp Val Val Ser Gly Asp Asn Glu Thr
                530                 535                 540

Phe Lys Asn Thr His Phe Pro Ile Tyr Asn Ser Ile Ala Thr Leu Tyr
545                 550                 555                 560

Gly Asp Leu Leu Lys Lys Asn Gly Ser Tyr Tyr Thr Leu Thr Asn Met
                565                 570                 575

Thr Asp Pro Asp Glu Tyr Ala Asn Asn Val Asp Ala Gly Gly Tyr Thr
                580                 585                 590

Met Thr Leu Ile Ser Gln Thr Leu Ser Asn Ala Asn Ala Phe Arg Lys
                595                 600                 605

Gln Phe Gly Met Asp Glu Asn Thr Thr Trp Thr Glu Met Ala Asp Asn
                610                 615                 620

Ile Leu Leu Ile Arg Glu Asn Asp Val Thr Leu Glu Tyr Thr Thr Met
625                 630                 635                 640

Asn Asn Ser Val Ala Val Lys Gln Ala Asp Val Ile Leu Ser Thr Phe
                645                 650                 655

Pro Leu Asp Tyr Thr Lys Asn Tyr Thr Thr Ser Ala Ala Leu Asn Asp
                660                 665                 670

Leu Asp Tyr Tyr Ala Leu Lys Gln Ser Pro Asp Gly Pro Gly Met Thr
                675                 680                 685

Tyr Ala Ile Phe Ser Ile Val Ala Asn Asp Val Ser Pro Ser Gly Cys
                690                 695                 700

Ser Ala Tyr Thr Tyr Ala Gln Tyr Ser Tyr Asp Pro Tyr Ile Arg Gly
705                 710                 715                 720

Pro Phe Phe Gln Phe Ser Glu Gln Leu Leu Asp Asp Tyr Thr Ala Asn
                725                 730                 735

Gly Gly Thr His Pro Ala Phe Pro Phe Leu Thr Gly His Gly Gly Ala
                740                 745                 750

Asn Gln Val Val Leu Tyr Gly Tyr Leu Gly Leu Arg Leu Leu Pro Asp
                755                 760                 765

Asp Met Leu His Ile Asp Pro Asn Leu Pro Pro Gln Ile Pro Ser Val
                770                 775                 780

Lys Tyr Arg Thr Phe Tyr Trp Arg Gly Trp Pro Ile Gln Ala Ala Ser
785                 790                 795                 800

Asn Tyr Thr His Thr Thr Ile Gln Arg Ala Thr Ser Val Ala Pro Leu
                805                 810                 815

Ser Thr Ala Asp Pro Val Tyr Ala Asn Thr Ser Ile Ser Val Ser Val
                820                 825                 830

Gly Gln Asn Thr Ala Asn Ser Thr Thr Tyr Ser Leu Pro Val Asn Gly
                835                 840                 845

Ser Ala Ile Val Val Pro Asn Arg Gln Ile Gly Ser Ile Asn Thr Val
                850                 855                 860

Thr Gly Asn Ile Ala Gln Cys Val Ser Val Leu Ser Thr Asp Ala Tyr
865                 870                 875                 880

Gln Pro Gly Gln Tyr Pro Ile Ser Ala Val Asp Gly Ala Ala Ser Thr
                885                 890                 895
```

```
Lys Trp Gln Pro Glu Phe Ala Ala Asn Val Ser Ser Leu Thr Val Asp
                900                 905                 910

Leu Thr Ser Ser Asn Ala Ser Ser Val Ser Gly Phe Tyr Phe Asp Trp
            915                 920                 925

Ala Gln Ala Pro Pro Thr Asn Ile Thr Val Leu Leu His Asn Ser Ser
        930                 935                 940

Ser Ala Ala Leu Thr Ser Ser Thr His Gly Gly Ser Ser Ser Val
945                 950                 955                 960

Ser Leu Asn Ile Thr Thr Ser Asn Pro Tyr Asp Ala Ser Ser Tyr Asp
                965                 970                 975

Ala Asn Val Ile Ala Leu Ser Ser Asn Thr Thr Asn Tyr Thr Phe
            980                 985                 990

Pro Ala Pro Val Ala Lys Pro Arg Tyr Ala Thr Leu Phe Val Gln Gly
        995                 1000                1005

Asn Gln Ala Leu Asp Glu Thr Asp Thr Lys Ala Gly Asn Gly Thr
    1010                1015                1020

Gly Ala Thr Val Ala Glu Trp Ala Ile Leu Ser
1025                1030
```

<210> SEQ ID NO 35
<211> LENGTH: 1040
<212> TYPE: PRT
<213> ORGANISM: Talaromyces verruculosus

<400> SEQUENCE: 35

```
Met Tyr Ser Ala Thr Leu Leu Gln Ala Leu Cys Leu Leu Pro Leu Val
1               5                   10                  15

Ala Gly Leu Pro Phe Asn Glu Arg Val Asp Gln Ile Leu Arg Ser Tyr
            20                  25                  30

Ser Pro Lys Asn Leu Glu Ser Arg Ser Thr Lys His Gly Asn Asn Thr
        35                  40                  45

Lys His Gly Asn Ser Tyr Gln Thr Gln Phe Ser Gly Val Thr Trp Asp
    50                  55                  60

Gln Arg Asn Trp Arg Leu Gln Ser Thr Val Leu Asp Gln Gly His Tyr
65                  70                  75                  80

Glu Ser Arg Gly Ser Ile Ala Asn Gly Tyr Ile Gly Leu Asn Val Ala
                85                  90                  95

Gly Ala Gly Pro Phe Phe Glu Leu Asp Thr Ala Val Asp Gly Asp Val
            100                 105                 110

Ile Asn Gly Trp Pro Leu Phe Ser Arg Arg Gln Thr Phe Ala Gly Leu
        115                 120                 125

Ala Gly Phe Tyr Asp Leu Gln Pro Thr Thr Asn Gly Ser Asn Phe Pro
    130                 135                 140

Trp Leu Asp Gln Tyr Gly Asp Ser Ala Ile Ser Gly Val Pro His
145                 150                 155                 160

Trp Gly Gly Leu Ile Leu Asp Leu Gly Asp Gly Glu Tyr Leu Asp Ala
                165                 170                 175

Thr Val Asp Asn Ser Thr Ile Ser Asp Tyr Arg Thr Thr Tyr Asp Tyr
            180                 185                 190

Lys Ala Gly Val Leu Ser Trp Asp Tyr Lys Trp Thr Pro Lys Asn Ser
        195                 200                 205

Lys Gly Ser Phe Gly Ile Asn Tyr Lys Ile Phe Ala Asn Lys Leu Asp
    210                 215                 220

Val Asn Gln Ala Val Val Gln Leu Ser Ile Thr Pro Ser Ala Asn Gly
```

```
                225                 230                 235                 240
            Ser Ala Ser Val Val Asn Val Ile Asp Gly Tyr Ser Ala Val Arg Thr
                            245                 250                 255

Asp Phe Val Ser Ser Gly Asn Glu Ser Asp Val Ile Tyr Thr Ala Val
                            260                 265                 270

Lys Pro Val Gly Val Asn Asn Val Thr Ala Trp Ile Tyr Ala Ala Leu
                            275                 280                 285

Asp Gly Asp Glu Ala Phe Asp Phe Ser Ser Ala Glu Leu Val Asn Asp
                            290                 295                 300

Lys Pro Tyr Val His Gln Asn Asp Ser Ser Ile Ala Gln Ser Val Asn
            305                 310                 315                 320

Val Ser Phe Thr Ala Gly Thr Thr Val Thr Ile Asn Lys Phe Val Gly
                            325                 330                 335

Ala Ala Ser Thr Asp Ala Phe Pro Asp Pro Gln Ser Thr Ala Arg Glu
                            340                 345                 350

Ala Ala Leu Thr Ala Arg Arg Arg Gly Phe Asp Asp Leu Phe Arg Ser
                            355                 360                 365

His Ile Ser Glu Trp Ala Gln Val Met Pro Asp Asp Ser Val Asp Asp
                            370                 375                 380

Phe Thr Leu Ala Asn Gly Thr Leu Pro Asn Asp Arg Phe Ile Ile Glu
            385                 390                 395                 400

Ser Ala Val Met Ala Val Val Asn Pro Tyr Tyr Leu Leu Gln Asn Thr
                            405                 410                 415

Val Gly Pro Asn Ala Leu Arg Arg Val Asn Asn Ala Pro Val Asn Asp
                            420                 425                 430

Trp Ser Ile Pro Val Gly Gly Leu Thr Ser Asp Ser Tyr Ala Gly Gln
                            435                 440                 445

Ile Phe Trp Asp Ala Asp Val Trp Met Gln Pro Gly Leu Val Ala Ala
                            450                 455                 460

Phe Pro Glu Ser Ala Lys Arg Ile Thr Asn Tyr Arg Thr Ala Ile Tyr
            465                 470                 475                 480

Ser Gln Ala Leu Glu Asn Ala Lys Thr Ala Tyr Thr Ser Ser Gln Asn
                            485                 490                 495

Gln Thr Ser Phe Ser Ser Asp Ala Ala Ile Tyr Ser Trp Thr Ser Gly
                            500                 505                 510

Arg Tyr Gly Asn Cys Thr Ala Thr Gly Pro Cys Trp Asp Tyr Glu Tyr
                            515                 520                 525

His Leu Asn Gly Asp Ile Gly Ile Ser Leu Val Asn Gln Trp Val Val
            530                 535                 540

Ser Gly Asp Asn Glu Thr Phe Lys Ser Thr His Phe Pro Ile Tyr Asn
            545                 550                 555                 560

Ser Ile Ala Thr Leu Tyr Gly Asp Leu Leu Lys Asn Gly Ser Tyr
                            565                 570                 575

Tyr Thr Leu Thr Asn Met Thr Asp Pro Asp Glu Tyr Ala Asn Asn Val
                            580                 585                 590

Asp Ala Gly Gly Tyr Thr Met Thr Leu Ile Ser Gln Thr Leu Ser Asn
                            595                 600                 605

Ala Asn Ala Phe Arg Lys Gln Phe Gly Met Asp Glu Asn Thr Thr Trp
            610                 615                 620

Thr Glu Met Ala Glu Asn Ile Leu Leu Ile Arg Glu Asn Asp Val Thr
            625                 630                 635                 640

Leu Glu Tyr Thr Thr Met Asn Asn Ser Val Ala Val Lys Gln Ala Asp
                            645                 650                 655
```

```
Val Ile Leu Ser Thr Phe Pro Leu Asp Tyr Thr Lys Asn Tyr Thr Thr
                660                 665                 670

Ser Ala Ala Leu Asn Asp Leu Asp Tyr Tyr Ala Leu Lys Gln Ser Pro
        675                 680                 685

Asp Gly Pro Gly Met Thr Tyr Ala Ile Phe Ser Ile Val Ala Asn Asp
690                 695                 700

Val Ser Pro Ser Gly Cys Ser Ala Tyr Thr Tyr Ala Gln Tyr Ser Tyr
705                 710                 715                 720

Asp Pro Tyr Ile Arg Gly Pro Phe Phe Gln Phe Ser Glu Gln Leu Leu
                725                 730                 735

Asp Asp Tyr Thr Ala Asn Gly Gly Thr His Pro Ala Phe Pro Phe Leu
            740                 745                 750

Thr Gly His Gly Gly Ala Asn Gln Val Val Leu Tyr Gly Tyr Leu Gly
            755                 760                 765

Leu Arg Leu Leu Pro Asp Asp Met Leu His Ile Asp Pro Asn Leu Pro
    770                 775                 780

Pro Gln Ile Pro Ser Val Lys Tyr Arg Thr Phe Tyr Trp Arg Gly Trp
785                 790                 795                 800

Pro Ile Gln Ala Ala Ser Asn Tyr Thr His Thr Thr Ile Gln Arg Ala
                805                 810                 815

Thr Thr Val Ala Pro Leu Ser Thr Ala Asp Gln Ala Tyr Ala Asn Thr
                820                 825                 830

Ser Ile Ser Val Ser Val Gly Gln Asn Thr Ala Asn Ser Thr Thr Tyr
        835                 840                 845

Ser Leu Pro Val Asn Gly Ser Ala Ile Val Val Pro Asn Arg Gln Ile
    850                 855                 860

Gly Ser Ile Asn Thr Val Ala Gly Asn Ile Ala Gln Cys Val Ser Val
865                 870                 875                 880

Leu Ser Thr Asp Ala Tyr Gln Pro Gly Gln Tyr Pro Ile Ser Ala Val
                885                 890                 895

Asp Gly Ala Ala Ser Thr Lys Trp Gln Pro Glu Phe Ala Ala Asn Val
                900                 905                 910

Asn Ser Leu Thr Val Asp Leu Thr Ser Ser Asn Ala Ser Ser Val Ser
        915                 920                 925

Gly Phe Tyr Phe Asp Trp Ala Gln Ala Pro Pro Thr Asn Ile Thr Val
    930                 935                 940

Leu Leu His Asn Ser Ser Ser Val Ala Leu Thr Ser Ser Ser Thr His
945                 950                 955                 960

Gly Gly Ser Ser Ser Val Ser Leu Asn Ile Thr Ile Ser Asn Pro Tyr
                965                 970                 975

Asp Ala Leu Ser Tyr Asp Ala Asn Val Ile Ala Leu Ser Ser Ser Asn
            980                 985                 990

Thr Thr Asn Tyr Thr Phe Pro Ala  Pro Val Ala Lys Pro Arg Tyr Ala
        995                 1000                1005

Thr Leu Leu Val Gln Gly Asn  Gln Ala Leu Asp Glu  Thr Asp Thr
    1010                1015                1020

Lys Ala  Gly Asn Gly Thr Gly  Ala Thr Val Ala Glu  Trp Ala Ile
    1025                1030                1035

Leu Ser
    1040
```